United States Patent
Limphong et al.

(10) Patent No.: US 11,015,204 B2
(45) Date of Patent: May 25, 2021

(54) SYNTHESIS AND STRUCTURE OF HIGH POTENCY RNA THERAPEUTICS

(71) Applicant: Arcturus Therapeutics, Inc., San Diego, CA (US)

(72) Inventors: Pattraranee Limphong, San Diego, CA (US); Carlos G. Perez-Garcia, San Diego, CA (US); Kiyoshi Tachikawa, San Diego, CA (US); Padmanabh Chivukula, San Diego, CA (US); Arisa Cale, San Diego, CA (US); Angel I-Jou Leu, San Diego, CA (US); Jared Davis, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 134 days.

(21) Appl. No.: 15/994,683

(22) Filed: May 31, 2018

(65) Prior Publication Data

US 2019/0002906 A1  Jan. 3, 2019

Related U.S. Application Data

(60) Provisional application No. 62/513,223, filed on May 31, 2017.

(51) Int. Cl.
| | | |
|---|---|---|
| *C12N 15/52* | (2006.01) | |
| *C12N 15/82* | (2006.01) | |
| *C07K 14/805* | (2006.01) | |
| *C07K 14/775* | (2006.01) | |
| *C07K 14/75* | (2006.01) | |
| *C07K 14/47* | (2006.01) | |
| *C07K 14/415* | (2006.01) | |
| *C07K 14/505* | (2006.01) | |
| *A61K 38/01* | (2006.01) | |
| *A61K 38/17* | (2006.01) | |
| *A61K 38/42* | (2006.01) | |
| *A61K 38/36* | (2006.01) | |
| *A61K 38/18* | (2006.01) | |

(52) U.S. Cl.
CPC ........ *C12N 15/8257* (2013.01); *C07K 14/415* (2013.01); *C07K 14/472* (2013.01); *C07K 14/4717* (2013.01); *C07K 14/505* (2013.01); *C07K 14/75* (2013.01); *C07K 14/775* (2013.01); *C07K 14/805* (2013.01); *C12N 15/52* (2013.01); *A61K 38/012* (2013.01); *A61K 38/1725* (2013.01); *A61K 38/18* (2013.01); *A61K 38/363* (2013.01); *A61K 38/42* (2013.01)

(58) Field of Classification Search
None
See application file for complete search history.

(56) References Cited

U.S. PATENT DOCUMENTS

| 8,802,438 | B2 * | 8/2014 | Rossi | A61P 7/06 |
|---|---|---|---|---|
| | | | | 435/455 |
| 2012/0255069 | A1 * | 10/2012 | Na | C12N 15/67 |
| | | | | 800/288 |
| 2015/0141678 | A1 * | 5/2015 | Payne | C12N 15/113 |
| | | | | 552/544 |
| 2016/0130567 | A1 * | 5/2016 | Chivukula | C07K 14/575 |
| | | | | 424/450 |

FOREIGN PATENT DOCUMENTS

CA  2984402  11/2016

OTHER PUBLICATIONS

Asrani et al, 2018, RNA Biology, 15:756-762.*
Kwok et al, 2015, Biochem. J., 467:91-102.*
United States Patent and Trademark Office, International Search Report and Written Opinion for PCT/US2018/35419, dated Oct. 25, 2018, 15 pages.
Kim, et al., The immediate upstream region of the 50-UTR from the AUG start codon has a pronounced effect on the translational efficiency in *Arabidopsis thaliana*, Nucleic Acids Research, 2013, pp. 485-498, vol. 42, No. 1.
Dansako, et al., 5' Untranslated Region of the HSP18.2 Gene Contributes to Efficient Translation in Plant Cells, J Biosci Bioeng, 2003, pp. 52-58, vol. 95, No. 1.
Gerasymenko, et al., Comparison of effectiveness of 5'-regulatory sequences in transplastomic tobacco chloroplasts, Transgenic Res, 2016, pp. 65-75, vol. 26.
Stoddard, et al., Targeted Mutagenesis in Plant Cells through Transformation of Sequence-Specific Nuclease mRNA, PLOS One, 2016, 10 pages.

* cited by examiner

*Primary Examiner* — Jason Deveau Rosen
(74) *Attorney, Agent, or Firm* — Mintz, Levin, Cohn, Ferris, Glovsky and Popeo, P.C.

(57) ABSTRACT

This invention provides expressible polynucleotides, which can express a target protein or polypeptide. Synthetic mRNA constructs for producing a protein or polypeptide can contain one or more 5' UTRs, where a 5' UTR may be expressed by a gene of a plant. In some embodiments, a 5' UTR may be expressed by a gene of a member of *Arabidopsis* genus. The synthetic mRNA constructs can be used as pharmaceutical agents for expressing a target protein or polypeptide in vivo.

28 Claims, 16 Drawing Sheets
Specification includes a Sequence Listing.

SYNTHESIS AND STRUCTURE OF HIGH POTENCY RNA THERAPEUTICS

SEQUENCE LISTING

This application includes a Sequence Listing submitted electronically as an ASCII file created on Jun. 24, 2018, named ARC4477US_SL.txt, which is 48,891 bytes in size.

BACKGROUND OF THE INVENTION

It has long been difficult to utilize messenger RNA molecules in medicines. Synthetic mRNA can be designed with inherent translational activity for making an active polypeptide or protein, which could be used in various therapeutic strategies. However, the expression of protein involves a number of steps that are localized and/or regulated. Further, plentiful RNase enzymes can degrade mRNA. Moreover, use of a synthetic mRNA requires clinical formulation and delivery to cells. These steps of mRNA delivery, partitioning and dynamics increase the need for potency, stability, and longevity of the synthetic mRNA.

One way to improve the efficacy of mRNA in medicines is to increase the ability of the molecules to be expressed in cells. Control of the characteristics and kinetics of enhanced expression can be used to improve medicinal potency. In addition, structural features of the molecules could be exploited to enhance potency, stability, and longevity of a synthetic mRNA.

For example, increasing the level of a therapeutic moiety in vivo is a significant factor in drug success. Thus, compositions and methods to increase the translation efficiency of an RNA, and specifically increase the amount of a translated polypeptide or protein is a desirable result.

There is an urgent need for methods, molecules, structures and compositions having the ability to be translated to provide active polypeptide and protein therapeutics. Such new molecules having functional cytoplasmic half-life for producing active agents can yield new therapeutic modalities.

What is needed are expressible molecules that have increased expression, stability and/or half-life over a native mRNA, to be used in methods and compositions for producing and delivering an active polypeptide or protein for use in treating or ameliorating a rare disease.

BRIEF SUMMARY OF THE INVENTION

This invention relates to the fields of molecular biology and genetics, as well as to biopharmaceuticals and therapeutics generated from expressible molecules. More particularly, this invention relates to methods, structures and compositions for molecules having the ability to be translated into active polypeptides or proteins, for use in vivo and as therapeutics.

This invention provides structures, compositions and methods for novel molecules having the ability to be translated, which can be used to provide one or more active polypeptides, proteins, or fragments thereof.

Embodiments of the invention include mRNA constructs containing one or more 5' UTR sequences along with one or more 3' UTR sequences.

The mRNA constructs can provide surprisingly high levels of human proteins in mammalian cells and subjects, and are useful as therapeutics.

Additional embodiments of this invention include heterologous mRNA constructs designed to produce a human protein, or fragment thereof, in mammalian cells, wherein such heterologous mRNA constructs may comprise an untranslated region (UTR) from a gene found in a plant species, and a coding region designed to produce a human protein or fragment thereof. The plant species may be a member of the angiosperm family. In some embodiments, the plant species can be a member of the *Arabidopsis* genus.

Embodiments of this invention further contemplate heterologous mRNA constructs designed to produce human protein in mammalian cells, wherein such constructs may comprise a UTR sequence from an *Arapidopsis thaliana* gene.

In certain embodiments, this invention includes heterologous mRNA constructs, which can produce a human protein, or a fragment thereof, in a mammalian cell. A heterologous mRNA construct may comprise a −21 to −1 5'-UTR sequence from an *Arapidopsis thaliana* gene. The 5'-UTR sequence may be followed by a Kozak sequence.

In further embodiments, this invention includes heterologous mRNA constructs designed to produce a human protein, or one or more fragments thereof, in mammalian cells, wherein a construct may comprise a 5' UTR sequence from an *Arapidopsis thaliana* gene. The 5'-UTR sequence may be followed by a Kozak sequence, a human coding sequence, and a 3'-UTR sequence.

This invention provides a range of mRNA constructs, each of which can produce a protein of interest, or one or more fragments thereof. The protein of interest can be any protein, natural, non-natural, or synthetic. In some embodiments, the protein of interest can be a human protein. In further embodiments, the protein may be a fusion protein, or a chimeric protein. In additional embodiments, the protein may be a globular protein, a fibrous protein, a membrane protein, or a disordered protein.

In certain embodiments, this invention includes a heterologous mRNA construct designed to produce a human protein, or one or more fragements thereof, in mammalian cells, where the construct may comprise a coding region designed to express a protein of Table 2, and a 5' UTR derived from a gene expressed by *Arabidopsis thaliana*.

The expressible molecules of this invention can have functional cytoplasmic activity for producing polypeptides or proteins. The peptides and proteins may be active for therapeutic modalities.

The translatable molecules of this invention can have long half-life, particularly in the cytoplasm of a cell. The translatable molecules can be expressible to provide a product that is active for ameliorating, preventing or treating a disease or condition. The disease or condition can be associated with undesirable modulation of protein concentration, or undesirable activity of a protein.

This disclosure provides a range of structures for translatable molecules for producing polypeptides or proteins. In some embodiments, the translatable molecules can have an increased ability to be translated and/or an extended half-life over a native mRNA.

The translatable molecules of this invention can be used in medicines, and for methods and compositions for producing and delivering active polypeptides and proteins. The translatable molecules of this invention can be used to provide polypeptides or proteins in vitro, ex vivo, or in vivo.

In certain aspects, the translatable molecules of this invention can provide high-efficiency expression of a polypeptide or protein, or a fragment thereof. The expression can be in vitro, ex vivo, or in vivo.

In some embodiments, a molecule of this invention can have increased cytoplasmic half-life over a native, mature mRNA that encodes the same polypeptide or protein. The inventive molecules and compositions can provide increased functional cellular activity with respect to a native, mature mRNA.

In further aspects, a translatable molecule of this invention can provide increased activity as a drug agent providing a peptide or protein product, as compared to a native, mature mRNA. A translatable molecule of this invention may reduce the dose level required for efficacious therapy.

In some aspects, this invention provides processes for making an RNA including steps for providing a DNA molecule that can be transcribed to provide the RNA. In the DNA, certain codons in an open reading frame of the DNA can be replaced with alternative codons while preserving codon assignment. The DNA molecule can be transcribed in the presence of nucleoside triphosphates, a 5' cap, and one or more chemically-modified nucleoside triphosphates to form a product mixture. An RNA can be isolated and purified from the mixture. The RNA may contain natural and chemically-modified nucleotides.

In certain aspects, this invention provides methods for synthesis of an RNA. Processes for making an RNA can include steps for providing a DNA molecule that can be transcribed to provide the RNA. In the DNA, certain adenosine nucleotides in an open reading frame of the DNA can be replaced with non-adenosine nucleotides while preserving codon assignment. The DNA may further comprise a promoter for transcribing the non-coding strand. The DNA molecule can be transcribed in the presence of nucleoside triphosphates, a 5' cap, and one or more chemically-modified nucleoside triphosphates to form a product mixture. An RNA can be isolated and purified from the mixture. The RNA may contain natural and chemically-modified nucleotides.

The RNA product molecules made by a process of this invention can have functional cytoplasmic half-life for producing polypeptides and proteins. The peptides and proteins can be active for therapeutic modalities, as well as for use in vaccines and immunotherapies.

The RNA molecules made by a process of this invention can be translatable messenger molecules, which can have long half-life, particularly in the cytoplasm of a cell. The longer duration of the translatable messenger molecules of this invention can be significant for providing a translation product that is active for ameliorating, preventing or treating disease.

This disclosure provides a range of structures for translatable molecules having increased specific activity and/or lifetime over a native mRNA. The translatable molecules of this invention can be used in medicines, and for methods and compositions for producing and delivering active peptides and proteins.

This invention further provides processes for making translatable RNA molecules having enhanced properties for providing and delivering polypeptides and proteins.

Embodiments of this disclosure can provide a wide range of novel, translatable messenger RNA molecules. The translatable messenger molecules can contain various chemically modified nucleotides, or monomers that are unlocked nucleomonomers (UNA monomers), among others.

The translatable molecules of this invention can be used to provide polypeptides or proteins in vitro, ex vivo, or in vivo.

The translatable messenger molecules of this invention can be designed to provide high-efficiency expression of an expression product, polypeptide, protein, or fragment thereof.

In some embodiments, the messenger molecules of this invention have increased cytoplasmic half-life over a native, mature mRNA that provides the same expression product. The structures and compositions of this invention can provide increased functional half-life with respect to native, mature mRNAs.

In further aspects, a translatable messenger molecule of this invention can provide increased activity as a drug providing a polypeptide or protein product, as compared to a native, mature mRNA. In some embodiments, a translatable molecule can reduce the expected dose level that would be required for efficacious therapy.

In additional embodiments, this invention provides methods for ameliorating, preventing or treating a disease or condition in a subject comprising administering to the subject a composition containing a translatable molecule of this invention.

The disease or condition can be a rare disease, a chronic disease, a liver disease, or a cancer, among others.

In certain embodiments, this invention provides methods for producing a polypeptide or protein in vivo, by administering to a mammal a composition containing a translatable RNA molecule. The polypeptide or protein may be deficient in a disease or condition of a subject or mammal.

Examples of polypeptides and proteins of this disclosure include human EPO, human Factor IX, human alpha-1-antitrypsin, human CFTR, human ASL, human NIS, and human hepcidin, among others.

This invention further provides methods for producing a therapeutic polypeptide or protein in vitro, or in vivo, by transfecting a cell with a translatable molecule. The polypeptide or protein can be deficient in a disease or condition of a subject or mammal.

Embodiments of this invention include the following:

A synthetic mRNA construct for producing a protein or polypeptide, the mRNA construct comprising one or more 5' UTRs. The one or more 5' UTRs can be expressed by a gene of a plant, or expressed by a gene of a member of *Arabidopsis* genus. The one or more 5' UTRs may be expressed by a gene of *Arapidopsis thaliana*.

In some embodiments, the one or more 5' UTRs can expressed by a gene of *Arapidopsis thaliana*, and the one or more 3' UTRs can be selected from the group of Alanine aminotransferase 1, ARC3-2, Human alpha globin, Human antithrombin, Human apolipoprotein E, Human beta globin, Human complement C3, Human Fibrinogen alpha chain, Human growth factor, Human haptoglobin, Human hepcidin, MALAT, Mouse Albumin, Mouse beta globin, and *Xenopus* beta globin.

In certain embodiments, a 5' UTR may comprise a −21 to −1 sequence of a 5' UTR expressed by a gene of *Arapidopsis thaliana*, or a 5' UTR expressed by AT1G58420.

The one or more 3' UTRs may be expressed by a mammalian gene or a human gene. In some embodiments, the one or more 5' UTRs may be selected from the group of A1G, hALB, mBG, and SynK, and the one or more 3' UTRs may be any natural or non-natural 3'UTRs.

A synthetic mRNA construct of this invention may comprise a 5' cap, one or more 5' UTRs, a coding sequence for encoding the protein or polypeptide, one or more 3' UTRs, and a poly(A) or poly(C) tail.

In some embodiments, a synthetic mRNA construct may comprise a coding sequence for encoding a rare disease protein of Table 2, a 5' UTR expressed by AT1G58420, and a Kozak sequence.

In certain embodiments, an mRNA construct may comprise a coding sequence for encoding the protein or polypeptide, wherein the coding sequence is at least 50% identical to a portion of a reference mRNA sequence, wherein the reference mRNA sequence is a human wild type mRNA sequence.

In further embodiments, the protein or polypeptide may be at least 85% identical to a portion of a reference protein, wherein the reference protein is a human wild type protein.

In other embodiments, the protein or polypeptide can be at least 85% identical to a portion of a reference protein, wherein the reference protein is a human rare disease protein.

A synthetic mRNA construct of this invention may be at least 85% identical to a portion of a reference protein, wherein the reference protein is ornithine transcarbamylase.

In a synthetic mRNA construct of this invention, the expressed protein or polypeptide may be natural or non-natural, or can be an antibody or antibody fragment, or an immunogen or toxoid for use in a vaccine, or a fusion protein, or a globular protein, a fibrous protein, a membrane protein, or a disordered protein. In certain embodiments, the protein may be a human protein, or a fragment thereof, or be deficient in a rare human disease.

A synthetic mRNA construct may have a coding sequence for encoding the protein or polypeptide having alternative codons as compared to a native human protein or polypeptide. In certain embodiments, the coding sequence for encoding the protein or polypeptide may have a high codon adaptation index. In further embodiments, the coding sequence for encoding the protein or polypeptide may have reduced uridine content as compared to a native human mRNA.

Embodiments of this invention contemplate synthetic mRNA constructs having from 50 to 15,000 nucleotides. A synthetic mRNA construct may comprises one or more chemically-modified nucleotides.

A synthetic mRNA construct may have at least 50% increased translation efficiency in vivo as compared to a native mRNA.

This invention further encompasses DNA templates for making an mRNA construct above by in vitro transcription.

This invention includes compositions containing an mRNA construct above and a pharmaceutically acceptable carrier. The carrier may comprise a transfection reagent, a nanoparticle, or a liposome. A nanoparticle may include a lipid nanoparticle.

In some embodiments, a composition of this invention may include lipid nanoparticles comprising a thiocarbamate or carbamate-containing lipid molecule.

This invention further contemplates methods for ameliorating, preventing or treating a disease or condition in a subject in need thereof, by administering to the subject a composition containing an mRNA construct. A composition may be for use in medical therapy, or for use in preparing or manufacturing a medicament for preventing, ameliorating, delaying onset or treating a disease or condition in a subject in need.

In some aspects, this invention includes processes for making an expressible polynucleotide, by providing a DNA template that is transcribable to provide the polynucleotide, wherein the DNA template comprises a non-coding strand comprising: a promoter; a sequence that is transcribable to provide a 5' untranslated region expressed by a gene of *Arapidopsis thaliana*; a non-coding region that is transcribable to provide a coding region of the expressible polynucleotide; and a sequence that is transcribable to provide a 3' untranslated region selected from the group of Alanine aminotransferase 1, ARC3-2, Human alpha globin, Human antithrombin, Human apolipoprotein E, Human beta globin, Human complement C3, Human Fibrinogen alpha chain, Human growth factor, Human haptoglobin, Human hepcidin, MALAT, Mouse Albumin, Mouse beta globin, and *Xenopus* beta globin; transcribing the DNA molecule in the presence of nucleoside triphosphates to form a product mixture; and purifying the product mixture to isolate the expressible polynucleotide.

BRIEF DESCRIPTION OF THE DRAWINGS

FIG. 1 shows the normalized expressions for 24 hrs as compared to 48 hrs. Using translatable molecules of this invention, expression for human erythropoietin (hEPO) was surprisingly increased over control by more than 100%.

FIG. 2 shows the area under the curve (AUC) for expression, as compared to expression at 48 hrs. Using translatable molecules of this invention, expression for human erythropoietin (hEPO) was surprisingly increased over control by more than 100%.

FIG. 3 shows the area under the curve (AUC) for expression, as compared to expression at 24 hrs. Using translatable molecules of this invention, expression for human erythropoietin (hEPO) was surprisingly increased over control by more than 100%.

DETAILED DESCRIPTION OF THE INVENTION

Figure 1:
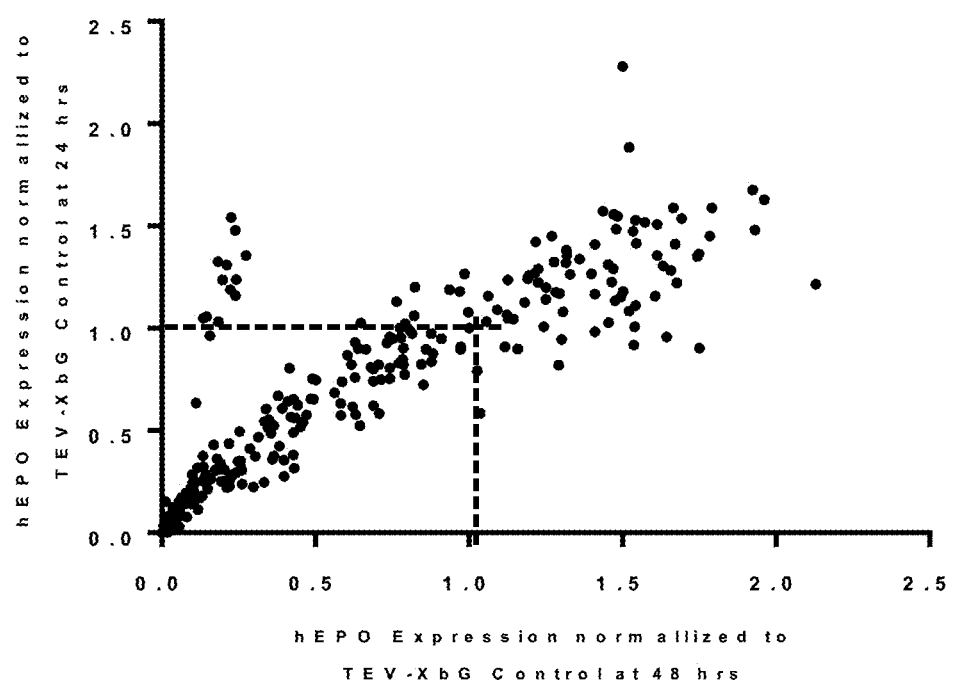
FIG. 1 shows the results of enhanced expression control for human erythropoietin (hEPO) in vitro using translatable molecules of this invention. hEPO mRNAs were synthesized in vitro using T7RNA polymerase-mediated DNA-dependent RNA transcription, where UTP was substituted with 100% $N^1$-methylpseudouracil (N1MPU), using a linearized template for each UTR combination. mRNAs were synthesized having all combinations of different 5'UTR and 3'UTR of Table 7. The mRNAs were transfected into Hepa1-6 cells, a mouse hepatoma cell line derived from the BW7756 tumor that arose in a C57L mouse, using MESSENGER MAX transfection reagents. The cell culture medium was collected at 24, 48, and 72 hrs after transfection. hEPO protein production was detected using ELISA at 24, 48, and 72 hrs. The hEPO expressions for each time point were normalized using hEPO having 5'UTR of TEV and 3'UTR of XbG as a control.

This invention provides a range of novel agents and compositions to be used for therapeutic applications. The molecules and compositions of this invention can be used for ameliorating, preventing or treating a disease, including, for example, rare diseases, chronic diseases, liver disease, and cancer, among others.

In some embodiments, this invention encompasses synthetic, purified, and/or isolated, translatable polynucleotide molecules for expressing a human polypeptide, protein, or fragment thereof, wherein the polynucleotide molecules comprise natural and chemically-modified nucleotides, and encode the polypeptide, protein, or fragment.

Embodiments of this invention can provide nucleic acids that, when introduced into cells, can have improved properties such as increased expression levels, reduced immune response, and increased lifetime as compared to wild type nucleic acids.

In some embodiments, a translatable molecule of this invention can be a modified mRNA. A modified mRNA can encode one or more biologically active peptides, polypeptides, or proteins. A modified mRNA can comprise one or more modifications as compared to wild type mRNA. Modifications of an mRNA may be located in any region of the molecule, including a coding region, an untranslated region, or a cap or tail region.

As used herein, the term "translatable" may be used interchangeably with the term "expressible." These terms can refer to the ability of polynucleotide, or a portion thereof, to provide a polypeptide, by transcription and/or translation events in a process using biological molecules, or in a cell, or in a natural biological setting. In some settings, translation is a process that can occur when a ribosome creates a polypeptide in a cell. In translation, a messenger RNA (mRNA) can be decoded by a ribosome to produce a specific amino acid chain, or polypeptide. A translatable polynucleotide can provide a coding sequence region (usually, CDS), or portion thereof, that can be processed to provide a polypeptide, protein, or fragment thereof.

A translatable oligomer or polynucleotide of this invention can provide a coding sequence region, and can comprise various untranslated sequences, such as a 5' cap, a 5' untranslated region (5' UTR), a 3' untranslated region (3' UTR), and a tail region.

In some embodiments, a translatable molecule may include a 5' cap, a 5' UTR, a translation initiation sequence such as a Kozak sequence, a CDS, a 3' UTR, and a tail region.

In additional embodiments, a human CDS may comprise a codon-modified sequence.

A polynucleotide of this invention may contain sequences in addition to the coding sequence (CDS). Additional sequences may be untranslated sequences, for example, sequences that are not converted to protein by a host cell. Untranslated sequences can include a 5' cap, a 5' untranslated region (5' UTR), a 3' untranslated region (3' UTR), and a tail region.

A tail region may be, for example, a polyA or polyC tail region.

In some embodiments, a translatable molecule of this invention may comprise a coding sequence that is at least 40%, 50%, 60%, 70%, 80%, 85%, 90%, 91%, 92%, 93%, 94%, 95%, 96%, 97%, 98%, or 99% or more identical to a portion of a reference mRNA sequence, such as a human wild type mRNA sequence. In some embodiments, a reference mRNA sequence can be a rare disease mRNA.

In some embodiments, a translatable molecule of this invention may comprise a coding sequence that has one, or two, or three, or four, or five, or six, or seven, or eight, or nine, or ten, or fifteen, or twenty or more synonymous or non-synonymous codon replacements as compared to a reference mRNA sequence, such as a human wild type mRNA sequence.

In some embodiments, a non-coding polynucleotide template sequence that is transcribable to provide a translatable molecule of this invention, when transcribed may provide a translatable molecule that is at least 40%, or 50%, or 60%, or 70%, or 80%, or 85%, or 90%, or 91%, or 92%, or 93%, or 94%, or 95%, or 96%, or 97%, or 98%, or 99% identical to a portion of a reference mRNA sequence, such as a human wild type mRNA sequence.

In some embodiments, a non-coding polynucleotide template sequence that is transcribable to provide a translatable molecule of this invention, when transcribed may provide a translatable molecule that has one, or two, or three, or four, or five, or six, or seven, or eight, or nine, or ten, or fifteen, or twenty or more synonymous or non-synonymous codon replacements as compared to a reference mRNA sequence, such as a human wild type mRNA sequence.

In some embodiments, a translatable molecule of this invention may be used to express a polypeptide that is at least 80%, 85%, 90%, 91%, 92%, 93%, 94%, 95%, 96%, 97%, 98%, 99% or more identical to a portion of a reference polypeptide or protein sequence, such as a human wild type protein sequence. In some embodiments, a reference polypeptide or protein sequence can be a rare disease protein sequence.

In some embodiments, a translatable molecule of this invention may be used to express a polypeptide that has one, or two, or three, or four, or five, or six, or seven, or eight, or nine, or ten, or fifteen, or twenty or more variant amino acid residues as compared to a reference polypeptide or protein sequence, such as a human wild type protein sequence.

In some embodiments, a translatable molecule of the invention may encode a fusion protein comprising a full length, or fragment or portion of a native human protein fused to another sequence, for example by N or C terminal fusion. In some embodiments, the N or C terminal sequence can be a signal sequence or a cellular targeting sequence.

A translatable molecule may comprise one or more LNA monomers.

The translatable molecules of this invention can be used in methods for ameliorating, preventing or treating a disease or condition associated with a polypeptide or protein. The translation efficiency of a translatable molecule of this invention can be increased as compared to a native mRNA.

A translatable molecule of this invention, which has one or more chemically modified nucleotides, can have reduced immunogenicity as compared to a native mRNA, or a synthetic mRNA with the same sequence and containing only natural nucleotides.

In some embodiments, a translatable molecule of this invention can have reduced immunogenicity as compared to a native mRNA. A translatable molecule can be less immunogenic than a synthetic RNA molecule with the same sequence and containing only natural nucleotides. Some methods for measuring immunogenicity include secretion of cytokines, for example, IL-12, IFN-a, TNF-a, RANTES, MIP-1a or b, IL-6, IFN-b, IFN-g or IL-8, and measuring expression of DC activation markers, for example, CD83, HLA-DR, CD80 and CD86.

In certain embodiments, the immunogenicity of a translatable molecule can be reduced by 2-fold, or 3-fold, or 5-fold, or 10-fold, or 20-fold, or more, as compared to a native mRNA, or as compared to a synthetic RNA molecule with the same sequence and containing only natural nucleotides.

A translatable molecule of this invention, which has one or more chemically modified nucleotides, can have increased translation efficiency as compared to a native mRNA, or a synthetic mRNA with the same sequence and containing only natural nucleotides.

In certain embodiments, the translation efficiency of a translatable molecule can be increased by 30%, or 50%, or 70%, or 100%, or 150%, or 200%, or more, as compared to a native mRNA, or as compared to a synthetic RNA molecule with the same sequence and containing only natural nucleotides. The translation efficiency may be performed in vitro, ex vivo, or in vivo.

mRNA Constructs

In some aspects, an mRNA construct of this invention can be homologous or heterologous. As used herein, the term "homologous mRNA construct" is a class of expressible polynucleotides, where the sequences of the polynucleotides are derived from a human gene.

As used herein, the term "heterologous mRNA construct" is a class of expressible polynucleotides wherein at least one of the untranslated region sequences of the polynucleotide is derived from a non-human gene, and the coding region of such construct is derived from a human gene.

This invention provides methods and compositions for novel molecules having the ability to be translated, which can be used to provide one or more active polypeptides and proteins, or fragments thereof. Embodiments of the invention can be directed to mRNA constructs comprising 5'UTR sequences in combination with 3'UTR sequences, not previously used in the context of heterologous mRNA constructs, to efficiently produce human proteins, or fragments thereof, in mammalian cells or animals.

Additional embodiments of this invention include heterologous mRNA constructs designed to produce a human protein, or fragment thereof, in mammalian cells, wherein such heterologous mRNA constructs may comprise an untranslated region (UTR) from a gene found in a plant species, and a coding region designed to produce a human protein or fragment thereof. The UTR can be a 5' UTR or a 3' UTR. The plant species may be a member of the angiosperm family.

In further embodiments, the plant species can be a member of the *Arabidopsis* genus.

Embodiments of this invention further contemplate heterologous mRNA constructs designed to produce human protein in mammalian cells, wherein such constructs may comprise a UTR sequence from an *Arapidopsis thaliana* gene.

In some aspects of this invention, a UTR sequence can be a 5' UTR or 3' UTR.

In certain embodiments, this invention includes heterologous mRNA constructs, which can produce a human protein, or a fragment thereof, in a mammalian cell. A heterologous mRNA construct may comprise a −21 to −1 5'-UTR sequence from an *Arapidopsis thaliana* gene. The 5'-UTR sequence may be followed by a Kozak sequence.

In further embodiments, this invention includes heterologous mRNA constructs designed to produce a human protein, or one or more fragments thereof, in mammalian cells, wherein a construct may comprise a 5' UTR sequence from an *Arapidopsis thaliana* gene. The 5'-UTR sequence may be followed by a Kozak sequence, a human coding sequence, and a 3'-UTR sequence.

This invention provides a range of mRNA constructs, each of which can produce a protein of interest, or one or more fragments thereof. The protein of interest can be any protein, natural, non-natural, or synthetic. In some embodiments, the protein of interest can be a human protein. In further embodiments, the protein may be a fusion protein, or a chimeric protein. In additional embodiments, the protein may be a globular protein, a fibrous protein, a membrane protein, or a disordered protein.

In certain embodiments, this invention includes a heterologous mRNA construct designed to produce a human protein, or one or more fragments thereof, in mammalian cells, where the construct may comprise a coding region designed to express a protein of Table 2, and a 5' UTR derived from a gene expressed by *Arabidopsis thaliana*.

In further embodiments, this invention includes a heterologous mRNA construct designed to produce a human protein, or one or more fragments thereof, in mammalian cells, where the construct may comprise a coding region designed to express a protein of Table 2, and a −21 to −1 5'-UTR sequence from an *Arapidopsis thaliana* gene.

In additional embodiments, this invention includes a heterologous mRNA construct designed to produce a human protein, or one or more fragements thereof, in mammalian cells, where the construct may comprise a coding region of a protein of Table 2, and a 5'-UTR of AT1G58420. In another embodiment, this invention includes a heterologous mRNA construct designed to produce a human protein, or one or more fragments thereof, in mammalian cells, where the construct may comprise a coding region of a protein of Table 2, a 5'-UTR of AT1G58420, and a Kozak sequence.

Embodiments of this invention further include a heterologous mRNA construct designed to produce a human protein in mammalian cells, where the construct may comprise a coding region encoding a human protein of Table 2, and a 5' UTR derived from a gene expressed by *Arabidopsis thaliana*.

In certain embodiments, this invention includes a heterologous mRNA construct designed to produce human protein in mammalian cells, where the construct may comprise a coding region of a human protein of Table 2, and a −21 to −1 5'-UTR sequence from an *Arapidopsis thaliana* gene.

In additional embodiments, this invention includes a heterologous mRNA construct designed to produce human protein in mammalian cells, where the construct may comprise a coding region of a human protein of Table 2, a −21 to −1 5'-UTR sequence from an *Arapidopsis thaliana* gene, and a Kozak sequence.

In further embodiments, this invention includes a heterologous mRNA construct designed to produce human protein in mammalian cells, where the construct may comprise a coding region of a human protein of Table 2, and a −5 to −1 5'-UTR sequence from an *Arapidopsis thaliana* gene.

In some embodiments, this invention includes a heterologous mRNA construct designed to produce human protein in mammalian cells, where the construct may comprise a coding region of a human protein of Table 2, a −5 to −1 5'-UTR sequence from an *Arapidopsis thaliana* gene, and a Kozak sequence.

In additional embodiments, this invention includes a heterologous mRNA construct designed to produce human protein in mammalian cells, where the construct may comprise a coding region of a human protein of Table 2, and a 5'-UTR of AT1G58420.

In further embodiments, this invention includes a heterologous mRNA construct designed to produce a human protein in mammalian cells, where the construct may comprise a coding region of a human protein of Table 2, a 5' UTR of AT1G58420, and a Kozak sequence.

In some aspects, this invention includes heterologous mRNA constructs, where a construct may contain a coding region that encodes a native human protein, or a fragment thereof, and where the coding region may contain alternative codons relative to the native mRNA that expresses the native human protein.

In some embodiments, this invention includes heterologous mRNA constructs, where a construct may contain a coding region that encodes a native human protein, or a fragment thereof, and where the coding region may contain alternative codons relative to the native mRNA that expresses the native human protein, and the coding region may have a high codon adaptation index. A heterologous mRNA construct of this invention may have a coding region having a high codon adaptation index.

In some embodiments, an mRNA construct of this invention will contain one or more 5' UTRs selected from the group of Human Albumin, AT1G58420, Human ApoE, Mouse beta globin, TEV, Truncated Rossi, and SynK.

In some embodiments, an mRNA construct of this invention will contain one or more 3' UTRs selected from the group of Mouse Albumin, Human alpha globin, ARC3-2, Alanine aminotransferase 1, Human beta globin, Human apolipoprotein E, Human antithrombin, *Xenopus* beta globin, Human growth factor, Mouse beta globin, and Human fibrinogen alpha chain.

In some embodiments, an mRNA construct of this invention will have a 5' UTR selected from the group of Human Albumin, AT1G58420, Human ApoE, Mouse beta globin, TEV, Truncated Rossi, and SynK, and a 3' UTR selected from the group of Mouse Albumin, Human alpha globin, ARC3-2, Alanine aminotransferase 1, Human beta globin, Human apolipoprotein E, Human antithrombin, *Xenopus* beta globin, Human growth factor, Mouse beta globin, and Human fibrinogen alpha chain.

In some embodiments, an mRNA construct of this invention will contain one or more 5' UTRs selected from the group of AT1G, HHV, Human Albumin, Mouse beta globin, SynK, TEV, and Truncated Rossi.

In some embodiments, an mRNA construct of this invention will contain one or more 3' UTRs selected from the group of Alanine aminotransferase 1, ARC3-2, Human alpha globin, Human antithrombin, Human apolipoprotein E, Human beta globin, Human complement C3, Human Fibrinogen alpha chain, Human growth factor, Human haptoglobin, Human hepcidin, MALAT, Mouse Albumin, Mouse beta globin, and *Xenopus* beta globin.

In some embodiments, an mRNA construct of this invention will contain a 5' UTR selected from the group of AT1G, HHV, Human Albumin, Mouse beta globin, SynK, TEV, and Truncated Rossi, and a 3' UTR selected from the group of Alanine aminotransferase 1, ARC3-2, Human alpha globin, Human antithrombin, Human apolipoprotein E, Human beta globin, Human complement C3, Human Fibrinogen alpha chain, Human growth factor, Human haptoglobin, Human hepcidin, MALAT, Mouse Albumin, Mouse beta globin, and *Xenopus* beta globin.

In some embodiments, an mRNA construct of this invention will contain one or more 5' UTRs selected from the group of Human Albumin, AT1G58420, Truncated Rossi, Mouse beta globin, Human ApoE, and HHV.

In some embodiments, an mRNA construct of this invention will contain one or more 3' UTRs selected from the group of Mouse Albumin, Human alpha globin, ARC3-2, Alanine aminotransferase 1, Human apolipoprotein E, *Xenopus* beta globin, Human antithrombin, Human growth factor, Human beta globin, Human fibrinogen alpha chain, Human complement C3, MALAT, Human hepcidin, and Mouse beta globin.

In some embodiments, an mRNA construct of this invention will contain a 5' UTR selected from the group of Human Albumin, AT1G58420, Truncated Rossi, Mouse beta globin, Human ApoE, and HHV, and a 3' UTR selected from the group of Mouse Albumin, Human alpha globin, ARC3-2, Alanine aminotransferase 1, Human apolipoprotein E, *Xenopus* beta globin, Human antithrombin, Human growth factor, Human beta globin, Human fibrinogen alpha chain, Human complement C3, MALAT, Human hepcidin, and Mouse beta globin.

In some embodiments, an mRNA construct of this invention will contain one or more 5' UTRs selected from the group of SynK, AT1G58420, Human Albumin, and Mouse beta globin.

In some embodiments, an mRNA construct of this invention will contain one or more 3' UTRs selected from the group of Human alpha globin, ARC3-2, Human beta globin, Alanine aminotransferase 1, Human growth factor, Human antithrombin, MALAT, Human apolipoprotein E, Mouse beta globin, *Xenopus* beta globin, Human haptoglobin, and Mouse Albumin.

In some embodiments, an mRNA construct of this invention will contain a 5' UTR selected from the group of SynK, AT1G58420, Human Albumin, and Mouse beta globin, and a 3' UTR selected from the group of Human alpha globin, ARC3-2, Human beta globin, Alanine aminotransferase 1, Human growth factor, Human antithrombin, MALAT, Human apolipoprotein E, Mouse beta globin, *Xenopus* beta globin, Human haptoglobin, and Mouse Albumin.

In some embodiments, an mRNA construct of this invention will contain a 5' UTR and a 3' UTR as shown in Table 1.

TABLE 1

Examples of mRNA constructs and 5'UTR-3'UTR combination sequences

| mRNA | 5' UTR | 3' UTR |
|---|---|---|
| 132 | A1G | ARC3-2 |
| 122 | A1G | hAG |
| 166 | hALB | hBG |
| 169 | hALB | mALB |
| 121 | A1G | mALB |
| 138 | SynK | hAG |
| 120 | A1G | hGH |
| 129 | A1G | Alanine amino transferase |
| 180 | hALB | ARC3-2 |
| 176 | hALB | hApolipoprotein E |
| 124 | A1G | hAntithrombin |
| 177 | hALB | Alanine amino transferase |
| 196 | mBG | ARC3-2 |
| 184 | mBG | hGH |
| 192 | mBG | hApolipoprotein E |
| 119 | A1G | XBG |
| 116 | TEV | ARC3-2 |
| 170 | hALB | hAG |
| 168 | hALB | hGH |
| 106 | TEV | hAG |

In some embodiments, an mRNA construct of this invention will contain one or more 5' UTRs selected from the group of A1G, hALB, mBG, and SynK.

As used herein, A1G is AT1G58420 (Table 3, SEQ ID NO:10), which is derived from *Arabidopsis thaliana* Uncharacterized conserved protein.

As used herein, ARC3-2 refers to human growth hormone 1 (Table 5, SEQ ID NO:91). *Homo sapiens* growth hormone 1 (GH1), transcript variant 1, mRNA, NCBI Reference Sequence: NM_000515.4.

hALB is human albumin.

mBG is mouse beta globin.

hAG is human alpha globin.

SynK is a potassium channel in the genome of the cyanobacterium *Synechocystis* sp. PCC6803.

*Arabidopsis thaliana* Uncharacterized conserved protein UCP031279 mRNA is NCBI Reference Sequence: NM_104622.3.

*Homo sapiens* ornithine carbamoyltransferase (OTC), mRNA is NCBI Reference Sequence: NM_000531.5.

In some embodiments, an mRNA construct of this invention will contain one or more 5' UTRs selected from the group of AIG, hALB, mBG, and SynK, and any natural or non-natural 3'UTR.

In some aspects, this invention provides processes for making an RNA including steps for providing a DNA molecule that can be transcribed to provide the RNA. In the DNA, certain codons in an open reading frame of the DNA can be replaced with alternative codons while preserving codon assignment. The DNA molecule can be transcribed in the presence of nucleoside triphosphates, a 5' cap, and one or more chemically-modified nucleoside triphosphates to form a product mixture. An RNA can be isolated and purified from the mixture. The RNA may contain natural and chemically-modified nucleotides.

In some embodiments, this invention includes a process for making an expressible polynucleotide, the process comprising:

providing a DNA template that is transcribable to provide the polynucleotide, wherein the DNA template comprises a non-coding strand comprising:
- a promoter;
- a sequence that is transcribable to provide a 5' untranslated region independently selected from Table 4;
- a non-coding region that is transcribable to provide a coding region of the expressible polynucleotide; and
- a sequence that is transcribable to provide a 3' untranslated region independently selected from Table 5;

transcribing the DNA molecule in the presence of nucleoside triphosphates to form a product mixture;

purifying the product mixture to isolate the expressible polynucleotide.

In further embodiments, this invention includes a DNA template that is transcribable to provide an expressible polynucleotide, wherein the DNA template comprises a non-coding strand comprising:
- a promoter;
- a region that is transcribable to provide a 5' untranslated region selected from Table 4;
- a non-coding region that is transcribable to provide a coding region of the expressible polynucleotide; and
- a region that is transcribable to provide a 3' untranslated region selected from Table 5.

This invention further encompasses a translatable RNA that is a transcription product of the template above.

In certain embodiments, this invention includes a process for making an expressible polynucleotide, the process comprising:

providing a DNA template that is transcribable to provide the polynucleotide, wherein the DNA template comprises a non-coding strand comprising:
- a promoter;
- a sequence that is transcribable to provide a 5' untranslated region independently selected from Table 4;
- a non-coding region that is transcribable to provide a coding region of the expressible polynucleotide, wherein deoxyadenosine nucleotides in a modified portion of the non-coding strand that is transcribable to provide an open reading frame in the expressible polynucleotide are replaced with non-adenosine nucleotides while preserving codon assignment; and
- a sequence that is transcribable to provide a 3' untranslated region independently selected from Table 5;

transcribing the DNA molecule in the presence of nucleoside triphosphates to form a product mixture;

purifying the product mixture to isolate the expressible polynucleotide.

mRNA Construct Structures

The molecules of this invention can be translatable messenger RNA molecules. In some embodiments, the RNA agents can have long half-life, particularly in the cytoplasm. The long duration messenger molecules can be used for ameliorating, preventing, or treating disease associated with a polypeptide or protein level in a subject.

As used herein, the term "half-life" is the time required for a quantity such as nucleic acid or protein concentration or activity to fall to half of its value as measured at the beginning of a time period.

A product RNA can be a translatable molecule that contains natural and chemically modified nucleotides, and enhanced translational efficiency and resulting activity.

This invention provides a range of translatable molecules that are surprisingly translatable to provide active peptide or protein, in vitro and in vivo.

The translatable structures and compositions can have increased translational activity and cytoplasmic half-life. In these embodiments, the translatable structures and compositions can provide increased functional half-life in the cytoplasm of mammalian cells over native mRNA molecules. The inventive translatable molecules can have increased half-life of activity with respect to a corresponding native mRNA.

This invention provides a range of translatable molecules that are useful for providing therapeutic effects because of their longevity of activity in providing an expressed peptide or protein.

In some embodiments, a translatable molecule can be from about 200 to about 12,000 monomers in length, or more. In certain embodiments, a translatable molecule can be from 200 to 12,000 monomers in length, or 200 to 10,000 monomers, or 200 to 8,000 monomers, or 200 to 6000 monomers, or 200 to 5000 monomers, or 200 to 4000 monomers, or 200 to 3600 monomers, or 200 to 3200 monomers, or 200 to 3000 monomers, or 200 to 2800 monomers, or 200 to 2600 monomers, or 200 to 2400 monomers, or 200 to 2200 monomers, or 600 to 3200 monomers, or 600 to 3000 monomers, or 600 to 2600 monomers.

In some embodiments, a translatable molecule can be from about 200 to about 12,000 bases in length, or more. In certain embodiments, a translatable molecule can be from 200 to 12,000 bases in length, or 200 to 10,000 bases, or 200 to 8,000 bases, or 200 to 6000 bases, or 200 to 5000 bases, or 200 to 4000 bases, or 200 to 3600 bases, or 200 to 3200 bases, or 200 to 3000 bases, or 200 to 2800 bases, or 200 to 2600 bases, or 200 to 2400 bases, or 200 to 2200 bases, or 600 to 3200 bases, or 600 to 3000 bases, or 600 to 2600 bases.

This invention provides a range of translatable molecules, which can contain one or more UNA monomers, and a number of nucleic acid monomers, wherein the translatable molecule can be translated to express a polypeptide or protein. Some UNA monomers are described in WO/2016/070166. In some embodiments, this invention includes a range of translatable molecules, which may contain one or more UNA monomers in a tail region, wherein the translatable molecule can be translated to express a polypeptide or protein. In some embodiments, a translatable molecule may comprise a 3' polyA tail containing one or more UNA monomers. In some embodiments, a 3' polyA tail may contain 2, 3, 4, 5, 10, or more UNA monomers.

The molecules of this invention can be translatable molecules containing RNA and/or UNA monomers. These translatable molecules can have long half-life, particularly in the cytoplasm. The long duration translatable molecules can be used for ameliorating, preventing, or treating disease associated with reduced presence or function of a polypeptide or protein in a subject.

A translatable molecule of this invention is expressible to provide one or more active polypeptides or proteins, or fragments thereof.

The translatable structures and compositions can have increased translational activity or cytoplasmic half-life. In these embodiments, the translatable structures and compositions can provide increased functional half-life in the cytoplasm of mammalian cells, as compared to a native mRNA.

In some embodiments, a cell can be a eukaryotic cell, a mammalian cell, or a human cell.

A translatable molecule of this invention can incorporate a region that enhances the translational efficiency of the molecule. A translational enhancer region can be incorporated into the structure of a translatable molecule to increase peptide or protein yields. A translatable molecule containing a translation enhancer region can provide increased production of peptide or protein.

In some embodiments, a translation enhancer region can comprise, or be located in a 5' or 3' untranslated region of a translatable molecule.

In some embodiments, a translatable molecule can contain from 1 to about 800 locked nucleic acid (LNA) monomers. In certain embodiments, a translatable molecule can contain from 1 to 600 LNA monomers, or 1 to 100 LNA monomers, or 1 to 30 LNA monomers, or 1 to 12 LNA monomers.

A translatable molecule of this invention may comprise a 5' cap, a 5' untranslated region of monomers, a coding region of monomers, a 3' untranslated region of monomers, and a tail region of monomers.

A translatable molecule of this invention may comprise regions of sequences or structures that are operable for translation in a cell, or which have the functionality of regions of an mRNA including, for example, a 5' cap, a 5' untranslated region, a coding region, a 3' untranslated region, and a polyA or polyC tail.

This invention further contemplates methods for delivering one or more vectors comprising one or more translatable molecules to a cell. In further embodiments, the invention also contemplates delivering or one or more translatable molecules to a cell.

In some embodiments, one or more translatable molecules can be delivered to a cell, in vitro, ex vivo, or in vivo. Viral and non-viral transfer methods as are known in the art can be used to introduce translatable molecules in mammalian cells. Translatable molecules can be delivered with a pharmaceutically acceptable vehicle, or for example, with nanoparticles or liposomes.

In some embodiments, translatable structures and compositions of this invention can reduce the number and frequency of transfections required for cell-fate manipulation in culture as compared to utilizing native compositions.

In further aspects, this invention provides increased activity for translatable molecules as active agent, as compared to utilizing a native mRNA.

In some aspects, this invention can provide translatable molecules that may reduce the cellular innate immune response, as compared to that induced by a native nucleic acid, polypeptide or protein.

This invention can provide synthetic translatable molecules that are refractory to deadenylation as compared to native molecules.

In certain embodiments, this invention can provide synthetic translatable molecules with increased specific activity and longer functional half-life as compared to native molecules. The synthetic translatable molecules of this invention can provide increased levels of ectopic protein expression. When expressing a translatable molecule using a vector, cellular-delivery can be at increased levels, and cytotoxic innate immune responses can be restrained so that higher levels of ectopic protein expression can be achieved. The translatable molecules of this invention can have increased specific activity and longer functional half-life than native mRNAs.

In certain aspects, a translatable molecule may have a number of mutations relative to a native mRNA.

In further embodiments, this invention can provide translatable molecules having cleavable delivery and targeting moieties attached at a 3' end and/or a 5' end.

In general, the specific activity for a synthetic translatable molecule delivered by transfection can be viewed as the number of molecules of protein expressed per delivered transcript per unit time.

As used herein, translation efficiency refers to a measure of the production of a protein or polypeptide by translation of a translatable molecule in vitro or in vivo.

In some embodiments, a translatable molecule can contain a modified 5' cap.

In further embodiments, a translatable molecule can contain a translation enhancing 5' untranslated region of monomers.

In additional embodiments, a translatable molecule can contain a translation enhancing 3' untranslated region of monomers.

A translatable molecule of this invention can exhibit increased translation efficiency in vivo as compared to a native mRNA that encodes the same translation product. For example, the translation efficiency can be increased by 10%, 20%, 50% or more.

In another aspect, a translatable molecule of this invention can exhibit at least 2-fold, 3-fold, 5-fold, or 10-fold increased translation efficiency in vivo as compared to a native mRNA that encodes the same translation product.

In a further aspect, a translatable molecule of this invention can produce at least 2-fold, 3-fold, 5-fold, or 10-fold increased levels of a polypeptide or protein in vivo as compared to a native mRNA that encodes the same polypeptide or protein.

In certain embodiments, a translatable molecule can provide increased levels of a polypeptide or protein in vivo as compared to a native mRNA that encodes the same polypeptide or protein. For example, the level of a polypeptide or protein can be increased by 10%, or 20%, or 30%, or 40%, or 50%, or more.

Embodiments of this invention further encompass processes for making a translatable molecule for expressing a polypeptide or protein. The processes include transcribing in vitro a polypeptide or protein DNA template in the presence of natural and chemically-modified nucleoside triphosphates to form a product mixture, and purifying the product mixture to isolate the translatable molecule. A translatable molecule may also be made by methods as are known in the art.

In additional embodiments, this invention provides methods for treating a disease or condition in a subject by administering to the subject a composition containing a translatable molecule of the invention.

A translatable molecule of this invention may be used for ameliorating, preventing or treating a disease. In these embodiments, a composition comprising a translatable molecule of this invention can be administered to regulate, modulate, or increase the concentration or effectiveness of the natural enzyme in a subject. In some aspects, the enzyme can be an unmodified, natural enzyme for which the patient has an abnormal quantity.

As used herein, the term "subject" refers to human and non-human animals. The term "subject" is used herein interchangeably with "individual" or "patient." A subject can be a mammal. A subject may be a primate, including non-human primates and humans.

In further aspects, this invention provides processes for production of a translatable polynucleotide molecule. A DNA template molecule can be provided having a non-coding template strand of nucleotides that can be transcribed to provide the product translatable polynucleotide. The DNA may contain an open reading frame in the template strand, which template is an alternative variation from a wild type or native version. The DNA may further include a promoter. The DNA can be transcribed in the presence of nucleoside triphosphates, including optionally a 5' cap, and along with one or more chemically modified nucleoside triphosphates to form a product mixture. The product translatable polynucleotide can be isolated and purified from the product mixture.

In some aspects, this invention provides processes for production of a translatable product RNA molecule. A double stranded DNA molecule can be provided having a non-coding template strand of nucleotides that can be transcribed to provide the product RNA. The double stranded DNA may contain an open reading frame in the template strand, which template is an alternative variation from a wild type or native version. In the template, certain adenosine nucleotides may be replaced by non-adenosine nucleotides, while preserving codon assignment to a target RNA product. The double stranded DNA may further include a double stranded promoter for transcribing the template strand, such as a T7 promoter. The DNA can be transcribed in the presence of nucleoside triphosphates, including optionally a 5' cap, and along with one or more chemically modified nucleoside triphosphates to form a product mixture. The product RNA product can be isolated and purified from the product mixture. The product RNA is a translatable molecule that contains natural and chemically modified nucleotides, and enhanced translational efficiency and resulting activity.

In further aspects, this invention provides processes for production of a translatable RNA molecule. A single stranded DNA molecule can be provided having a non-coding template strand of nucleotides that can be transcribed to provide the product RNA. The DNA may contain an open reading frame in the template strand, which template is an alternative variation from a wild type or native version. In the template, certain adenosine nucleotides may be replaced by non-adenosine nucleotides, while preserving codon assignment to a target RNA product. The DNA may further include a promoter. The DNA can be transcribed in the presence of nucleoside triphosphates, including optionally a 5' cap, and along with one or more chemically modified nucleoside triphosphates to form a product mixture. The product RNA can be isolated and purified from the product mixture.

The properties of the translatable compounds of this invention arise according to their molecular structure, and the structure of the molecule in its entirety, as a whole, can provide significant benefits based on those properties. Embodiments of this invention can provide translatable molecules having one or more properties that advantageously provide enhanced effectiveness in regulating protein expression or concentration, or modulating protein activity. The molecules and compositions of this invention can provide formulations for therapeutic agents for various diseases and conditions, which can provide clinical agents.

This invention provides a range of translatable molecules that are surprisingly translatable to provide active peptide or protein, in vitro and in vivo.

The translatable structures and compositions can have increased translational activity and cytoplasmic half-life. In these embodiments, the translatable structures and compositions can provide increased functional half-life in the cytoplasm of mammalian cells over native mRNA molecules. The inventive translatable molecules can have increased half-life of activity with respect to a corresponding native mRNA.

In additional aspects, this invention provides increased activity for mRNA-based drugs as compared to utilizing native compositions, and can reduce the dose levels required for efficacious therapy.

In further aspects, this invention provides increased activity for translatable or mRNA-based molecules, as compared to utilizing a native mRNA as active agent.

In some aspects, this invention can provide translatable molecules that may reduce the cellular innate immune response, as compared to that induced by a natural nucleic acid, peptide or protein.

In additional embodiments, this invention provides methods for treating a disease or condition in a subject by administering to the subject a composition containing a translatable molecule.

Variation of mRNA Construct Coding Regions

In some aspects, the coding region of an mRNA construct of this invention may contain different codons, or alternative codons, as compared to a native mRNA. The native mRNA may be a human mRNA. An mRNA construct of this invention having such different codons, can encode a protein of interest having the same amino acid sequence as a native protein. The native protein may be a human protein. The native protein may be a human therapeutic protein. In some embodiments, an mRNA construct of this invention may contain different codons such that the expression levels of the protein of interest may be increased, in cells, in tissues, in vivo, or in therapeutic uses, as compared to a native mRNA.

In some embodiments, the coding region of an mRNA construct of this invention, which can be used to express a protein of interest, or a fragment thereof, may contain different codons as compared to a native mRNA which can express the same protein of interest.

Some methods for using different codons or alternative codon are given in Gustafsson et al., *Codon bias and heterologous protein expression,* 2004, Trends Biotechnol 22: 346-53.

For example, a high codon adaptation index (CAI) is described in Villalobos et al., *Gene Designer: a synthetic biology tool for constructing artificial DNA segments,* 2006, BMC Bioinformatics 7:285. For a high CAI a most frequently used synonymous codon may be used for an entire protein coding sequence.

In another example, a Low U method targets only U-containing codons that can be replaced with a synonymous codon with fewer U moieties. If there are a few choices for the replacement, the more frequently used codon will be selected. The remaining codons in the sequence are not changed by the LowU method.

Variant Templates for Translatable Molecules

In some embodiments, a variant DNA template may be utilized to make a translatable molecule capable of encoding a polypeptide or protein. A variant DNA template of this disclosure may exhibit advantages in processes for making a translatable molecule, and the efficiency of the translatable molecule. Variation of the template can be utilized to enhance incorporation of modified nucleotides or monomers in a translatable molecule of this invention. In certain aspects, variation of the template can be utilized to enhance the structural features of the translatable molecule. The enhanced structural features of the translatable molecule can provide unexpectedly advantageous properties, including translation efficiency to provide a polypeptide or protein product.

In some aspects of this invention, variation of the template may include reducing the occurrence or frequency of appearance of certain nucleotides in the template strand. Reducing the occurrence of a certain nucleotide can alter the structures and processes of this disclosure to provide non-native forms, which may achieve surprisingly improved properties of a translatable RNA product encoding a polypeptide or protein.

Aspects of this invention may require a variant DNA template in processes for making a translatable molecule. A DNA molecule can have a non-coding template strand of nucleotides that can be transcribed to provide a target translatable molecule.

A target translatable molecule can be any RNA, whether native or modified, synthetic or derived from a natural source.

In some embodiments, a variant DNA template can be used for which an open reading frame of the template strand is transformed to an alternative form, while preserving codon assignment.

In certain embodiments, a DNA template can be used for which alternative nucleotides are used based on alternative codon use and/or sequence degeneracy.

In additional embodiments, a DNA template may have certain nucleotides replaced with alternative nucleotides, while preserving codon assignment.

Embodiments of this invention advantageously utilize alternative codons in a DNA template of this invention to be used in processes for making a translatable molecule. The variations that can be achieved in a DNA template of this invention can be far greater in scope than for cells and organisms, which may require preferred codons in many processes. In this invention, a wide range of alternative codons and positions can be used in a DNA template for transcribing a translatable molecule.

In further aspects of this invention, variation of the template may include reducing the occurrence or frequency of appearance of certain nucleotides in the template strand. For example, the occurrence of a nucleotide in a template may be reduced to a level below 25% of nucleotides in the template. In further examples, the occurrence of a nucleotide in a template may be reduced to a level below 20% of nucleotides in the template. In some examples, the occurrence of a nucleotide in a template may be reduced to a level below 16% of nucleotides in the template. In certain examples, the occurrence of a nucleotide in a template may be reduced to a level below 12% of nucleotides in the template.

A variant DNA template of this disclosure may exhibit advantages in processes for making a translatable molecule, and the efficiency of the translatable molecule. Variation of the template can be utilized to enhance incorporation of modified nucleotides or monomers in an RNA product of this invention. In certain aspects, variation of the template can be utilized to enhance the structural features of the translatable molecule. The enhanced structural features of the translatable molecule can provide unexpectedly advantageous properties, including translation efficiency to provide a polypeptide or protein product.

In some aspects of this invention, variation of the template may include reducing the occurrence or frequency of appearance of certain nucleotides in the template strand. Reducing the occurrence of a certain nucleotide can alter the structures and processes of this disclosure to provide forms, which achieve surprisingly improved properties of a translatable RNA product.

Aspects of this invention may require a variant DNA template in processes for making a translatable molecule. A DNA molecule can have a non-coding template strand of nucleotides that can be transcribed to provide a target RNA.

A target RNA can be any RNA, whether native or unknown, synthetic or derived from a natural source. A target RNA can include UNA molecules composed of nucleotides and UNA monomers, and optionally chemically modified nucleotides.

In some embodiments, a variant DNA template can be used for which an open reading frame of the template strand is transformed to an alternative form.

In certain embodiments, a DNA template can be used for which alternative nucleotides are used based on codon degeneracy.

In additional embodiments, a DNA template may have adenosine nucleotides replaced with non-adenosine nucleotides, while preserving codon assignment.

Embodiments of this invention advantageously utilize alternative codons in a DNA template of this invention to be used in processes for making a translatable RNA molecule. The variations that can be achieved in a DNA template of this invention can be far greater in scope than for cells and organisms, which may require preferred codons in many processes. In this invention, a wide range of alternative codons and positions can be used in a DNA template for transcribing an RNA molecule.

Inherent codon redundancy allows up to six different codons for a single amino acid. However, synonymous codons may not have equivalent preference in cells and organisms. Further, codon preference can vary among different genes, and may have functional effects. Codon degeneracy is in general poorly understood, with unpredictable effects on nucleic acid structures and processes. It is not generally known how codon alternatives affect ribosomes, protein folding, translation, and degradation of an RNA.

In some embodiments, a variant DNA template can be used for which an open reading frame of the template strand is transformed to an alternative form.

In certain embodiments, a DNA template can be used for which alternative nucleotides are used based on codon degeneracy.

In additional embodiments, a DNA template may have adenosine nucleotides replaced with non-adenosine nucleotides, while preserving codon assignment.

Embodiments of this invention advantageously utilize alternative codons in a DNA template of this invention to be used in processes for making a translatable RNA molecule. The variations that can be achieved in a DNA template of this invention can be far greater in scope than for cells and organisms, which may require preferred codons in many processes. In this invention, a wide range of alternative codons and positions can be used in a DNA template for transcribing an RNA molecule.

In further aspects of this invention, variation of the template may include reducing the occurrence or frequency of appearance of certain nucleotides in the template strand. For example, the occurrence of deoxyadenosine in a template may be reduced to a level below 25% of nucleotides in the template. In further examples, the occurrence of deoxyadenosine in a template may be reduced to a level below 20% of nucleotides in the template. In some examples, the occurrence of deoxyadenosine in a template may be reduced to a level below 16% of nucleotides in the template. In certain examples, the occurrence of deoxyadenosine in a template may be reduced to a level below 12% of nucleotides in the template.

Inherent codon redundancy allows up to six different codons for a single amino acid. However, synonymous codons may not have equivalent preference in cells and organisms. Further, codon preference can vary among different genes, and may have functional effects. Codon degeneracy is in general poorly understood, with unpredictable effects on nucleic acid structures and processes. It is not generally known how codon alternatives affect ribosomes, protein folding, translation, and degradation of an RNA.

In some embodiments, the level of T can be reduced in a non-template strand, i.e. a coding strand, by replacing a triplet codon containing more than one T to another synonymous codon containing less T than the original triplet. For example, valine encoded by GTT can be replaced by GTC, GTA, or GTG. Serine encoded by TCT, TCC, TCA, TCG, AGT can be replaced by AGC. Complementary changes would be made in the template strand.

Various additional or synonymous codon replacements can be made as are known in the art.

Modalities for Peptides and Proteins

An RNA molecule of this invention may be used for ameliorating, preventing or treating a disease through protein or enzyme modulation or replacement. An RNA molecule of this invention can be administered to regulate, modulate, increase, or decrease the concentration or effectiveness of a natural enzyme in a subject.

In some aspects, the protein can be an unmodified, natural enzyme for which the subject has an abnormal quantity.

In further embodiments, an RNA molecule can be delivered to cells or subjects, and translated to supply increased levels of a natural polypeptide or protein.

An RNA molecule of this invention may be used for ameliorating, preventing or treating a disease through modulation or introduction of a polypeptide or protein. In such embodiments, a translatable molecule of this invention can be administered to regulate, modulate, increase, or decrease the concentration or effectiveness of a peptide or protein in a subject, where the peptide or protein is non-natural or mutated, as compared to a native peptide or protein.

A polypeptide or protein delivered by an RNA molecule of this disclosure can be a modified, non-natural, exogenous, or synthetic polypeptide or protein, which has a pharmacological effect in a subject.

In some embodiments, an RNA molecule can be delivered to cells or subjects, and translated to supply a secretion or concentration of a peptide or protein.

An RNA molecule of this invention can be delivered for therapeutic purposes by any means and methods known in the art.

As show herein, base sequences are shown from left to right, 5' to 3', unless stated otherwise.

Diseases

Examples of diseases for enzyme modulation include lysosomal diseases, for example, Gaucher disease, Fabry disease, Mucopolysaccharidoses (MPS) and related diseases including MPS I, MPS II (Hunter syndrome), and MPS VI.

Examples of diseases for enzyme modulation include hematologic diseases, for example, sickle-cell disease, thalassemia, methemoglobinemia, anemia due to deficiency of hemoglobin or $B_{12}$ intrinsic factor, spherocytosis, glucose-6-phosphate dehydrogenase deficiency, and pyruvate kinase deficiency.

Examples of diseases for enzyme modulation include hemophilia, Von Willebrand disease, Protein S deficiency, age-related macular degeneration, trinucleotide repeat disorders, muscular dystrophy, insertion mutation diseases, DNA repair-deficiency disorders, and deletion mutation diseases.

Examples of diseases and/or conditions for which the translatable molecules of this invention can be translatable to provide an active agent include those in Table 2.

TABLE 2

Rare diseases and proteins

| RARE DISEASE | DEFICIENCY (PROTEIN) |
| --- | --- |
| Aminoacylase 1 deficiency | Aminoacylase 1 |
| Apo A-I deficiency | Apo A-I |
| Carbamoyl phosphate synthetase 1 deficiency | Carbamoyl phosphate synthetase 1 |
| Ornithine transcarbamylase deficiency | Ornithine transcarbamylase |
| Plasminogen activator inhibitor type 1 deficiency | Plasminogen activator inhibitor type 1 |
| Flaujeac factor deficiency | Flaujeac factor (High-molecular-weight kininogen) |
| High-molecular-weight kininogen deficiency congenital | High-molecular-weight kininogen (Flaujeac factor) |
| PEPCK 1 deficiency | PEPCK 1 |
| Pyruvate kinase deficiency liver type | Pyruvate kinase liver type |
| Alpha 1-antitrypsin deficiency | Alpha 1-antitrypsin |
| Anti-plasmin deficiency congenital | Anti-plasmin |
| Apolipoprotein C 2I deficiency | Apolipoprotein C 2I |
| Butyrylcholinesterase deficiency | Butyrylcholinesterase |
| Complement component 2 deficiency | Complement component 2 |
| Complement component 8 deficiency type 2 | Complement component 8 type 2 |
| Congenital antithrombin deficiency type 1 | Antithrombin |
| Congenital antithrombin deficiency type 2 | Antithrombin, type 2 |
| Congenital antithrombin deficiency type 3 | Antithrombin, type 3 |

TABLE 2-continued

Rare diseases and proteins

| RARE DISEASE | DEFICIENCY (PROTEIN) |
| --- | --- |
| Cortisone reductase deficiency 1 | Cortisone reductase |
| Factor VII deficiency | Factor VII |
| Factor X deficiency | Factor X |
| Factor XI deficiency | Factor XI |
| Factor XII deficiency | Factor XII |
| Factor XIII deficiency | Factor XIII |
| Fibrinogen deficiency congenital | Fibrinogen |
| Fructose-1 6-bisphosphatase deficiency | Fructose-1 6-bisphosphatase |
| Gamma aminobutyric acid transaminase deficiency | Gamma aminobutyric acid transaminase |
| Gamma-cystathionase deficiency | Gamma-cystathionase |
| Glut2 deficiency | Glut2 |
| GTP cyclohydrolase I deficiency | GTP cyclohydrolase I |
| Isolated growth hormone deficiency type 1B | Isolated growth hormone type 1B |
| Molybdenum cofactor deficiency | Molybdenum cofactor |
| Prekallikrein deficiency congenital | Prekallikrein |
| Proconvertin deficiency congenital | Proconvertin |
| Protein S deficiency | Protein S |
| Pseudocholinesterase deficiency | Pseudocholinesterase |
| Stuart factor deficiency congenital | Stuart factor |
| Tetrahydrobiopterin deficiency | Tetrahydrobiopterin |
| Type 1 plasminogen deficiency | Plasminogen |
| Urocanase deficiency | Urocanase |
| Chondrodysplasia punctata with steroid sulfatase deficiency | Chondrodysplasia punctata with steroid sulfatase/X-linked chondrodysplasia punctata 1 |
| Homocystinuria due to CBS deficiency | CBS |
| Guanidinoacetate methyltransferase deficiency | Guanidinoacetate methyltransferase |
| Pulmonary surfactant protein B deficiency | Pulmonary surfactant protein B |
| Aminoacylase 1 deficiency | Aminoacylase 1 |
| Acid Sphingomyelinase Deficiency | Enzyme found in lysosomes, responsible for conversion of lipid sphingomyelin into lipid ceramide |
| Adenylosuccinate Lyase Deficiency | Neurological disorder, brain dysfunction (encephalopathy) and to delayed development of mental and movement abilities, autistic behaviors and seizures |
| Aggressive Angiomyxoma | Myxoid tumor involving the blood vessels, may be a non-metastasizing benign tumor |
| Albrights Hereditary Osteodystrophy | Inherited in an autosomal dominant pattern, lack of responsiveness to parathyroid hormone, low serum calcium, high serum phosphate |
| Carney Stratakis Syndrome | Very rare syndrome characterized by gastrointestinal stromal tumors and paragangliomas. |
| Carney Triad Syndrome | Characterized by the coexistence of 3 types of neoplasms, mainly in young women, including gastric gastrointestinal stromal tumor, pulmonary chondroma, and extra-adrenal paraganglioma |
| CDKL5 Mutation | Results in severe neurodevelopmental impairment and early onset, difficult to control seizures |
| CLOVES Syndrome | Complex vascular anomalies: Congenital, Lipomatous Overgrowth, Vascular malformations, Epidermal nevi and Scoliosis/Skeletal/Spinal anomalies |
| Cockayne Syndrome | Characterized by short stature and an appearance of premature aging, failure to gain weight, abnormally small head size, and impaired development of the nervous system |
| Congenital Disorder of Glycosylation type 1R | Rare inborn errors of metabolism involving deficient or defective glycosylation |
| Cowden Syndrome | Characterized by multiple noncancerous, tumor-like growths called hamartomas and an increased risk of developing certain cancers |
| DEND Syndrome | Generally severe form of neonatal diabetes mellitus characterized by a triad of developmental delay, epilepsy, and neonatal diabetes |
| Dercum's Disease | Characterized by multiple, and painful lipomas. These lipomas mainly occur on the trunk, the upper arms and upper legs |
| Febrile Infection-Related Epilepsy Syndrome | Explosive-onset, potentially fatal acute epileptic encephalopathy, develops in previously healthy children and adolescents following the onset of a non-specific febrile illness |

TABLE 2-continued

Rare diseases and proteins

| RARE DISEASE | DEFICIENCY (PROTEIN) |
| --- | --- |
| Fibular Aplasia Tibial Campomelia Oligosyndactyly Syndrome | Unknown genetic basis and inheritance with variable expressivity and penetrance |
| Food Protein-Induced Enterocolitis Syndrome | A non-IgE mediated immune reaction in the gastrointestinal system to one or more specific foods, commonly characterized by profuse vomiting and diarrhea |
| Foreign Body Giant Cell Reactive Tissue Disease | Collection of fused macrophages which are generated in response to the presence of a large foreign body; particularly evident with implants that cause the body chronic inflammation and foreign body response |
| Galloway-Mowat | Physical features may include an unusually small head and additional abnormalities of the head and facial area; damage to clusters of capillaries in the kidneys resulting in abnormal kidney function; and, in many cases, protrusion of part of the stomach through an abnormal opening in the diaphragm |
| Gitelman syndrome | Autosomal recessive kidney disorder characterized by hypokalemic metabolic alkalosis with hypocalciuria, and hypomagnesemia. |
| Glycerol Kinase Deficiency | X-linked recessive enzyme defect that is heterozygous in nature, responsible gene in a region containing genes in which deletions can cause DMD and adrenal hypoplasia congenita |
| Glycogen Storage Disease type 9 | Caused by the inability to break down glycogen. The different forms of the condition can affect glycogen breakdown in liver cells, muscle cells or both |
| gm 1 gangliosidosis | Autosomal recessive lysosomal storage disease characterized by accumulation of ganglioside substrates in lysosomes |
| Hereditary spherocytosis | Affects red blood cells, shortage of red blood cells, yellowing of the eyes and skin, and an enlarged spleen |
| Hidradenitis Suppurativa Stage III | Disorder of the terminal follicular epithelium in the apocrine gland-bearing skin, frequently causing keloids, contractures, and immobility. Stage III is defined as multiple lesions, with more extensive sinus tracts and scarring |
| Horizonatal Gaze Palsy with Progressive Scoliosis | Disorder that affects vision and also causes an abnormal curvature of the spine |
| IMAGe syndrome | The combination of intrauterine growth restriction, metaphyseal dysplasia, adrenal hypoplasia congenita, and genital anomalies (only about 20 cases reported in the medical literature) |
| Isodicentric 15 | Chromosome abnormality in which a child is born with extra genetic material from chromosome 15 |
| isolated hemihyperplasia | One side of the body grows more than other, causing asymmetry |
| Juvenile Xanthogranuloma | Usually benign and self-limiting. It occurs most often in the skin of the head, neck, and trunk but can also occur in the arms, legs, feet, and buttocks |
| Kasabach-Merritt Syndrome | A vascular tumor leads to decreased platelet counts and sometimes other bleeding problems |
| Kniest Dysplasia | Disorder of bone growth characterized by short stature (dwarfism) with other skeletal abnormalities and problems with vision and hearing |
| Koolen de-Vries Syndrome | Disorder characterized by developmental delay and mild to moderate intellectual disability. They usually have weak muscle tone in childhood. About half have recurrent seizures |
| Lennox-Gastaut syndrome | Type of epilepsy with multiple different types of seizures, particularly tonic (stiffening) and atonic (drop) seizures. Intellectual development is usually, but not always, impaired |
| Lymphangiomatosis | Congenital and can affect any of the body's systems except the central nervous system (including the brain) |
| Lymphangiomiomytosis | Can occur either sporadically or in association with the tuberous sclerosis complex (TSC) and is often considered a forme fruste of TSC |
| MASA Syndrome | X-linked recessive neurological disorder |
| Mast Cell Activation disorder | Condition with signs and symptoms involving the skin, gastrointestinal, cardiovascular, respiratory, and neurologic systems |
| Mecp2 Duplication Syndrome | Genetic neurodevelopmental disorder characterized by low muscle tone, potentially severe intellectual disability, developmental delays, recurrent respiratory infections, speech abnormalities, seizures, and progressive spasticity |
| Mucha Habermann | Skin disorder |
| Neonatal Hemochromatosis | Severe liver disease of fetal or perinatal onset, associated with deposition of stainable iron in extrahepatic sites, disordered iron handling due to injury to the perinatal liver, as a form of fulminant hepatic failure |
| N-glycanase deficiency | The encoded enzyme may play a role in the proteasome-mediated degradation of misfolded glycoproteins |

TABLE 2-continued

Rare diseases and proteins

| RARE DISEASE | DEFICIENCY (PROTEIN) |
| --- | --- |
| Opsoclonus Myoclonus Syndrome | Neurological disorder of unknown causes which appears to be the result of an autoimmune process involving the nervous system |
| Persistent genital arousal disorder | Results in a spontaneous, persistent, and uncontrollable genital arousal, with or without orgasm or genital engorgement, unrelated to any feelings of sexual desire |
| Pompe Disease | Inherited disorder caused by the buildup of glycogen in the body's cells. The accumulation of glycogen in certain organs and tissues, especially muscles, impairs their ability to function normally |
| Progressive Familial Intrahepatic Cholestasis | Disorder that causes progressive liver disease, which typically leads to liver failure. In people with PFIC, liver cells are less able to secrete a digestive fluid called bile. The buildup of bile in liver cells causes liver disease in affected individuals |
| Pseudohypoparathyroidism type 1a | Characterized by renal resistance to parathyroid hormone, resulting in hypocalcemia, hyperphosphatemia, and elevated PTH; resistance to other hormones including thydroid stimulating hormone, gonadotropins and growth-hormone-releasing hormone |
| PTEN Hamartoma Tumor Syndrome | The gene was identified as a tumor suppressor that is mutated in a large number of cancers at high frequency |
| Schnitzler syndrome | Characterised by chronic hives and periodic fever, bone pain and joint pain (sometimes with joint inflammation), weight loss, malaise, fatigue, swollen lymph glands and enlarged spleen and liver |
| Scleroderma | Chronic hardening and tightening of the skin and connective tissues |
| Semi Lobar Holoprosencephany | Holoprosencephany: birth defect of the brain, which often can also affect facial features, including closely spaced eyes, small head size, and sometimes clefts of the lip and roof of the mouth. Semilobar holoprosencephaly is a subtype of holoprosencephaly characterised by an incomplete forebrain division |
| Sjogren's Syndrome | Immune system disorder characterized by dry eyes and dry mouth |
| Specific Antibody Deficiency Disease | Immune |
| SYNGAP 1 | A ras GTPase-activating protein that is critical for the development of cognition and proper synapse function |
| Trigeminal Trophic Syndrome | This is the wing of tissue at the end of the nose above the nostril. Trigeminal trophic syndrome is due to damage to the trigeminal nerve |
| Undiffentiated Connective Tissue Disease | Systemic autoimmune disease |
| X-linked hypophosphatemia | X-linked dominant form of rickets (or osteomalacia) that differs from most cases of rickets in that ingestion of vitamin D is relatively ineffective. It can cause bone deformity including short stature and genu varum |

Chemically-Modified Nucleotides

Examples of nucleic acid monomers include non-natural, modified, and chemically-modified nucleotides, including any such nucleotides known in the art.

In the examples of modified or chemically-modified nucleotides herein, an alkyl, cycloalkyl, or phenyl substituent may be unsubstituted, or further substituted with one or more alkyl, halo, haloalkyl, amino, or nitro substituents.

As used herein, in the context of polynucleotide sequences, the symbol N can represent any natural nucleotide monomer, or any modified nucleotide monomer.

As used herein, in the context of polynucleotide sequences, the symbol Q represents a non-natural, modified, or chemically-modified nucleotide monomer.

Examples of chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4,N^4$-dimethylcytidine.

Examples of chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine, 5-propynyluridine, 5-bromouridine, 5-fluorouridine, 5-iodouridine; pseudouridine, $N^1$-hydroxypseudouridine, $N^1$-methylpseudouridine, and $N^1$-hydroxymethylpseudouridine.

Examples of chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, $N^1$-phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^1$-alkyl-$N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Examples of pseudouridines include $N^1$-methylpseudouridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Examples of chemically-modified nucleotides include 5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine, pseudouridine, 2'-O-methylpseudouridine, $N^1$-hydroxypseudouridine, $N^1$-methylpseudouridine, 2'-O-methyl-$N^1$-methylpseudouridine, $N^1$-ethylpseudouridine, $N^1$-hydroxymethylpseudouridine, and Arauridine.

Examples of modified or chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, N6-threonylcarbamoyl-adenosine, $N^6$-methyl-$N^6$-threonylcarbamoyl-adenosine, 2-methylthio-$N^6$-threonylcarbamoyl-adenosine, $N^6,N^6$-dimethyladenosine, N6-hydroxynorvalylcarbamoyladenosine, 2-methylthio-$N^6$-hydroxynorvalylcarbamoyl-adenosine, $N^6$-acetyl-adenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6,N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Examples of modified or chemically-modified nucleotides include $N^1$-methylguanosine, $N^2$-methylguanosine, thienoguanosine, 7-deazaguanosine, 8-oxoguanosine, 8-bromoguanosine, $O^6$-methylguanosine, xanthosine, inosine, and $N^1$-methylinosine.

Examples of non-natural, modified, and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, and 3'-inverted thymidine.

Examples of non-natural, modified, and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides.

Examples of non-natural, modified, and chemically-modified nucleotide monomers include 2',4'-Constrained 2'-O-Methoxyethyl (cMOE) and 2'-O-Ethyl (cEt) Modified DNAs.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Examples of nucleotide monomers include pseudouridine (psi-Uridine) and 1-methylpseudouridine.

Some examples of modified nucleotides are given in Saenger, Principles of Nucleic Acid Structure, Springer-Verlag, 1984.

Example of base modifications described above can be combined with additional modifications of nucleoside or nucleotide structure, including sugar modifications and linkage modifications.

Molecular Structures and Sequences

A translatable molecule can be designed to express a target peptide or protein. In some embodiments, the target peptide or protein can be associated with a condition or disease in a subject.

In some aspects, the base sequence of a translatable molecule can include a portion that is identical to at least an effective portion or domain of a base sequence of an mRNA, where an effective portion is sufficient to impart a therapeutic activity to a translation product of the translatable molecule.

In some aspects, this invention provides active translatable molecules having a base sequence identical to at least a fragment of a native nucleic acid molecule of a cell.

In certain embodiments, the base sequence of a translatable molecule can include a portion that is identical to a base sequence of an mRNA, except for one or more base mutations. The number of mutations for the translatable molecule should not exceed an amount that would produce a translation product of the translatable molecule having substantially less activity than the mRNA.

Molecular Cap Structure

A translatable molecule of this invention may have a 5'-end capped with various groups and their analogues as are known in the art. In an exemplary embodiment, the 5' cap may be a m7GpppGm cap. In further embodiments, the 5' cap may be selected from m7GpppA, m7GpppC; unmethylated cap analogs (e.g., GpppG); dimethylated cap analog (e.g., m2,7GpppG), a trimethylated cap analog (e.g., m2,2,7GpppG), dimethylated symmetrical cap analogs (e.g., m7Gpppm7G), or anti reverse cap analogs (e.g., ARCA; m7,2'OmeGpppG, m72'dGpppG, m7,3'OmeGpppG, m7,3'dGpppG and their tetraphosphate derivatives) (see, e.g., Jemielity, J. et al., RNA 9: 1108-1122 (2003). In other embodiments, the 5' cap may be an ARCA cap (3'-OMem7G(5')pppG). The 5' cap may be an mCAP (m7G(5')ppp (5')G, N⁷-Methyl-Guanosine-5'-Triphosphate-5'-Guanosine). The 5' cap may be resistant to hydrolysis.

Some examples of 5' cap structures are given in WO2015/051169A2, WO/2015/061491, and U.S. Pat. Nos. 8,093,367 and 8,304,529.

Tail Region

A translatable polynucleotide may comprise a tail region. In some embodiments, the tail region can be a polyA or polyC tail.

A tail can be added by methods known in the art. For example, poly A polymerase can be used to add a tail to a synthetic or in vitro transcribed RNA. Other methods include the use of a transcription vector to encode poly A tails. Additional methods include using a ligase via splint ligation, wherein polyA may be ligated to the 3' end of a sense RNA.

In some embodiments, a translatable polynucleotide can comprise a 3' polyA tail structure, or a 3' polyC tail structure. In some embodiments, the length of the tail can be at least about 5, 10, 15, 20, 25, 30, 35, 40, 45, 50, 100, 200, or 300 nucleotides.

In further embodiments, a 3' polyA tail or a may contain about 5 to 300 adenosine nucleotides, or about 30 to 250 adenosine nucleotides, or about 60 to 220 adenosine nucleotides, or about 80 to 200 adenosine nucleotides, or about 90 to about 150 adenosine nucleotides, or about 100 to about 120 adenosine nucleotides. In certain embodiments, a 3' polyA tail can be about 100 nucleotides in length, or about 115 nucleotides in length.

In some embodiments, a 3' tail may contain one or more UNA monomers. In some embodiments, a 3' tail may contain 2, 3, 4, 6, 8, 10, 12, 16, 20, or more UNA monomers.

In some embodiments, a 3' polyC tail may contain about 5 to 300 cytosine nucleotides, for example, about 30 to 250 cytosine nucleotides, about 60 to 220 cytosine nucleotides, about 80 to about 200 cytosine nucleotides, about 90 to 150 cytosine nucleotides, or about 100 to about 120 cytosine nucleotides. In certain embodiments, a 3' polyC tail is about 100 nucleotides in length, or about 115 nucleotides in length.

A polyC tail may be added to a polyA tail. A polyC tail may substitute for a polyA tail. A polyC tail may be added to the 5' end of a polyA tail, or to the 3' end of a polyA tail.

In some embodiments, the length of the poly A and/or poly C tail can be adjusted to control the stability and/or transcription of protein of a modified translatable polynucleotide molecule of this invention.

In certain embodiments, the length of the polyA tail can be adjusted to modify the level of resistance of the mRNA to nucleases to control the time course of polynucleotide expression and/or polypeptide production in a target cell.

5' and 3' Untranslated Regions (UTRs)

Embodiments of this invention provide a range of translatable polynucleotide molecules having surprisingly increased stability and/or efficiency of translation, based on the structure of untranslated regions.

A translatable polynucleotide of this invention may comprise one or more 5' untranslated regions, and one or more 3' untranslated regions.

In some embodiments, a translatable polynucleotide may contain a 5' UTR that is at least about 25, 50, 75, 100, 125, 150, 175, 200, 300, 400, or 500 nucleotides in length. A 5' UTR may contain about 50 to 300 nucleotides, or about 75 to 250 nucleotides, or about 100 to 200 nucleotides, or about 120 to 150 nucleotides, or about 135 nucleotides.

In additional aspects, the translatable oligomeric molecule comprises an internal ribosome entry site (IRES). As is understood in the art, an IRES is an RNA element that allows for translation initiation in an end-independent manner. In exemplary embodiments, the IRES is in the 5' UTR. In other embodiments, the IRES may be outside the 5' UTR.

In some embodiments, a translatable polynucleotide may contain a 3' UTR that is at least about 25, 50, 75, 100, 125, 150, 160, 175, 200, 300, 400, or 500 nucleotides in length. In some embodiments, a 3' UTR contains about 50 to 300 nucleotides, or about 75 to 250 nucleotides, or about 100 to 200 nucleotides, or about 140 to 175 nucleotides, or about 160 nucleotides.

In additional embodiments, a 3' UTR may contain one or more UNA monomers. A 3' UTR may contain 1, 2, 3, 4, 5, 6, 10, 12, 16, 20, or more UNA monomers.

A translatable polynucleotide of this invention may comprise one or more 5' untranslated regions of Table 3, derived from *Arabidopsis thaliana*.

As used herein, the term "5' UTR derived from a gene expressed by *Arabidopsis thaliana*" is used to describe 5' UTRs derived from genes in *Arabidopsis thaliana* identified in the art. *Arabidopsis thaliana* genes known in the art can be found in The *Arabidopsis* Information Resource (TAIR). In certain embodiments of the invention, the 5' UTRs derived from genes expressed by *Arabidopsis thaliana* include those appearing in Table 3.

TABLE 3

5' UTRs of *Arabidopsis thaliana*

| SEQ ID NO. | GENE | SEQUENCE | FUNCTION |
|---|---|---|---|
| 1 | AT1G67090 | CACAAAGAGTAAAGAAGAACA | Ribulose bisphosphate carboxylase small chain 1A |
| 2 | AT1G35720 | AACACTAAAAGTAGAAGAAAA | Annexin |
| 3 | AT5G45900 | CTCAGAAAGATAAGATCAGCC | Ubiquitin-like modifier-activating enzyme atg7 |
| 4 | AT5G61250 | AACCAATCGAAAGAAACCAAA | Heparanase-like protein 2 |
| 5 | AT5G46430 | CTCTAATCACCAGGAGTAAAA | 60S ribosomal protein L32-2 |
| 6 | AT5G47110 | GAGAGAGATCTTAACAAAAAA | Chlorophyll A-B binding family protein |

TABLE 3-continued

5' UTRs of *Arabidopsis thaliana*

| SEQ ID NO. | GENE | SEQUENCE | FUNCTION |
|---|---|---|---|
| 7 | AT1G03110 | TGTGTAACAACAACAACAACA | Transducin/WD-40 repeat-containing protein |
| 8 | AT3G12380 | CCGCAGTAGGAAGAGAAAGCC | Actin-related protein 5 |
| 9 | AT5G45910 | AAAAAAAAAAGAAATCATAAA | GDSL esterase/lipase |
| 10 | AT1G58420 | ATTATTACATCAAAACAAAAA | Uncharacterized conserved protein UCP031279 |
| 11 | AT1G07260 | GAGAGAAGAAAGAAGAAGACG | UDP-glycosyltransferase |
| 12 | AT3G55500 | CAATTAAAAATACTTACCAAA | Expansin-A16 |
| 13 | AT3G46230 | GCAAACAGAGTAAGCGAAACG | 17.4 kDa class I heat shock protein |
| 14 | AT2G36170 | GCGAAGAAGACGAACGCAAAG | Ubiquitin-60S ribosomal protein L40-1 |
| 15 | AT1G10660 | TTAGGACTGTATTGACTGGCC | Putative uncharacterized protein |
| 16 | AT4G14340 | ATCATCGGAATTCGGAAAAAG | Casein kinase 1-like protein 11 |
| 17 | AT1G49310 | AAAACAAAAGTTAAAGCAGAC | Putative uncharacterized protein |
| 18 | AT4G14360 | TTTATCTCAAATAAGAAGGCA | Probable methyltransferase PMT3 |
| 19 | AT1G28520 | GGTGGGGAGGTGAGATTTCTT | Transcription factor VOZ1 |
| 20 | AT1G20160 | TGATTAGGAAACTACAAAGCC | Subtilisin-like serine endopeptidase-like protein |
| 21 | AT5G37370 | CATTTTTCAATTTCATAAAAC | Pre-mRNA-splicing factor 38B |
| 22 | AT4G11320 | TTACTTTTAAGCCCAACAAAA | Probable cysteine proteinase |
| 23 | AT5G40850 | GGCGTGTGTGTGTGTTGTTGA | Uroporphyrin III methylase |
| 24 | AT1G06150 | GTGGTGAAGGGGAAGGTTTAG | Transcription factor EMB1444 |
| 25 | AT2G26080 | TTGTTTTTTTTGGTTTGGTT | Glycine dehydrogenase |

Examples of 5' UTR sequences are shown in Table 4. A 5' UTR sequence in Table 4 may include a Kozak sequence.

TABLE 4

5' UTRs

| SEQ ID NO. | SEQUENCE | SOURCE |
|---|---|---|
| 26 | UCAACACAACAUAUACAAAACAAACGAAUCUCAAG CAAUCAAGCAUUCUACUUCUAUUGCAGCAAUUUAA AUCAUUUCUUUUAAAGCAAAAGCAAUUUUCUGAAA AUUUUCACCAUUUACGAACGAUAG | TEV (TOBACCO ETCH VIRUS) |
| 27 | AUUAUUACAUCAAAACAAAAAGCCGCCACC | AT1G58420 |
| 28 | AACUUAAAAAAAAAAAUCAAA aacttaaaaaaaaaatcaaaatggccgccacc | SYNK |
| 29 | UCAAGCUUUUGGACCCUCGUACAGAAGCUAAUACG ACUCACUAUAGGGAAAUAAGAGAGAAAAGAAGAGU AAGAAGAAAUAUAAGAGCCACC | TRUNCATED ROSSI |
| 30 | AAUUAUUGGUUAAAGAAGUAUAUUAGUGCUAAUUU CCCUCCGUUUGUCCUAGCUUUUCUCUUCUGUCAAC CCCACACGCCUUUGGCACA | HUMAN ALBUMIN |

TABLE 4-continued

5' UTRs

| SEQ ID NO. | SEQUENCE | SOURCE |
|---|---|---|
| 31 | CACAUUUGCUUCUGACAUAGUUGUGUUGACUCACAACCCCAGAAACAGACAUC | MOUSE BETA GLOBIN |
| 32 | ACAUUUGCUUCUGACACAACUGUGUUCACUAGCAACCUCAAACAGACACC | HUMAN BETA GLOBIN |
| 33 | UGCACACAGAUCACCUUUCCUAUCAACCCCACUAGCCUCUGGCAAA | MOUSE ALBUMIN |
| 34 | CAUAAACCCUGGCGCGCUCGCGGGCCGGCACUCUUCUGGUCCCACAGACUCAGAGAGAACCCACC | HUMAN ALPHA GLOBIN |
| 35 | AUAAAAAGACCAGCAGAUGCCCCACAGCACUGCUCUUCCAGAGGCAAGACCAACCAAG | HUMAN HAPTOGLOBIN |
| 36 | AGACAAGGUUCAUAUUUGUAUGGGUUACUUAUUCUCUCUUUGUUGACUAAGUCAAUAAUCAGAAUCAGCAGGUUUGCAGUCAGAUUGGCAGGGAUAAGCAGCCUAGCUCAGGAGAAGUGAGUAUAAAAGCCCCAGGCUGGGAGCAGCCAUCACAGAAGUCCACUCAUUCUUGGCAGG | HUMAN TRANSTHYRETIN |
| 37 | UCUGCCCCACCCUGUCCUCUGGAACCUCUGCGAGAUUUAGAGGAAAGAACCAGUUUUCAGGCGGAUUGCCUCAGAUCACACUAUCUCCACUUGCCCAGCCCUGUGGAAGAUUAGCGGCC | HUMAN ANTITHROMBIN |
| 38 | AGAUAAAAAGCCAGCUCCAGCAGGCGCUGCUCACUCCUCCCCAUCCUCUCCCUCUGUCCCUCUGUCCCCUGACCCUGCACUGUCCCAGCACC | HUMAN COMPLEMENT C3 |
| 39 | UAUAUCCGUGGUUUCCUGCUACCUCCAACC | HUMAN COMPLEMENT C5 |
| 40 | GGCACCACCACUGACCUGGGACAGUGAAUCGACA | HUMAN ALPHA-1-ANTITRYPSIN |
| 41 | AUUCAUGAAAAUCCACUACUCCAGACAGACGGCUUUGGAAUCCACCAGCUACAUCCAGCUCCCUGAGGCAGAGUUGAGA | HUMAN ALPHA-1-ANTICHYMOTRYPSIN |
| 42 | AAUAUUAGAGUCUCAACCCCCAAUAAAUAUAGGACUGGAGAUGUCUGAGGCUCAUUCUGCCCUCGAGCCCACCGGGAACGAAAGAGAAGCUCUAUCUCCCCUCCAGGAGCCCAGCU | HUMAN INTERLEUKIN 6 |
| 43 | AGGAUGGGAACUAGGAGUGGCAGCAAUCCUUUCUUUCAGCUGGAGUGCUCCUCAGGAGCCAGCCCCACCCUUAGAAAAG | HUMAN FIBRINOGEN ALPHA CHAIN |
| 44 | AGGGGGAGCCCUAUAAUUGGACAAGUCUGGGAUCCUUGAGUCCUACUCAGCCCCAGCGGAGGUGAAGGACGUCCUUCCCCAGGAGCCGACUGGCCAAUCACAGGCAGGAAG | HUMAN APOLIPOPROTEIN E |
| 45 | AGACGGGUGGGCGGGGCCCAACUGUCCCCAGCUCCUUCAGCCCUUUCUGUCCCCUCCCAGUGAGGCCAGCUGCGGUGAAGAGGGUGCUCUCUUGCCUGGAGUUCCCUCUGCUACGGCUGCCCCCUCCCAGCCCUGGCCCACUAAGCCAGACCCAGCUGUCGCCAUUCCCACUUCUGGUCCUGCCACCUCCUGAGCUGCCUUCCCGCCUGGUCUGGGUAGAGUC | ALANINE AMINOTRANSFERASE 1 |
| 46 | CAGAUCGCCUGGAGACGCCAUCCACGCUGUUUUGACCUCCAUAGAAGACACCGGGACCGAUCCAGCCUCCGCGGCCGGGAACGGUGCAUUGGAACGCGGAUUCCCGUGCCAAGAGUGACUCACCGUCCUUGACACG | HHV |
| 47 | GGGAGAAAGCUUACCAUGGUGCCCCAGGCCCUGCUCUUGGUCCGCUGCUGGUUUCCCCCUCUGCUUCGGCAAGUUCCCCAUCUACACCAUCCCCGACAAGCUGGGGCCGUGGAGCCCCAUCGACAUCCACCACCUGUCCUGCCCCAACAACCUCGUGGUCGAGGACGAGGGCUGCACCAACCUGAGCGGGUUCUCCUAC | ARC5-1 |

TABLE 4-continued

5' UTRs

| SEQ ID NO. | SEQUENCE | SOURCE |
|---|---|---|
| 48 | GGGGCGCUGCCUACGGAGGUGGCAGCCAUCUCCUU CUCGGCAUCAAGCUUACCAUGGUGCCCCAGGCCCU GCUCUUGGUCCCGCUGCUGGUGUUCCCCCUCUGCU UCGGCAAGUUCCCCAUCUACACCAUCCCCGACAAG CUGGGGCCGUGGAGCCCCAUCGACAUCCACCACCU GUCCUGCCCCAACAACCUCGUGGUCGAGGACGAGG GCUGCACCAACCUGAGCGGGUUCUCCUAC | ARC5-2 |
| 49 | GAAUAAAUGUAUAGGGGGAAAGGCAGGAGCCUUGG GGUCGAGGAAAACAGGUAGGGUAUAAAAAGGGCAC GCAAGGGACCAAGUCCAGCAUCCUAGAGUCCAGAU UCCAAACUGCUCAGAGUCCUGUGGACAGAUCACUG CUUGGCA | Mouse GROWTH HORMONE |
| 50 | GACACUUCUGAUUCUGACAGACUCAGGAAGAAACC | MOUSE HEMOGLOBIN ALPHA |
| 51 | UGCAAACACAGAAAUGGAGGAGGAGGGGAAGGAGG AGGAGGAGGAGAAGGAGGAGGAGGUGUGGUGGUG GUGGUGGGAUAAAACCCCUGAGGCAUAAAGGGCUC GGCCGGAGUCAGCACAGCCCAGCCCUUCCAGAGAG AGGCAAGAGAGGUCCACG | MOUSE HAPTOGLOBIN |
| 52 | CUAAUCUCCCUAGGCAAGGUUCAUAUUUGUGUAGG UUACUUAUUCUCCUUUUGUUGACUAAGUCAAUAAU CAGAAUCAGCAGGUUUGGAGUCAGCUUGGCAGGGA UCAGCAGCCUGGGUUGGAAGGAGGGGGUAUAAAAG CCCCUUCACCAGGAGAAGCCGUCACACAGAUCCAC AAGCUCCUGACAGG | MOUSE TRANSTHYRETIN |
| 53 | AUAGGUAAUUUUAGAAAUAGAUCUGAUUUGUAUCU GAGACAUUUUAGUGAAGUGGUGAGAUAUAAGACAU AAUCAGAAGACAUAUCUACCUGAAGACUUUAAGGG GAGAGCUCCCUCCCCCACCUGGCCUCUGGACCUCU CAGAUUUAGGGGAAAGAACCAGUUUUCGGAGUGAU CGUCUCAGUCAGCACCAUCUCUGUAGGAGCAUCGG CC | MOUSE ANTITHROMBIN |
| 54 | AGAGAGGAGAGCCAUAUAAAGAGCCAGCGGCUACA GCCCC AGCUCGCCUCUGCCCACCCCUGCCCCUUACCCCUU CAUUCCUUCCACCUU UUUCCUUCACU | MOUSE COMPLEMENT C3 |
| 55 | UUUAAAAGGAAAGUGGUUACAGGGAGGCCAUGCCC AUGGGUUU | MOUSE COMPLEMENT C5 |
| 56 | AGUCCUUAGACUGCACAGCAGAACAGAAGGCAUG | MOUSE HEPCIDIN |
| 57 | CCCCCAUAUCCCCCUUGGCUCCCAUUGCUUAAAUA CAGACUAGACAGGGCUCUGUCUCCUCAGCCUCGG UCACCACCCAGCUCUGGGACAGCAAGCUGAAA | MOUSE ALPHA-1-ANTITRYPSIN |
| 58 | AGUCAGUCCUCCUUCGCUUCAGCUCCAGUUCUCCU CAUGAGCCAUCCCUAAACGCAGACACC | MOUSE FIBRINOGEN ALPHA CHAIN |
| 59 | UUUCCUCUGCCCUGCUGUGAAGGGGGAGAGAACAA CCCGCCUCUGUGACAGGGGCUGGCACAGCCCGCCC UAGCCCUGAGGAGGGGCGGGACAGGGGGAGUCCU AUAAUUGGACCGGUCUGGGAUCCGAUCCCCUGCUC AGACCCUGGAGGCUAAGGACUUGUUUCGGAAGGAG CUGACUGGCCAAUCACAAUUGCGAAG | APOLIPOPROTEIN E |
| 60 | GGCCGGCCACCGGGUUUGGGAGCAGCCCAGGCUCA CCUUAACCGGAGCGGUGCGGACGGUCCCGCGGCGA CAGGGCUAAUCUCGGCAGGUUCGCG | ALANINE AMINOTRANSFERASE |
| 61 | GUCCUGGACUGACUCCCACAACUCUGCCAGUCUCC AGCCCCUGCCCUUCAGUGGUACAG | CYTOCHROME P450, FAMILY 1 (CYP1A2) |
| 62 | UUUAAGUCAACACCAGGAACUAGGACACAGUUGUC CAGGUGCUGUUGGCCAGUCCCAAC | PLASMINOGEN |

TABLE 4-continued

5' UTRs

| SEQ ID NO. | SEQUENCE | SOURCE |
|---|---|---|
| 63 | AAGGAGCUGGGGAGUGGAGUGUAGGCACUAUAACC UGAAAGACGUGGUCCUGACAGGAGGACAAUUCUAU UCCCUACCAAA | MOUSE MAJOR URINARY PROTEIN 3 (MUP3) |
| 64 | ACCAGCCAGAAGCCACAGUCUCAUC | MOUSE FVII |
| 65 | AAACAGAGCAGGCAGGGGCCCUGAUUCACUGGCCG CUGGGGCCAGGGUUGGGGGCUGGGGGUGCCCACAG AGCUUGACUAGUGGGAUUUGGGGGGGCAGUGGGUG CAGCGAGCCCGGUCCGUUGACUGCCAGCCUGCCGG CAGGUAGACACCGGCCGUGGGUGGGGAGGCGGCU AGCUCAGUGGCCUUGGGCCGCGUGGCCUGGUGGCA GCGGAGCC | HNF-1ALPHA |
| 66 | GGACUUCAGCAGGACUGCUCGAAACAUCCCACUUC CAGCACUGCCUGCGGUGAAGGAACCAGCAGCC | MOUSE ALPHA-FETOPROTEIN |
| 67 | AGGGCCUCGUGGGGGGCGGGAAGGUACUGUCCCAU AUAAGCCUCUGCUCUUGGGGCUCAACCGCUCGCAC CCGCUGCGCUGCACAGGGGGAGAAAAGGAGCCCAG GGUGUGAGCCGGACAACUUCUGGUCCUCUCCUUCC AUCUCCUUACCGGCGUCCCCACCUCAGGACUUUUC CCGCAGGCUGCGAGGGGACCCACAGUUCGUGGCCA CUUGCCUCCUGGGGAGGGCGACUCUCCUCCCAUCC ACUCAAG | MOUSE FIBRONECTIN |
| 68 | GGGGGAAAAAAAAACAGCCAAAAUAUGCCAAAAAG CUUCUCACAACAGCUCCUCAGUAGAAGCAGGGGCC ACUUGGGAAAGCCAGGGCCUGGACGCUAAUGUUCC AGGCUACAUCAUAGGUCCCUUUUCGCUCAGUGAGG CCACCAUCACCACACCAUGGCCACGUAGGCCUCCA GCCAGGGCAACAGGACCUGGAGGCCACCCAAGACU GCAGCUGGCUGCCGCUGGGUCCCCGGGCCAGCUCU UGGCCCCG | MOUSE RETINOL BINDING PROTEIN 4, PLASMA (RBP4) |
| 69 | GAACCGCGGCGAGGAGGGGGGUCGGAGGCCCAGAC UUAUAAAGGCUGCUGGACCCGCGCUACCCGCCAGA CCCCGCCGCCCGGAUCCCCCGCGCUGCCUGUCGCC CCACGUGACCACACUACUAAGCUUGGUCGCC | MOUSE PHOSPHOLIPID TRANSFER PROTEIN (PLTP) |
| 70 | AGGGACUCAUCAACCAGGCCUGGCCUCUGAGUUCA ACGCAGAGCUAGCUGGGAAAUGUUCCGGAUGUUGG CCAAGGCCAGUGUGACGCUGGGCUCCAGAGCGGCA GGUUGGGUCCGGACC | MOUSE ALANINE-GLYOXYLATE AMINOTRANSFERASE (AGXT) |
| 71 | GCUGCCCCUGUGCUGACUGCUGACAGCUGACUGAC GCUCGCAGCUAGCAGGUACUUCUGGGUUGCUAGCC CAGAGCCCUGGGCCGGUGACCCUGUUUUCCCUACU UCCCGUCUUUGACCUUGGGUGCCUUCCAACCUUCU GUUGCC | ALDEHYDE DEHYDROGENASE 1 FAMILY, MEMBER L1 (ALDH1L1) |
| 72 | GGGUGCUAAAAGAAUCACUAGGGUGGGGAGGCGGU CCCAGUGGGGCGGGUAGGGGUGUGUGCCAGGUGGU ACCGGGUAUUGGCUGGAGGAAGGGCAGCCCGGGGU UCGGGGCGGUCCCUGAAUCUAAAGGCCCUCGGCUA GUCUGAUCCUUGCCCUAAGCAUAGUCCCGUUAGCC AACCCCCUACCCGCCGUGGGCUCUGCUGCCCGGUG CUCGUCAGC | FUMARYLACETOACETATE HYDROLASE (FAH) |
| 73 | AGGAGGACCUUGGCCAGCGGGCAGAAUGGCAGUUG GUAGAGGAAGGGAGCAAGGGGGUGUUUCCUGGGAC AGGGGGGCGGAGACCUGGAGACUAUAGGCUCCCCC AGGACUCAAGUUCAUUGAGUUUCUGCAGACACUGA ACGGCUUUCAGUCUUCCCGCUGUGACUAUCACCUG UGGGCUCCACCUGCCUGCACCUUUUAGUCAGCACCU UUAGCCAGCACCUGCGCCAGACCCCAGCA | FRUCTOSE BISPHOSPHATASE 1 (FBP1) |
| 74 | AGGCGCCGGUCAGG | MOUSE GLYCINE N-METHYLTRANSFERASE (GNMT) |

TABLE 4-continued

| 5' UTRs | | |
|---|---|---|
| SEQ ID NO. | SEQUENCE | SOURCE |
| 75 | ACCAUCAACC | MOUSE 4-HYDROXYPHENYLPYRUVIC ACID DIOXYGENASE (HPD) |

Examples of 3' UTR sequences are shown in Table 5.

TABLE 5

| 3' UTRs | | |
|---|---|---|
| SEQ ID NO. | SEQUENCE | SOURCE |
| 76 | ACCCCCUUUCCUGCUCUUGCCUGUGAACAAUGGUU AAUUGUUCCCAAGAGAGCAUCUGUCAGUUGUUGGC AAAAUGAUAAAGACAUUUGAAAAUCUGUCUUCUGA CAAAUAAAAAGCAUUUAUUUCACUGCAAUGAUGUU UU | MOUSE BETA GLOBIN |
| 77 | GCUCGCUUUCUUGCUGUCCAAUUUCUAUUAAAGGU UCCUUUGUUCCCUAAGUCCAACUACUAAACUGGGG GAUAUUAUGAAGGGCCUUGAGCAUCUGGAUUCUGC CUAAUAAAAAACAUUUAUUUUCAUUGCAA | HUMAN BETA GLOBIN |
| 78 | CUAGUGACUGACUAGGAUCUGGUUACCACUAAACC AGCCUCAAGAACACCCGAAUGGAGUCUCUAAGCUA CAUAAUACCAACUUACACUUACAAAAUGUUGUCCC CCAAAAUGUAGCCAUUCGUAUCUGCUCCUAAUAAA AAGAAAGUUUCUUCACAU | XBG (XENOPUS BETA GLOBIN) |
| 79 | UGGCAUCCCUGUGACCCCUCCCCAGUGCCUCUCCU GGCCCUGGAAGUUGCCACUCCAGUGCCCACCAGCC UUGUCCUAAUAAAAUUAAGUUGCAUCAUUUUGUCU G | HUMAN GROWTH FACTOR |
| 80 | ACACAUCACAACCACAACCUUCUCAGGCUACCCUG AGAAAAAAGACAUGAAGACUCAGGACUCAUCUUU UCUGUUGGUGUAAAAUCAACACCCUAAGGAACACA AAUUUCUUUAAACAUUUGACUUCUUGUCUCUGUGC UGCAAUUAAUAAAAAAUGGAAAGAAUCUAC | MOUSE ALBUMIN |
| 81 | GCUGGAGCCUCGGUAGCCGUUCCUCCUGCCCGCUG GGCCUCCCAACGGGCCCUCCUCCCCUCCUUGCACC GGCCCUUCCUGGUCUUUGAAUAAAGUCUGAGUGGG CAGCA | HUMAN ALPHA GLOBIN |
| 82 | UGCAAGGCUGGCCGGAAGCCCUUGCCUGAAAGCAA GAUUUCAGCCUGGAAGAGGGCAAAGUGGACGGGAG UGGACAGGAGUGGAUGCGAUAAGAUGUGGUUUGAA GCUGAUGGGUGCCAGCCCUGCAUUGCUGAGUCAAU CAAUAAAGAGCUUUCUUUUGACCCAU | HUMAN HAPTOGLOBIN |
| 83 | AAUGUUCUUAUUCUUUGCACCUCUUCCUAUUUUUG GUUUGUGAACAGAAGUAAAAAUAAAUACAAACUAC UUCCAUCUCA | HUMAN ANTITHROMBIN |
| 84 | CCACACCCCCAUUCCCCCACUCCAGAUAAAGCUUC AGUUAUAUCUCACGUGUCUGGAGUUCUUUGCCAAG AGGGAGAGGCUGAAAUCCCCAGCCGCCUCACCUGC AGCUCAGCUCCAUCCUACUUGAAACCUCACCUGUU CCCACCGCAUUUUCUCCUGGCGUUCGCCUGCUAGU GUG | HUMAN COMPLEMENT C3 |
| 85 | AACCUACCUGCCCUGCCCCCGUCCCCUCCCUUCCU UAUUUAUUCCUGCUGCCCCAGAACAUAGGUCUUGG AAUAAAAUGGCUGGUUCUUUUGUUUUCCAAA | HUMAN HEPCIDIN |
| 86 | ACUAAGUUAAAUAUUUCUGCACAGUGUUCCCAUGG CCCCUUGCAUUUCCUUCUUAACUCUCUGUUACACG UCAUUGAAACUACACUUUUUUGGUCUGUUUUUGUG | HUMAN FIBRINOGEN ALPHA CHAIN |

TABLE 5-continued

3' UTRs

| SEQ ID NO. | SEQUENCE | SOURCE |
|---|---|---|
|  | CUAGACUGUAAGUUCCUUGGGGGCAGGGCCUUUGU CUGUCUCAUCUCUGUAUUCCCAAAUGCCUAACAGU ACAGAGCCAUGACUCAAUAAAUACAUGUUAAAUGG AUGAAUGAAUUCCUCUGAAACUCU |  |
| 87 | ACGCCGAAGCCUGCAGCCAUGCGACCCCACGCCAC CCCGUGCCUCCUGCCUCCGCGCAGCCUGCAGCGGG AGACCCUGUCCCCGCCCCAGCCGUCCUCCUGGGGU GGACCCUAGUUUAAUAAAGAUUCACCAAGUUUCAC GCA | HUMAN APOLIPOPROTEIN E |
| 88 | GCACCCCAGCUGGGGCCAGGCUGGGUCGCCCUGGA CUGUGUGCUCAGGAGCCCUGGGAGGCUCUGGAGCC CACUGUACUUGCUCUUGAUGCCUGGCGGGGUGGGG UGGGGGGGGUGCUGGGCCCCUGCCUCUCUGCAGGU CCCUAAUAAAGCUGUGUGGCAGUCUGACUCC | ALANINE AMINOTRANSFERASE 1 |
| 89 | GAUUCGUCAGUAGGGUUGUAAAGGUUUUUCUUUUC CUGAGAAAACAACCUUUUGUUUUCUCAGGUUUUGC UUUUUGGCCUUUCCCUAGCUUUAAAAAAAAAAAAG CAAAA | MALAT |
| 90 | GGACUAGUUAUAAGACUGACUAGCCCGAUGGGCCU CCCAACGGGCCCUCCUCCCCUCCUUGCACCGAGAU UAAU | ARC3-1 |
| 91 | GGGUGGCAUCCCUGUGACCCCUCCCCAGUGCCUCU CCUGGCCCUGGAAGUUGCCACUCCAGUGCCCACCA GCCUUGUCCUAAUAAAAUUAAGUUGCAUCA | ARC3-2 |
| 92 | CCACUCACCAGUGUCUCUGCUGCACUCUCCUGUGC CUCCCUGCCCCUGGCAACUGCCACCCCUGCGCUU UGUCCUAAUAAAAUUAAGAUGCAUCAUAUCACCCG | MOUSE GROWTH HORMONE |
| 93 | GCUGCCUUCUGCGGGGCUUGCCUUCUGGCCAUGCC CUUCUUCUCUCCUUGCACCUGUACCUCUUGGUCU UUGAAUAAAGCCUGAGUAGGAAGAAAAAAAAAAA | MOUSE HEMOGLOBIN ALPHA |
| 94 | UUCAGGGCUCACUAGAAGGCUGCACAUGGCAGGGC AGGCUGGGAGCCAUGGAAGAGGGGGAAGUGGAAGG GUUGGGCUAUACUCUGAUGGGUUCUAGCCCUGCAC UGCUCAGUCAACAAUAAAAAAAUGUGCUUUGGACC CAUAAAAAAAAAAAAAAAAAAA | MOUSE HAPTOGLOBIN |
| 95 | GAGACUCAGCCCAGGAGGACCAGGAUCUUGCCAAA GCAGUAGCAUCCCAUUUGUACCAAAACAGUGUUCU UGCUCUAUAAACCGUGUUAGCAGCUCAGGAAGAUG CCGUGAAGCAUUCUUAUUAAACCACCUGCUAUUUC AUUCAAACUGUGUUUCUUUUUUAUUCCUCAUUUU UCUCCCCUGCUCCUAAAAACCCAAAAUCUUCUAAAG AAUUCUAGAAGGUAUGCGAUCAAACUUUUUAAAGA AAGAAAAUACUUUUUGACUCAUGGUUUAAAGGCAU CCUUUCCAUCUUGGGGAGGUCAUGGGUGCUCCUGG CAACUUGCUUGAGGAAGAUAGGUCAGAAAGCAGAG UGGACCAACCGUUCAAUGUUUUACAAGCAAAACAU ACACUAAGCAUGGUCUGUAGCUAUUAAAAGCACAC AAUCUGAAGGGCUGUAGAUGCACAGUAGUGUUUUC CCAGAGCAUGUUCAAAAGCCCUGGGUUCAAUCACA AUACUGAAAAGUAGGCCAAAAAACAUUCUGAAAAU GAAAUAUUUGGGUUUUUUUUUAUAACCUUUAGUGA CUAAAUAAGACAAAUCUAAGAGACUAAAAAAAAA AAAAAAAA | MOUSE TRANSTHYRETIN |
| 96 | AAUAUUCUUAAUCUUUGCACCUUUUCCUACUUUGG UGUUUGUGAAUAGAAGUAAAAAUAAAUACGACUGC CACCUCACGAGAAUGGACUUUUCCACUUGAAGACG AGAGACUGGAGUACAGAUGCUACACCACUUUUGGG CAAGUGAAGGGGAGCAGCCAGCCACGGUGGCACA AACCUAUAUCCUGGUGCUUUUUGAAGGUAGAAGCAG GGCGGUCAGGAGUUAAGGCCAGUUGAGGCUGGGCU GCAGAGUGAAAGACCAUGUCUCAAGAUGGUCUUUC UCCUCCCCAAAGUAGAAAAGAAAACCAUAAAAACA AGAGGUAAAUAUAUUACUAUUUCAUCUUUAGAGGAU AGCAGGCAUCUUGAAAGGGUAGAGGGACCUUAAAU | MOUSE ANTITHROMBIN |

TABLE 5-continued

3' UTRs

| SEQ ID NO. | SEQUENCE | SOURCE |
|---|---|---|
| | UCUCAUUAUUGCCCCCAUACUACAAACUAAAAAAC AAACCCGAAUCAAUCUCCCAUAAAGACAGAGAUUC AAAUAAGAGUAUUAAACGUUUUAUUUCUCAAACCA CUCACAUGCAUAAUGUUCUUAUACACAGUGUCAAA AUAAAGAGAAAUGCAUUUUUAUACAAAAAAAAAA A | |
| 97 | CUACAGCCCAGCCCUCUAAUAAAGCUUCAGUUGUA UUUCACCCAUC | MOUSE COMPLEMENT C3 |
| 98 | AAAGUUCUGCUGCACGAAGAUUCCUCCUGCGGCGG GGGGAUUGCUCCUCCUCUGGCUUGGAAACCUAGCC UAGAAUCAGAUACACUUUCUUUAGAGUAAAGCACA AGCUGAUGAGUUACGACUUUGUGAAAUGGAUAGCC UUGAGGGGAGGCGAAAACAGGUCCCCCAAGGCUAU CAGAUGUCAGUGCCAAUAGACUGAAACAAGUCUGU AAAGUUAGCAGUCAGGGGUGUUGGUUGGGCCGGA AGAAGAGACCCACUGAAACUGUAGCCCCUUAUCAA AACAUAUCCUUGCUUGAAAGAAAAAUACCAAGGAC AGAAAAUGCCAUAAAAUCUUGACUUUGCACUC | MOUSE COMPLEMENT C5 |
| 99 | CCUAGAGCCACAUCCUGACCUCUCUACACCCCUGC AGCCCCUCAACCCCAUUAUUUAUUCCUGCCCUCCC CACCAAUGACCUUGAAAUAAAGACGAUUUUAUUUU CAAAAAAAAAAAAAAAA | MOUSE HEPCIDIN |
| 100 | CCACCCUAAAAUGUCAUCCUUCCUUCUGAAUUGGG UUCCUUCCAUUAAACACAGGCUGGCCUGGCUCGUG CCUGAUGCUACAGCAAGUCCUUGACUCUGUGGGUU GUGUGUGUGUGUGUGUGUGUGUGUGUGUGUGUGUG UGUGUGUGUGUGUGUGUGUGUGUGUGUGUCUGUGU GUGUGUGUCUUUAUGCCCUGAGUUUGUUGUGGA CUUGAGAUCAUAGUAUGUCUUGAUAUCUCCUCCAG CCAUGCAAAUAGGUUGUGGGUAGAGGACUGUGGCU GAGACCACAGACUCUGGUCCAAGAACCAUCUGCUC UAAAAAAAAUAAAUCUGUCAUCUCUGGAAAAUAAA GAGGACAUGCUCAAUGACUCAGGGUCCAGC | MOUSE ALPHA-1- ANTITRYPSIN |
| 101 | CUGAAGGGUUAGAAAGUGGGGGCUCUGUUUUCUUU GCUCGGUUAUCCGAGAAGAAAGACAAAACGGAAGA UGAAGGUGUCACGGAUCUUGUGAACUUUUUAAAAC UUUCAAGGUGCUAUUCCAUUGUUCUUUGUACUGUA GCUAAAUGUAACUGAGAUGAGUUACUGCUUUGAAA AAAUAAAGUUUUACAUUUUUUCCACCCUUUAAAAA AAAAAA | MOUSE FIBRINOGEN ALPHA CHAIN |
| 102 | GUAUCCUUCUCCUGUCCUGCAACAACAUCCAUAUC CAGCCAGGUGGCCCUGUCUCAAGCACCUCUCUGGC CCUCUGGUGGCCCUUGCUUAAUAAAGAUUCUCCGA GCACAUUCUGAGUCUCUGUGAGUGAUUC AAAAAAAA | APOLIPOPROTEIN E |
| 103 | GGACGC CUCAGGCACC GGAGCCAGAC CCUCCCAAGA CCACCCAGGC CUUCCUCAAG GACUCUGCCU CAGACCUCAG ACAGGCCACC AACGCUGUUC AUCUUCAUUU CCCCAAGGAG ACUUCUUUCU UUGUGCCUUG AUGUUUGAGA GUUCUUCGAG CAAACAGUGG UUUUGCAAUG UCUCACAGGC CCUGUUUUUG UUUUUGUUUU UGUUUUGUUU UGUUUUGUUC UUUUUUUAAA UGCAACCAAA GUAGAGUCAA CCUGCUCGGC AGAUGUACUU GGAUUCUCUG AAUCGCUAUU CUGUUUGGAG AGUUCCUUUG GGUCUUAAGC AGCCAGAGUA CAUGGAAAUG AGAUUAUGUC AGAUCUGGAG AAACAAGCAG GUGUUUGGAA AUAUGUGACU UGACAUGAUA AGGGCUGGGA AUCCAGAAAU CAAUAGUGAG AUCCAUGAAA UCAAACCCUG ACCAGUGUGA AAAUGUAGCC UUUUGGACAG UAAGCCUGCA AGUCUAGUGA GAACUCAGAG AAAGCUGACC AUUCUGGUCU GAAGAUAGGC AGCGCAUCAC AGGCAAGAAU AUCGAAGUCA GUAGUAGGAC AGGGGUCACA UCAGAUACCA GCUCAAAUUG CACUAGCUAU CUAGAACAGU UUUCUCCAGG UUUGCUGAG CCUUGAUGCA UACCAUCGCC CUCUGCUGGU CGCAGCAGAG AUAAGCAAGG GCUGAAAAUG GAGGCAAUCC UUUCCCAAGG CCCUGAAAGU UGUUUUUCAU GGUUUCAAAC UGAAUUUGGC UCAUUUGUAA CUAACUGAUC ACGGUGCCUG GUUACACUGG CUGCCAAGAA GGAGCGCAUG CAAUCUGAUU | ALANINE AMINOTRANSFERASE |

TABLE 5-continued

3' UTRs

| SEQ ID NO. | SEQUENCE | SOURCE |
|---|---|---|
| | CAGUGCUCUC UUCACAUCAG UUUCCUGCCU CCCUCCCUCA UCUGCGGACA GCAUCCUAUC UCAUCAGGCU UCCCUGUGUG UCACAAAGUA GCAGCCACCA AGCAAAUAUA UUCCUUGAAU UAGCACACCU GGGUGGGCCA UGUGCGCACC AAGGAAACAG GUGCUAUAGG GAGCGCCAGG CCAGGCUUGU CUCUUAACUG UCUCGUUCUU CAGUGAGAGU GGGAAAGCUG UCCGGAGCUC CCGCGCAGGA GCCUGGGUAC CCACGCAGCG AGUCAAGGGA GUUUUCGGAG CCAGAGAGAG AAAGAUGUGA AGGCUGUGGA GUAAGGCUGA AACCAGCCUC CUGCCCUAUA GUCCCACACU GCAGGGGUG CGACUUUAAA ACAGAACUUC AAGUUGUUAA CACUCACAAG CAUUGCAUUA CUGUGAAGGA AGUAGCCGCA UCCAUAACAG GAUGUGAUGG UCUACAGCUU UUCCUUUAAA AGCUGAAAAG GUACCAUGUG UGCUCGCUAG GCAUAUAAUC CAGAUAUGCU CCAGAGUUCU GAGAUUCUUC CAUGAAAGGU UAACUAGAAG CUAGAAUAUU UUUUUAUAUU UUUGUAACAA UUGGCUUUUU UCAUGGGGGG AGGGGAGUAG AGGGUUAGUA UUUUAUAGUCC UAACAAGUCC AAAAAUUUUU AUAAGUGUCU UCAGAUUAUA AAUAACCCUC CAAAUUUUGC AAUGUUUACA UGUUUUUUUU UUAAGAUGAC AAAUAUGCUU GAUUUGCUUU UUAAAUAAAA GUUUAGCUGU UCUAAGAGAU UAACUUCAAG UAGGAUGGCU GGUUAUGAUA GUUUGGAUUU UCUACAGGUU CUGUUGCCAU GCCUUUUGGG UUUCAGCAUC ACUCGAGUCG CAGCAUGUGG GUGGGGCUGU GGAAACCUGG CCAGGCUGGA CCUGGUCAGC CACACCUCAG AGACAUUGUU UCCAUUUGGA UGUGAGCAGG CGCAGGCCUG CAUGCUCUUU CCUACUUAGC AUCAUCAGUU CUUCCGCCUC CUUAGCAUGG UUCUUUGUAA CAGCCAUGCU GGGAAGCUCU GAACAAUAAA AUACUUCCAG AGUGGU | |
| 104 | AGAUUGUCGAGGCAUCGGUGGGGCCGUCACCCUUG UUUCUUUCCUUUUUUAAAAAAAAAAAAAAACAG CUUUUUUUUUUUUGAGAGAAUACAAUUCUUUCCCCA UUUAAUUCAUCUCCAAGCAAUUUUACAAUAGUGUC UAUCAUGUUCACCCCAUAACCCAUACUCAUUAGGA CUUAUGAUUUAAGAUUCCUCCUACCCUGUCUUGCU UGCCGCACCUCAUGCUAAUCUAGUUUUUGACUCAA UAGAUUUGCCUACUCUGGCUGUCUCAUAUAAAUCG AAUGAAUUAUG | CYTOCHROME P450, FAMILY 1 (CYP1A2) |
| 105 | CUAGGUGGAAGGCCGAGCAAAACCUCUGCUUACUA AAGCUUACUGAAUAUGGGGAGAGGGCUUAGGGUGU UUGGAAAAACUGACAGUAAUCAAACUGGGACACUA CACUGAACCACAGCUUCCUGUCGCCCCUCAGCCCC UCCCCUUUUUUGUAUUAUUGUGGGUAAAAUUUUC CUGUCUGUGGACUUCUGGAUUUUGUGACAAUAGAC CAUCACUGCUGUGACCUUUGUUGAAAAUAAACUCG AUACUUACUUUG | PLASMINOGEN |
| 106 | AGAA UGGCCUGAGC CUCCAGUGUU GAGUGGAGAC UUUUCACCAG GACUCCAGCA UCAUCCCUUC CUAUCCAUAC AGACUCCCAU GCCAAGGUCU GUGAUCUGCU CUCCACCGUU CUCACAGAGA AGUGCAAUCC CGUUCUCUCC AGCAUGUUAC CUAGGAUAAC UCAUCAAGAA UCAAAGACUU UCUUUAAAUU UCUCUUUGCC AACACAUGGA AAUUCUCCAU UGAUUUCUUU CCUGUCCUGU UCAAUAAAUG AUUACACUUG CACUUAAAAA AAAAAAAA | MOUSE MAJOR URINARY PROTEIN 3 (MUP3) |
| 107 | CUCC UUGGAUAGCC CAACCCGUCC CAAGAAGGAA GCUACGGCCU GUGAAGCUGU UCUAUGGACU UUCCUGCUAU UCUUGUGUAA GGGAAGAGAA UGAGAUAAAG AGAGAGUGAA GAAAGCAGAG GGGGAGGUAA AUGAGAGAGG CUGGGAAAGG GGAAACAGAA AGCAGGGCCG GGGGAAGAGU CUAAGUUAGA GACUCACAAA GAAACUCAAG AGGGGCUGGG CAGUGCAGUC ACAGUCAGGC AGCUGAGGGG CAGGGUGUCC CUGAGGGAGG CGAGGCUCAG GCCUUGCUCC CGUCUCCCCG UAGCUGCCUC CUGUCUGCAU GCAUUCGGUC UGCAGUACUA CACAGUAGGU AUGCACAUGA GCACGUAGGA CACGUGAAUG UGCCGCAUGC | MOUSE FVII |

TABLE 5-continued

3' UTRs

| SEQ ID NO. | SEQUENCE | SOURCE |
|---|---|---|
| | AUGUGCGUGC CUGUGUGUCC AUCAUUGGCA CUGUUGCUCA CUUGUGCUUC CUGUGAGCAC CCUGUCUUGG UUUCAAUUAA AUGAGAAACA UGGUCAAAAA AAAAAAAAA AAAAA | |
| 108 | CCGUG GUGACUGCCU CCCAGGAGCU GGGUCCCCAG GGCCUGCACU GCCUGCAUAG GGGGUGAGGA GGGCCGCAGC CACACUGCCU GGAGGAUAUC UGAGCCUGCC AUGCCACCUG ACACAGGCUG CUGGCCUUCC CAGAAGUCUA CGCAUUCAUU GACACUGCUG CUCCUCCAUC AUCAGGAAGG GAUGGCUCUG AGGUGUCUCA GCCUGACAAG CGAGCCUCGA GGAGCUGGAG GACGGCCCAA UCUGGGCAGU AUUGUGGACC ACCAUCCCUG CUGUUUAGAA UAGGAAAUUU AAUGCUUGGG ACAGGAGUGG GGAAGCUCGU GGUGCCCGCA CCCCCCCAGU CAGAGCCUGC AGGCCUUCAA GGAUCUGUGC UGAGCUCUGA GGCCCUAGAU CAACACAGCU GCCUGCUGCC UCCUGCACCU CCCCAGGCCA UUCCACCCUG CACCAGAGAC CCACGUGCCU GUUUGAGGAU UACCCUCCCC ACCACGGGGA UUUCCUACCC AGCUGUUCUG CUAGGCUCGG GAGCUGAGGG GAAGCCACUC GGGGCUCUCC UAGGCUUUCC CCUACCAAGC CAUCCCUUCU CCCAGCCCCA GGACUGCACU UGCAGGCCAU CUGUUCCCUU GGAUGUGUCU UCUGAUGCCA GCCUGGCAAC UUGCAUCCAC UAGAAAGGCC AUUUCAGGGC UCGGGUUGUC AUCCCUGUUC CUUAGGACCU GCAACUCAUG CCAAGACCAC ACCAUGGACA AUCCACUCCU CUGCCUGUAG GCCCCUGACA ACUUCCUUCC UGCUAUGAGG GAGACCUGCA GAACUCAGAA GUCAAGGCCU GGGCAGUGUC UAGUGGAGAG GGUACCAAGA CCAGCAGAGA GAAGCCACCU AAGUGGCCUG GGGGCUAGCA GCCAUUCUGA GAAAUCCUGG GUCCCGAGCA GCCCAGGGAA ACACAGCACA CAUGACUGUC UCCUCGGGCC UACUGCAGGG AACCUGGCCU UCAGCCAGCU CCUUUGUCAU CCUGGACUGU AGCCUACGGC CAACCAUAAG UGAGCCUGUA UGUUUAUUUA ACUUUUAGUA AAGUCAGUAA AAAGCAAAAA AAAAAAAAA AAA | HNF-1ALPHA |
| 109 | ACAUC UCCAGAAGGA AGAGUGGACA AAAAAAUGUG UUGACUCUUU GGUGUGAGCC UUUUGGCUUA ACUGUAACUG CUAGUACUUU AACCACAUGG UGAAGAUGUC CAUGUGAGAU UUCUAUACCU UAGGAAUAAA ACUUUUCAA CUAUUUCUCU UCUCCUAGUC UGCUUUUUUU UUAUUAAAAA AUACUUUUUU CCAUUU | MOUSE ALPHA-FETOPROTEIN |
| 110 | UCUU UCCAGCCCCA CCCUACAAGU GUCUCUCUAC CAAGGUCAAU CCACACCCCA GUGAUGUUAG CAGACCCUCC AUCUUUGAGU GGUCCUUUCA CCCUUAAGCC UUUUGCUCUG GAGCCAUGUU CUCAGCUUCA GCACAAUUUA CAGCUUCUCC AAGCAUCGCC CCGUGGGAUG UUUUGAGACU UCUCUCCUCA AUGGUGACAG UUGGUCACCC UGUUCUGCUU CAGGGUUUCA GUACUGCUCA GUGUUGUUUA AGAGAAUCAA AAGUUCUUAU GGUUUGGUCU GGGAUCAAUA GGGAAACACA GGUAGCCAAC UAGGAGGAAA UGUACUGAAU GCUAGUACCC AAGACCUUGA GCAGGAAAGU CACCCAGACA CCUCUGCUUU CUUUUGCCAU CUGACCUGCA GCACUGUCAG GACAUGGCCU GUGGCUGUGU GUUCAAACAC CCCUCCCACA GGACUCACUU UGUCCCAACA AUUCAGAUUG CCUAGAAAUA CCUUUCUCUU ACCUGUUUGU UAUUUAUCAA UUUUUCCCAG UAUUUUUAUA CGGAAAAAAU UGUAUUGAAG ACACUUUGUA UGCAGUUGAU AAGAGGAAUU CAGUAUAAUU | MOUSE FIBRONECTIN |

TABLE 5-continued

3' UTRs

| SEQ ID NO. | SEQUENCE | SOURCE |
|---|---|---|
| | AUGGUUGGUG AUUAUUUUUA UAAGCACAUG CCAACGCUUU ACUACUGUGG AAAGACAAGU GUUUUAAUAA AAAGAUUUAC AUUCCAUGAU GUGGACGUCA UUUCUUUUUU UUUUUAACAU CAUGUGUUUG GAGAG | |
| 111 | CAACGUCUA GGAUGUGAAG UUUGAAGAUU UCUGAUUAGC UUUCAUCCGG UCUUCAUCUC UAUUUAUCUU AGAAGUUUAG UUUCCCCCAC CUCCCCUACC UUCUCUAGGU GGACAUUAAA CCAUCGUCCA AAGUACAUGA GAGUCACUGA CUCUGUUCAC ACAACUGUAU GUCUUACUGA AGGUCCCUGA AAGAUGUUUG AGGCUUGGGA UUCCAAACUU GGUUUAUUAA ACAUAUAGUC ACCAUCUUCC UAU | MOUSE RETINOL BINDING PROTEIN 4, PLASMA (RBP4) |
| 112 | GC CCAUCACCCC ACCUGGGUGG CUGGCAUUCA GGAACCUAAC UGAAGUCUUC UCUGCACCCC CUGCCAACCC CUUCCCAUCU ACAGUGUUAG UGGUCCCGGU GCCACAGAGA AGAGCCCAGU UGGAAGCUAU ACCCGAUUUA AUUCCAGAAU UAGUCAACCA UCAAUUAGAA UCCAUCCACC CCCCUC | MOUSE PHOSPHOLIPID TRANSFER PROTEIN (PLTP) |
| 113 | G CAUCCUCUCA CCAGACUAUG CCCUCCUGGA GGGGCUGGGA AUAUAGCAAG AACGAAAAGA CUGUGCAAGG CCUAGAGCCA GCAAAGAUGC UGAUGUAGCC AGGCCAUGCC GGAAGGAGCA GGGUGAAGCU UCCCCUCUCC CUACAAAUGG AACCUUGUGG AAACAGGAUG CUAAACACCU UCUGAUGGAG CUGUUGCCUG CAGGCCACUG GUCUUUGGGA AUUUUCAAUA AAGUGCUUGC GAGGAAUCUC CUA | MOUSE ALANINE-GLYOXYLATE AMINOTRANSFERASE (AGXT) |
| 114 | AGCCA AGACUGUGAU ACUUCUCCUG UACCCUGUUG ACCUCAGGGA GUGCUGACCC UGUCUGGUGA CUUAGCACCC UCCUGUCCCC AGCACUGCUC CUUUCAGCUG CUGGAGCUCU UGGCCUGGAC CCCUGCUGGU GACAGGACAC CCUCUGAACA AUCAGAAGUG GCUCCAAGUG GAGUGAGCAG UCAUGUCCCC CAUGAAUAAA AAUUGUGAGC AGAGGUCGCC UACAAAAAAA AAAAAAA | ALDEHYDE DEHYDROGENASE 1 FAMILY, MEMBER L1 (ALDH1L1) |
| 115 | A GCUCCGGAAG UCACAAGACA CACCCUUGCC UUAUGAGGAU CAUGCUACCA CUGCAUCAGU CAGGAAUGAA UAAAGCUACU UUGAUUGUGG GAAAUGCCAC AGAAAAAAAA AAAAAAA | FUMARYLACETOACETATE HYDROLASE (FAH) |
| 116 | AGGC CAGCCUUGCC CCUGCCCCAG AGCAGAGCUC AAGUGACGCU ACUCCAUUCU GCAUGUUGUA CAUUCCUAGA AACAAACCUA ACAGCGUGGA UAGUUUCACA GCUUAAUGCU UUGCAAUGCC CAAGGUCACU UCAUCCUCAU GCUAUAAUGC CACUGUAUCA GGUAAUAUAU AUUUUGAGUA GGUGAAGGAG AAAUAAACAC AUCUUUCCUU UAUAAAUUA | FRUCTOSE BISPHOSPHATASE 1 (FBP1) |
| 117 | GUUU CUCCGGCUCC CAGAAGCCCA UGCUCAGGCA AUGGCCCCUA CCCUAAGACC AUCCCCUAAU GCAGAUAUUG CAUUUGGGUG CAGAUGUGGG GGUCGGGCAA ACGGAGUAAA CAAUACAGUC UGCAUUCUCC AAAAAAAAAA AA | MOUSE GLYCINE N-METHYLTRANSFERASE (GNMT) |
| 118 | GCCCCCAU CCACACAUGG ACCACGCAAA GUGCUGGACA CAUCAGUCAU CUCCAACUGG CUGAAAGGCU GAACCUCAGG GCUCCACCCA CGUCAUGGCC | MOUSE 4-HYDROXYPHENYLPYRUVIC ACID DIOXYGENASE (HPD) |

TABLE 5-continued

3' UTRs

| SEQ ID NO. | SEQUENCE | SOURCE |
|---|---|---|
| | ACGCCCCUC UAUUACAAGA GUCCGCCUUG CCUGAGUCCU CCCUGCUGAG UAAAGCUACC CUCCCAGGUC CAAAAAAAAA AAAAAAAAA AAAAAAAAA AAAAAAAAA AAAAAAA | |

The *Xenopus* beta-globin gene sequence is shown in accession no. NM_001096347.1.

Some examples of UTR sequences are found in U.S. Pat. No. 9,149,506.

In some embodiments, a 5' UTR can be derived from a histone, tubulin, globin, GAPDH, actin, or a citric acid cycle enzyme mRNA molecule.

In further embodiments, a 5' UTR may be derived from human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK, AT1G58420, mouse beta globin, mouse albumin, a tobacco etch virus, or fragments of any of the foregoing.

In other embodiments, a 5' UTR sequence may include a partial sequence of a CMV immediate-early 1 (IE1) gene.

In certain embodiments, a 3' UTR may be derived from alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and *xenopus* beta globin, or fragments of any of the foregoing.

Triple Stop Codon

In some embodiments, a translatable oligomer may comprise a sequence immediately downstream of the CDS that creates a triple stop codon. The triple stop codon may be incorporated to enhance the efficiency of translation. In some embodiments, the transatable oligomer may comprise the sequence AUAAGUGAA (SEQ ID NO:119) immediately downstream of a CDS described herein.

Translation Initiation Sites

In some embodiments, a translatable oligomer may comprise a translation initiation site, for example, a Kozak sequence. See, for example, Kozak, Marilyn (1988) Mol. and Cell Biol., 8:2737-2744; Kozak, Marilyn (1991) J. Biol. Chem., 266:19867-19870; Kozak, Marilyn (1990) Proc Natl. Acad. Sci. USA, 87:8301-8305; and Kozak, Marilyn (1989) J. Cell Biol., 108:229-241; and the references cited therein.

In some embodiments, the translation initiation site, e.g., a Kozak sequence, is inserted upstream of a coding sequence. In some embodiments, the translation initiation site is inserted downstream of a 5' UTR. In certain exemplary embodiments, the translation initiation site is inserted upstream of the coding sequence and downstream of a 5' UTR.

In some embodiments, a Kozak Sequence is GCCACC (SEQ ID NO:120).

In further embodiments, a Kozak Sequence is GCCGCCACC (SEQ ID NO:121).

Synthesis Methods

In various aspects, this invention provides methods for synthesis of translatable messenger molecules.

Translatable molecules of this invention can be synthesized and isolated using methods disclosed herein, as well as any pertinent techniques known in the art.

Some methods for preparing nucleic acids are given in, for example, Merino, Chemical Synthesis of Nucleoside Analogues, (2013); Gait, Oligonucleotide synthesis: a practical approach (1984); Herdewijn, Oligonucleotide Synthesis, Methods in Molecular Biology, Vol. 288 (2005).

In some embodiments, a translatable molecule can be made by in vitro transcription (IVT) reaction. A mix of nucleoside triphosphates (NTP) can be polymerized using T7 reagents, for example, to yield RNA from a DNA template. The DNA template can be degraded with RNase-free DNase, and the RNA column-separated.

In some embodiments, a ligase can be used to link a synthetic oligomer to the 3' end of an RNA molecule or an RNA transcript to form a translatable molecule. The synthetic oligomer that is ligated to the 3' end can provide the functionality of a polyA tail, and advantageously provide resistance to its removal by 3'-exoribonucleases. The ligated product translatable molecule can have increased specific activity and provide increased levels of ectopic protein expression.

In certain embodiments, the ligated product of the translatable molecules of this invention can be made with an RNA transcript that has native specificity. The ligated product can be a synthetic molecule that retains the structure of the RNA transcript at the 5' end to ensure compatibility with the native specificity.

In further embodiments, the ligated product of the translatable molecules of this invention can be made with an exogenous RNA transcript or non-natural RNA. The ligated product can be a synthetic molecule that retains the structure of the RNA.

Without wishing to be bound by theory, the canonical mRNA degradation pathway in cells includes the steps: (i) the polyA tail is gradually cut back to a stub by 3' exonucleases, shutting down the looping interaction required for efficient translation and leaving the cap open to attack; (ii) decapping complexes remove the 5' cap; (iii) the unprotected and translationally incompetent residuum of the transcript is degraded by 5' and 3' exonuclease activity.

Embodiments of this invention involve new translatable structures which can have increased translational activity over a native transcript. Among other things, translatable molecules herein may prevent exonucleases from trimming back the polyA tail in the process of de-adenylation.

Embodiments of this invention provide structures, compositions and methods for translatable molecules. Embodiments of this invention can provide translatable molecules containing one or more UNA monomers and having increased functional half-life.

It has been found that ligation of a synthetic oligomer to the 3' end of an mRNA transcript can surprisingly be accomplished with high conversion of the mRNA transcript to the ligation product.

As used herein, the terms polyA tail and polyA oligomer refer to an oligomer of monomers, wherein the monomers can include nucleotides based on adenine, UNA monomers, naturally-occurring nucleotides, modified nucleotides, or nucleotide analogues.

Oligomers for ligation to the 3' end of an RNA may be from 2 to 120 monomers in length, or from 3 to 120 monomers in length, or from 4 to 120 monomers in length, or from 5 to 120 monomers in length, or longer. In an exemplary embodiment, the oligomer for ligation is about 30 monomers in length.

Genetic Basis for Translatable Molecules

In some embodiments, the translatable molecules of this invention can be structured to provide peptides or proteins that are nominally expressed by any portion of a genome. Examples of genes for which a translatable molecule can be used to express the corresponding peptide or protein are set forth below.

Examples of genes for which a translatable molecule can be used to express the corresponding peptide or protein include: Neoplasia, PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc.

Examples of genes for which a translatable molecule can be used to express the corresponding peptide or protein include: Age-related Macular Degeneration, Schizophrenia, Aber; Ccl2; Cc2; cp (ceruloplasmin); Timp3; cathepsinD; Vldlr; Ccr2 Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b.

Examples of genes for which a translatable molecule can be used to express the corresponding peptide or protein include: 5-HTT (Slc6a4); COMT; DRD (Drd1a); SLC6A3; DAOA; DTNBP1; Dao (Dao1).

Examples of genes for which a translatable molecule can be used to express the corresponding peptide or protein include: Trinucleotide Repeat Disorders, HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn 1 (DRPLA Dx); CBP (Creb-BP-global instability); VLDLR (Alzheimer's); Atxn7; Atxn10.

Examples of genes for which a translatable molecule can be used to express the corresponding peptide or protein include: Fragile X Syndrome, FMR2; FXR1; FXR2; mGLUR5.

Examples of genes for which a translatable molecule can be used to express the corresponding peptide or protein include: Secretase Related Disorders, APH-1 (alpha and beta); Presenilin (Psen1); nicastrin (Ncstn); PEN-2.

Examples of genes for which a translatable molecule can be used to express the corresponding peptide or protein include: Nos1.

Examples of genes for which a translatable molecule can be used to express the corresponding peptide or protein include: Parp1.

Examples of genes for which a translatable molecule can be used to express the corresponding peptide or protein include: Nat1; Nat2.

Examples of genes for which a translatable molecule can be used to express the corresponding peptide or protein include: Prion-related disorders, Prp.

Examples of genes for which a translatable molecule can be used to express the corresponding peptide or protein include: ALS disease, SOD1; ALS2; STEX; FUS; TARDBP; VEGF (VEGF-a; VEGF-b; VEGF-c).

Examples of genes for which a translatable molecule can be used to express the corresponding peptide or protein include: Drug addiction, Prkce (alcohol); Drd2; Drd4; ABAT (alcohol); GRIA2; Grm5; Grin1; Htr1b; Grin2a; Drd3; Pdyn; Gria1 (alcohol).

Examples of genes for which a translatable molecule can be used to express the corresponding peptide or protein include: Autism, Mecp2; BZRAP1; MDGA2; Sema5A; Neurexin 1; Fragile X (FMR2 (AFF2); FXR1; FXR2; Mglur5).

Examples of genes for which a translatable molecule can be used to express the corresponding peptide or protein include: Alzheimer's Disease, E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP.

Examples of genes for which a translatable molecule can be used to express the corresponding peptide or protein include: Inflammation, 1L-10; IL-1 (1L-1a; IL-1b); 1L-13; IL-17 (IL-17a (CTLA8); IL-17b; IL-17c; IL-17d; IL-17f); Il-23; Cx3er1; ptpn22; TNFa; NOD2/CARD15 for IBD; IL-6; 1L-12 (1L-12a; 1L-12b); CTLA4; Cx3cl1.

Examples of genes for which a translatable molecule can be used to express the corresponding peptide or protein include: Parkinson's Disease, x-Synuclein; DJ-1; LRRK2; Parkin; PINK1.

Examples of genes for which a translatable molecule can be used to express the corresponding peptide or protein include: Blood and coagulation diseases and disorders, Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9 Factor IX, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); *Thalassemia* (HBA2, HBB, HBD, LCRB, HBA1).

Examples of genes for which a translatable molecule can be used to express the corresponding peptide or protein include: Cell dysregulation and oncology diseases and disorders, B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF 1, ERYF1, NFE1, ABL1, NQ01, DIA4, NMOR1, NUP214, D9S46E, CAN, CAIN).

Examples of genes for which a translatable molecule can be used to express the corresponding peptide or protein include: Inflammation and immune related diseases and disorders, AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immuno-deficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immuno-deficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f, I1-23, Cx3cr1, ptpn22, TNFa, NOD2/CARD15 for IBD, IL-6, IL-12 (IL-12a, IL-12b), CTLA4, Cx3c11); Severe combined immunodeficiencies (SCIDs) (JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4).

Examples of genes for which a translatable molecule can be used to express the corresponding peptide or protein include: Metabolic, liver, kidney and protein diseases and disorders, Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, BG213071, ABCC7, CF, MRP7); Glycogen storage diseases (SLC2A2, GLUT2, G6PC, G6PT, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepato-blastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63).

Examples of genes for which a translatable molecule can be used to express the corresponding peptide or protein include: Lipoprotein lipase, APOA1, APOC3 and APOA4.

Examples of genes for which a translatable molecule can be used to express the corresponding peptide or protein include: Muscular/skeletal diseases and disorders, Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facio-scapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1).

Examples of genes for which a translatable molecule can be used to express the corresponding peptide or protein include: Neurological and neuronal diseases and disorders, ALS (SOD1, ALS2, STEX, FUS, TARDBP, VEGF (VEGF-a, VEGF-b, VEGF-c); Alzheimer's Disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizo-phrenia (Neuregulin1 (Nrg1), Erb4 (receptor for Neuregulin), Complexin1 (Cplx1), Tph1 Trypto-phan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Dis-orders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP—global instability), VLDLR (Alzheimer's), Atxn7, Atxn10).

Examples of genes for which a translatable molecule can be used to express the corresponding peptide or protein include: Occular diseases and disorders, Age-related macular degeneration (Aber, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2).

Examples of genes for which a translatable molecule can be used to express the corresponding peptide or protein include: Epilepsy, myoclonic, EPM2A, MELF, EPM2 Lafora type, 254780 Epilepsy, myoclonic, NHLRC1, EPM2A, EPM2B Lafora type, 254780.

Examples of genes for which a translatable molecule can be used to express the corresponding peptide or protein include: Duchenne muscular DMD, BMD dystrophy, 310200 (3) AIDS, delayed/rapid KIR3DL1, NKAT3, NKB1, AMB11, KIR3DS1 progression to (3).

Examples of genes for which a translatable molecule can be used to express the corresponding peptide or protein include: AIDS, delayed/rapid KIR3DL1, NKAT3, NKB1, AMB11, KIR3DS1 progression to (3) AIDS, rapid IFNG progression to, 609423 (3) AIDS, resistance to CXCL12, SDF1 (3).

Examples of genes for which a translatable molecule can be used to express the corresponding peptide or protein include: Alpha-1-Antitrypsin Deficiency, SERPINA1 [serpin peptidase inhibitor, Glade A (alpha-1 antiproteinase, antitrypsin), member 1]; SERPINA2 [serpin peptidase inhibitor, Glade A (alpha-1 antiproteinase, antitrypsin), member 2]; SERPINA3 [serpin peptidase inhibitor, Glade A (alpha-1 antiproteinase, antitrypsin), member 3]; SERPINA5 [serpin peptidase inhibitor, Glade A (alpha-1 antiproteinase, antitrypsin), member 5]; SERPINA6 [serpin peptidase inhibitor, Glade A (alpha-1 antiproteinase, antitrypsin), member 6]; SERPINA7 [serpin peptidase inhibitor, Glade A (alpha-1 antiproteinase, antitrypsin), member 7];" AND "SERPLNA6 (serpin peptidase inhibitor, Glade A (alpha-1 antiproteinase, antitrypsin), member 6).

Examples of genes for which a translatable molecule can be used to express the corresponding peptide or protein include: PI3K/AKT Signaling, PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1.

Examples of genes for which a translatable molecule can be used to express the corresponding peptide or protein include: ERK/MAPK Signaling, PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK.

Examples of genes for which a translatable molecule can be used to express the corresponding peptide or protein include: Serine/Threonine-Protein Kinase, CDK16; PCTK1; CDK5R1.

Examples of genes for which a translatable molecule can be used to express the corresponding peptide or protein include: Glucocorticoid Receptor Signaling, RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MN/11$^3$1; STAT1; IL6; HSP90AA1.

Examples of genes for which a translatable molecule can be used to express the corresponding peptide or protein include: Axonal Guidance Signaling, PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA.

Examples of genes for which a translatable molecule can be used to express the corresponding peptide or protein include: Ephrin Receptor Signaling, PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK.

Examples of genes for which a translatable molecule can be used to express the corresponding peptide or protein include: Actin Cytoskeleton Signaling, ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK.

Examples of genes for which a translatable molecule can be used to express the corresponding peptide or protein include: Huntington's Disease Signaling, PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A;

PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3.

Examples of genes for which a translatable molecule can be used to express the corresponding peptide or protein include: Apoptosis Signaling, PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1.

Examples of genes for which a translatable molecule can be used to express the corresponding peptide or protein include: B Cell Receptor Signaling, RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1.

Examples of genes for which a translatable molecule can be used to express the corresponding peptide or protein include: Leukocyte Extravasation Signaling, ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9.

Examples of genes for which a translatable molecule can be used to express the corresponding peptide or protein include: Integrin Signaling, ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3.

Examples of genes for which a translatable molecule can be used to express the corresponding peptide or protein include: Acute Phase Response Signaling, IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6.

Examples of genes for which a translatable molecule can be used to express the corresponding peptide or protein include: PTEN Signaling, ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1.

Examples of genes for which a translatable molecule can be used to express the corresponding peptide or protein include: p53 Signaling, PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; RIK3R1; RRM2B; APAF1; CTNNB1; SIRT1; CCND1; PRKDC; ATM; SFN; CDKN2A; JUN; SNAI2; GSK3B; BAX; AKT3.

Examples of genes for which a translatable molecule can be used to express the corresponding peptide or protein include: Aryl Hydrocarbon Receptor Signaling, HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1.

Examples of genes for which a translatable molecule can be used to express the corresponding peptide or protein include: Xenobiotic Metabolism Signaling, PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1.

Examples of genes for which a translatable molecule can be used to express the corresponding peptide or protein include: SAPK/JNK Signaling, PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK.

Examples of genes for which a translatable molecule can be used to express the corresponding peptide or protein include: PPAr/RXR Signaling, PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ.

Examples of genes for which a translatable molecule can be used to express the corresponding peptide or protein include: NF-KB Signaling, IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1.

Examples of genes for which a translatable molecule can be used to express the corresponding peptide or protein include: Neuregulin Signaling, ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1.

Examples of genes for which a translatable molecule can be used to express the corresponding peptide or protein include: Wnt & Beta catenin Signaling, CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2.

Examples of genes for which a translatable molecule can be used to express the corresponding peptide or protein include: Insulin Receptor Signaling, PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1.

Examples of genes for which a translatable molecule can be used to express the corresponding peptide or protein include: IL-6 Signaling, HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6.

Examples of genes for which a translatable molecule can be used to express the corresponding peptide or protein include: Hepatic Cholestasis, PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6.

Examples of genes for which a translatable molecule can be used to express the corresponding peptide or protein include: IGF-1 Signaling, IGF1; PRKCZ; ELK1; MAPK1; PTPN11; NEDD4; AKT2; PIK3CA; PRKCI; PTK2; FOS; PIK3CB; PIK3C3; MAPK8; 1GF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RP S6KB1.

Examples of genes for which a translatable molecule can be used to express the corresponding peptide or protein include: NRF2-mediated Oxidative Stress Response, PRKCE; EP300; SOD2; PRKCZ; MAPK1; SQSTM1; NQO1; PIK3CA; PRKC1; FOS; PIK3CB; P1K3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1.

Examples of genes for which a translatable molecule can be used to express the corresponding peptide or protein include: Hepatic, Fibrosis/Hepatic Stellate Cell Activation, EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMPI; STAT1; IL6; CTGF; MMP9.

Examples of genes for which a translatable molecule can be used to express the corresponding peptide or protein include: PPAR Signaling, EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1.

Examples of genes for which a translatable molecule can be used to express the corresponding peptide or protein include: Fc Epsilon RI Signaling, PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA.

Examples of genes for which a translatable molecule can be used to express the corresponding peptide or protein include: G-Protein Coupled Receptor Signaling, PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA.

Examples of genes for which a translatable molecule can be used to express the corresponding peptide or protein include: Inositol Phosphate Metabolism, PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK.

Examples of genes for which a translatable molecule can be used to express the corresponding peptide or protein include: PDGF Signaling, EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2.

Examples of genes for which a translatable molecule can be used to express the corresponding peptide or protein include: VEGF Signaling, ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA.

Examples of genes for which a translatable molecule can be used to express the corresponding peptide or protein include: Natural Killer Cell Signaling, PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA.

Examples of genes for which a translatable molecule can be used to express the corresponding peptide or protein include: Cell Cycle: G1/S Checkpoint Regulation, HDAC4;

SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6.

Examples of genes for which a translatable molecule can be used to express the corresponding peptide or protein include: T Cell Receptor Signaling, RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3.

Examples of genes for which a translatable molecule can be used to express the corresponding peptide or protein include: Death Receptor Signaling, CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3.

Examples of genes for which a translatable molecule can be used to express the corresponding peptide or protein include: FGF Signaling RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF.

Examples of genes for which a translatable molecule can be used to express the corresponding peptide or protein include: GM-CSF Signaling, LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1.

Examples of genes for which a translatable molecule can be used to express the corresponding peptide or protein include: Amyotrophic Lateral Sclerosis Signaling, BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3.

Examples of genes for which a translatable molecule can be used to express the corresponding peptide or protein include: JAK/Stat Signaling, PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1.

Examples of genes for which a translatable molecule can be used to express the corresponding peptide or protein include: Nicotinate and Nicotinamide Metabolism, PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK.

Examples of genes for which a translatable molecule can be used to express the corresponding peptide or protein include: Chemokine Signaling, CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA.

Examples of genes for which a translatable molecule can be used to express the corresponding peptide or protein include: IL-2 Signaling, ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A: LCK; RAF1; MAP2K2; JAK1; AKT1; PIK3R1; MAP2K1; JUN; AKT3.

Examples of genes for which a translatable molecule can be used to express the corresponding peptide or protein include: Synaptic Long Term Depression, PRKCE; IGF1; PRKCZ; PRDX6; LYN; MAPK1; GNAS; PRKC1; GNAQ; PPP2R1A; IGF1R; PRKID1; MAPK3; KRAS; GRN; PRKCD; NOS3; NOS2A; PPP2CA; YWHAZ; RAF1; MAP2K2; PPP2R5C; MAP2K1; PRKCA.

Examples of genes for which a translatable molecule can be used to express the corresponding peptide or protein include: Estrogen Receptor Signaling, TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2.

Examples of genes for which a translatable molecule can be used to express the corresponding peptide or protein include: Protein Ubiquitination Pathway, TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USPS; USP1; VHL; HSP90AA1; BIRC3.

Examples of genes for which a translatable molecule can be used to express the corresponding peptide or protein include: IL-10 Signaling, TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6.

Examples of genes for which a translatable molecule can be used to express the corresponding peptide or protein include: VDR/RXR Activation, PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA.

Examples of genes for which a translatable molecule can be used to express the corresponding peptide or protein include: TGF-beta Signaling, EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5.

Examples of genes for which a translatable molecule can be used to express the corresponding peptide or protein include: Toll-like Receptor Signaling, IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN Examples of genes for which a translatable molecule can be used to express the corresponding peptide or protein include: p38 MAPK Signaling, HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1.

Examples of genes for which a translatable molecule can be used to express the corresponding peptide or protein include: Neurotrophin/TRK Signaling, NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4.

Examples of genes for which a translatable molecule can be used to express the corresponding peptide or protein include: FXR/RXR Activation, INS; PPARA; FASN; RXRA; AKT2; SDC1; MAPK8; APOB; MAPK10; PPARG;

MTTP; MAPK9; PPARGC1A; TNF; CREBBP; AKT1; SREBF1; FGFR4; AKT3; FOXO1.

Examples of genes for which a translatable molecule can be used to express the corresponding peptide or protein include: Synaptic Long Term Potentiation, PRKCE; RAP1A; EP300; PRKCZ; MAPK1; CREB1; PRKC1; GNAQ; CAMK2A; PRKD1; MAPK3; KRAS; PRKCD; PPP1CC; RAF1; CREBBP; MAP2K2; MAP2K1; ATF4; PRKCA.

Examples of genes for which a translatable molecule can be used to express the corresponding peptide or protein include: Calcium Signaling, RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6.

Examples of genes for which a translatable molecule can be used to express the corresponding peptide or protein include: EGF Signaling, ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1.

Examples of genes for which a translatable molecule can be used to express the corresponding peptide or protein include: Hypoxia Signaling in the Cardiovascular System, EDN1; PTEN; EP300; NQO1; UBE21; CREB1; ARNT; HIF1A; SLC2A4; NOS3; TP53; LDHA; AKT1; ATM; VEGFA; JUN; ATF4; VHL; HSP90AA1.

Examples of genes for which a translatable molecule can be used to express the corresponding peptide or protein include: LPS/IL-1 Mediated Inhibition of RXR Function, IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1.

Examples of genes for which a translatable molecule can be used to express the corresponding peptide or protein include: LXR/RXR Activation, FASN; RXRA; NCOR2; ABCA1; NFKB2; IRF3; RELA; NOS2A; TLR4; TNF; RELB; LDLR; NR1H2; NEKB1; SREBF1; IL1R1; CCL2; IL6; MMP9.

Examples of genes for which a translatable molecule can be used to express the corresponding peptide or protein include: Amyloid Processing, PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP.

Examples of genes for which a translatable molecule can be used to express the corresponding peptide or protein include: IL-4 Signaling, AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1.

Examples of genes for which a translatable molecule can be used to express the corresponding peptide or protein include: Cell Cycle: G2/M DNA Damage Checkpoint Regulation, EP300; PCAF; BRCA1; GADD45A; PLK1; BTRC; CHEK1; ATR; CHEK2; YWHAZ; TP53; CDKN1A; PRKDC; ATM; SFN; CDKN2A.

Examples of genes for which a translatable molecule can be used to express the corresponding peptide or protein include: Nitric Oxide Signaling in the Cardiovascular System, KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1.

Examples of genes for which a translatable molecule can be used to express the corresponding peptide or protein include: Purine Metabolism NME2; SMARCA4; MYH9; RRM2; ADAR; EIF2AK4; PKM2; ENTPD1; RAD51; RRM2B; TJP2; RAD51C; NT5E; POLD1; NME1.

Examples of genes for which a translatable molecule can be used to express the corresponding peptide or protein include: cAMP-mediated Signaling, RAP1A; MAPK1; GNAS; CREB1; CAMK2A; MAPK3; SRC; RAF1; MAP2K2; STAT3; MAP2K1; BRAF; ATF4.

Examples of genes for which a translatable molecule can be used to express the corresponding peptide or protein include: Mitochondrial Dysfunction Notch Signaling, SOD2; MAPK8; CASP8; MAPK10; MAPK9; CASP9; PARK7; PSEN1; PARK2; APP; CASP3 HES1; JAG1; NUMB; NOTCH4; ADAM17; NOTCH2; PSEN1; NOTCH3; NOTCH1; DLL4.

Examples of genes for which a translatable molecule can be used to express the corresponding peptide or protein include: Endoplasmic Reticulum Stress Pathway, HSPA5; MAPK8; XBP1; TRAF2; ATF6; CASP9; ATF4; EIF2AK3; CASP3.

Examples of genes for which a translatable molecule can be used to express the corresponding peptide or protein include: Pyrimidine Metabolism, NME2; AICDA; RRM2; EIF2AK4; ENTPD1; RRM2B; NT5E; POLD1; NME1.

Examples of genes for which a translatable molecule can be used to express the corresponding peptide or protein include: Parkinson's Signaling, UCHL1; MAPK8; MAPK13; MAPK14; CASP9; PARK7; PARK2; CASP3.

Examples of genes for which a translatable molecule can be used to express the corresponding peptide or protein include: Cardiac & Beta Adrenergic Signaling, GNAS; GNAQ; PPP2R1A; GNB2L1; PPP2CA; PPP1CC; PPP2R5C.

Examples of genes for which a translatable molecule can be used to express the corresponding peptide or protein include: Glycolysis/Gluco-neogenesis, HK2; GCK; GPI; ALDH1A1; PKM2; LDHA; HK1.

Examples of genes for which a translatable molecule can be used to express the corresponding peptide or protein include: Interferon Signaling, IRF1; SOCS1; JAK1; JAK2; IFITM1; STAT1; IFIT3.

Examples of genes for which a translatable molecule can be used to express the corresponding peptide or protein include: Sonic Hedgehog Signaling, ARRB2; SMO; GLI2; DYRK1A; GLI1; GSK3B; DYRKIB.

Examples of genes for which a translatable molecule can be used to express the corresponding peptide or protein include: Glycerophospholipid Metabolism, PLD1; GRN; GPAM; YWHAZ; SPHK1; SPHK2.

Examples of genes for which a translatable molecule can be used to express the corresponding peptide or protein include: Phospholipid Degradation, PRDX6; PLD1; GRN; YWHAZ; SPHK1; SPHK2.

Examples of genes for which a translatable molecule can be used to express the corresponding peptide or protein include: Tryptophan Metabolism, SIAH2; PRMT5; NEDD4; ALDH1A1; CYP1B1; SIAH1.

Examples of genes for which a translatable molecule can be used to express the corresponding peptide or protein include: Lysine Degradation, SUV39H1; EHMT2; NSD1; SETD7; PPP2R5C.

Examples of genes for which a translatable molecule can be used to express the corresponding peptide or protein include: Nucleotide Excision, ERCC5; ERCC4; XPA; XPC; ERCC1.

Examples of genes for which a translatable molecule can be used to express the corresponding peptide or protein include: Repair Pathway Starch and Sucrose Metabolism, UCHL1; HK2; GCK; GPI; HK1.

Examples of genes for which a translatable molecule can be used to express the corresponding peptide or protein include: Aminosugars Metabolism, NQO1; HK2; GCK; HK1.

Examples of genes for which a translatable molecule can be used to express the corresponding peptide or protein include: Arachidonic Acid Metabolism, PRDX6; GRN; YWHAZ; CYP1B1.

Examples of genes for which a translatable molecule can be used to express the corresponding peptide or protein include: Circadian Rhythm Signaling, CSNK1E; CREB1; ATF4; NR1D1.

Examples of genes for which a translatable molecule can be used to express the corresponding peptide or protein include: Coagulation System, BDKRB1; F2R; SERPINE1; F3.

Examples of genes for which a translatable molecule can be used to express the corresponding peptide or protein include: Dopamine Receptor Signaling, PPP2R1A; PPP2CA; PPP1CC; PPP2R5C.

Examples of genes for which a translatable molecule can be used to express the corresponding peptide or protein include: Glutathione Metabolism, IDH2; GSTP1; ANPEP; IDH1.

Examples of genes for which a translatable molecule can be used to express the corresponding peptide or protein include: Glycerolipid Metabolism, ALDH1A1; GPAM; SPHK1; SPHK2.

Examples of genes for which a translatable molecule can be used to express the corresponding peptide or protein include: Linoleic Acid Metabolism, PRDX6; GRN; YWHAZ; CYP1B1.

Examples of genes for which a translatable molecule can be used to express the corresponding peptide or protein include: Methionine Metabolism, DNMT1; DNMT3B; AHCY; DNMT3A.

Examples of genes for which a translatable molecule can be used to express the corresponding peptide or protein include: Pyruvate Metabolism, GLO1; ALDH1A1; PKM2; LDHA.

Examples of genes for which a translatable molecule can be used to express the corresponding peptide or protein include: Arginine and Proline Metabolism, ALDH1A1; NOS3; NOS2A.

Examples of genes for which a translatable molecule can be used to express the corresponding peptide or protein include: Eicosanoid Signaling, PRDX6; GRN; YWHAZ.

Examples of genes for which a translatable molecule can be used to express the corresponding peptide or protein include: Fructose and Mannose Metabolism, HK2; GCK; HK1.

Examples of genes for which a translatable molecule can be used to express the corresponding peptide or protein include: Galactose Metabolism, HK2; GCK; HK1.

Examples of genes for which a translatable molecule can be used to express the corresponding peptide or protein include: Stilbene, Coumarine and Lignin Biosynthesis, PRDX6; PRDX1; TYR.

Examples of genes for which a translatable molecule can be used to express the corresponding peptide or protein include: Antigen Presentation Pathway, CALR; B2M.

Examples of genes for which a translatable molecule can be used to express the corresponding peptide or protein include: Biosynthesis of Steroids, NQO1; DHCR7.

Examples of genes for which a translatable molecule can be used to express the corresponding peptide or protein include: Butanoate Metabolism, ALDH1A1; NLGN1.

Examples of genes for which a translatable molecule can be used to express the corresponding peptide or protein include: Citrate Cycle, IDH2; IDH1.

Examples of genes for which a translatable molecule can be used to express the corresponding peptide or protein include: Fatty Acid Metabolism, ALDH1A1; CYP1B1.

Examples of genes for which a translatable molecule can be used to express the corresponding peptide or protein include: Glycerophospholipid Metabolism, PRDX6; CHKA.

Examples of genes for which a translatable molecule can be used to express the corresponding peptide or protein include: Histidine Metabolism, PRMT5; ALDH1A1.

Examples of genes for which a translatable molecule can be used to express the corresponding peptide or protein include: Inositol Metabolism, ERO1L; APEX1.

Examples of genes for which a translatable molecule can be used to express the corresponding peptide or protein include: Metabolism of Xenobiotics by Cytochrome p450, GSTP1; CYP1B1.

Examples of genes for which a translatable molecule can be used to express the corresponding peptide or protein include: Methane Metabolism, PRDX6; PRDX1.

Examples of genes for which a translatable molecule can be used to express the corresponding peptide or protein include: Phenylalanine Metabolism, PRDX6; PRDX1.

Examples of genes for which a translatable molecule can be used to express the corresponding peptide or protein include: Propanoate Metabolism, ALDH1A1; LDHA.

Examples of genes for which a translatable molecule can be used to express the corresponding peptide or protein include: Selenoamino Acid Metabolism, PRMT5; AHCY.

Examples of genes for which a translatable molecule can be used to express the corresponding peptide or protein include: Sphingolipid Metabolism, SPHK1; SPHK2.

Examples of genes for which a translatable molecule can be used to express the corresponding peptide or protein include: Aminophosphonate Metabolism, PRMT5.

Examples of genes for which a translatable molecule can be used to express the corresponding peptide or protein include: Androgen and Estrogen Metabolism, PRMT5.

Examples of genes for which a translatable molecule can be used to express the corresponding peptide or protein include: Ascorbate and Aldarate Metabolism, ALDH1A1.

Examples of genes for which a translatable molecule can be used to express the corresponding peptide or protein include: Bile Acid Biosynthesis, ALDH1A1.

Examples of genes for which a translatable molecule can be used to express the corresponding peptide or protein include: Cysteine Metabolism, LDHA.

Examples of genes for which a translatable molecule can be used to express the corresponding peptide or protein include: Fatty Acid Biosynthesis, FASN.

Examples of genes for which a translatable molecule can be used to express the corresponding peptide or protein include: Glutamate Receptor Signaling, GNB2L1.

Examples of genes for which a translatable molecule can be used to express the corresponding peptide or protein include: NRF2-mediated Oxidative Stress Response, PRDX1.

Examples of genes for which a translatable molecule can be used to express the corresponding peptide or protein include: Pentose Phosphate Pathway, GPI.

Examples of genes for which a translatable molecule can be used to express the corresponding peptide or protein include: Pentose and Glucuronate Interconversions, UCHL1.

Examples of genes for which a translatable molecule can be used to express the corresponding peptide or protein include: Retinol Metabolism, ALDH1A1.

Examples of genes for which a translatable molecule can be used to express the corresponding peptide or protein include: Riboflavin Metabolism, TYR.

Examples of genes for which a translatable molecule can be used to express the corresponding peptide or protein include: Tyrosine Metabolism, PRMT5, TYR.

Examples of genes for which a translatable molecule can be used to express the corresponding peptide or protein include: Ubiquinone Biosynthesis, PRMT5.

Examples of genes for which a translatable molecule can be used to express the corresponding peptide or protein include: Valine, Leucine and Isoleucine Degradation, ALDH1A1.

Examples of genes for which a translatable molecule can be used to express the corresponding peptide or protein include: Glycine, Serine and Threonine Metabolism, CHKA.

Examples of genes for which a translatable molecule can be used to express the corresponding peptide or protein include: Lysine Degradation, ALDH1A1.

Examples of genes for which a translatable molecule can be used to express the corresponding peptide or protein include: Pain/Taste, TRPM5; TRPA1.

Examples of genes for which a translatable molecule can be used to express the corresponding peptide or protein include: Pain, TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a.

Examples of genes for which a translatable molecule can be used to express the corresponding peptide or protein include: Mitochondrial Function, AIF; CytC; SMAC (Diablo); Aifm-1; Aifm-2.

Examples of genes for which a translatable molecule can be used to express the corresponding peptide or protein include: Developmental Neurology, BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln.

Pharmaceutical Compositions

In some aspects, this invention provides pharmaceutical compositions containing a translatable compound and a pharmaceutically acceptable carrier.

A pharmaceutical composition can be capable of local or systemic administration. In some aspects, a pharmaceutical composition can be capable of any modality of administration. In certain aspects, the administration can be by any route, including intravenous, subcutaneous, pulmonary, intramuscular, intraperitoneal, dermal, oral, inhalation or nasal administration.

Embodiments of this invention include pharmaceutical compositions containing a translatable compound in a lipid formulation.

In some embodiments, a pharmaceutical composition may comprise one or more lipids selected from cationic lipids, ionizable lipids, anionic lipids, sterols, pegylated lipids, and any combination of the foregoing. In some embodiments, the pharmaceutical composition containing a translatable compound comprises a cationic lipid, a phospholipid, cholesterol, and a pegylated lipid.

In certain embodiments, a pharmaceutical composition can be substantially free of liposomes.

In further embodiments, a pharmaceutical composition can include nanoparticles.

Lipid-based formulations have been increasingly recognized as one of the most promising delivery systems for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and to deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin R A-shRNA). Cationic lipids, such as DOTAP, (1,2-dioleoyl-3-trimethylammonium-propane) and DOTMA (N-[1-(2,3-dioleoyloxy)propyl]-N,N,N-trimethyl-ammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv Rev. 2014 February; 66: 110-116.).

According to some embodiments, the expressible polynucleotides and heterologous mRNA constructs described herein are lipid formulated. The lipid formulation is preferably selected from, but not limited to, liposomes, lipoplexes, copolymers, such as PLGA, and lipid nanoparticles.

In one preferred embodiment, a lipid nanoparticle (LNP) comprises:

(a) a nucleic acid,
(b) a cationic or ionizable lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

In one embodiment, the lipid nanoparticle formulation consists of (i) at least one cationic lipid; (ii) a neutral lipid; (iii) a sterol, e.g., cholesterol; and (iv) a PEG-lipid, in a molar ratio of about 20-60% cationic lipid: 5-25% neutral lipid: 25-55% sterol; 0.5-15% PEG-lipid.

All acid and base salts of the compounds described herein are intended to be included within the scope of this invention. A compound may exist in an unsolvated or solvated form, including hydrated forms. In general, the solvated forms, with pharmaceutically acceptable solvents such as water, ethanol, and the like, are equivalent to the unsolvated forms for the purposes of this disclosure. Compounds, salts, and solvates thereof, may exist in a tautomeric form, for example, as an amide or imino ether. All tautomeric forms are included in this invention.

The cationic lipid compounds described herein may be combined with a translatable compound of the invention to form microparticles, nanoparticles, liposomes, or micelles. The translatable compound of the invention to be delivered by the particles, liposomes, or micelles may be in the form of a gas, liquid, or solid. The cationic lipid compound and the translatable compound may be combined with other cationic lipid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5 to 10% phospholipid, and 1-10% PEG. The composition may contain 60-70% cationic lipid compound, 25-35% cholesterol, and 5-10% PEG. The composition may contain up to 90% cationic lipid compound and 2 to 15% helper lipid. The formulation may be a lipid particle formulation, for example containing 8-30% compound, 5-30% helper lipid, and 0-20% cholesterol; 4-25% cationic lipid, 4-25% helper lipid, 2 to 25% cholesterol, 10 to 35% cholesterol-PEG, and 5% cholesterol-amine; or 2-30% cationic lipid, 2-30% helper lipid, 1 to 15% cholesterol, 2 to 35% cholesterol-PEG, and 1-20% cholesterol-amine; or up to 90% cationic lipid and 2-10% helper lipids, or even 100% cationic lipid.

In some embodiments, the one or more cholesterol-based lipids are selected from cholesterol, PEGylated cholesterol and DC-Chol (N,N-dimethyl-N-ethylcarboxamidocholesterol), and 1,4-bis(3-N-oleylamino-propyl)piperazine. In an exemplary embodiment, the cholesterol-based lipid is cholesterol.

In some embodiments, the one or more pegylated lipids, i.e., PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K. In an exemplary embodiment, the PEG-modified lipid is PEGylated cholesterol.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions and methods are described, for example, in Remington's Pharmaceutical Sciences, Mack Publishing Co. (A.R. Gennaro ed. 1985), and Remington, The Science and Practice of Pharmacy, 21st Edition (2005).

Examples of excipients for a pharmaceutical composition include antioxidants, suspending agents, dispersing agents, preservatives, buffering agents, tonicity agents, and surfactants.

An effective dose of an agent or pharmaceutical formulation of this invention can be an amount that is sufficient to cause translation of a translatable molecule in a cell.

A therapeutically effective dose can be an amount of an agent or formulation that is sufficient to cause a therapeutic effect. A therapeutically effective dose can be administered in one or more separate administrations, and by different routes. As will be appreciated in the art, a therapeutically effective dose or a therapeutically effective amount is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating a disease, indication or symptom). For example, a therapeutically effective amount may be an amount sufficient to achieve a desired therapeutic and/or prophylactic effect. Generally, the amount of a therapeutic agent (e.g., a translatable oligomer) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective dose of an active agent, e.g., a translatable oligomer, in vivo can be a dose of about 0.001 to about 500 mg/kg body weight. For instance, the therapeutically effective dose may be about 0.001-0.01 mg/kg body weight, or 0.01-0.1 mg/kg, or 0.1-1 mg/kg, or 1-10 mg/kg, or 10-100 mg/kg. In some embodiments, a translatable oligomer can be provided at a dose ranging from about 0.1 to about 10 mg/kg body weight, e.g., from about 0.5 to about 5 mg/kg, from about 1 to about 4.5 mg/kg, or from about 2 to about 4 mg/kg.

A therapeutically effective dose of an active agent, e.g., a translatable oligomer, in vivo can be a dose of at least about 0.001 mg/kg body weight, or at least about 0.01 mg/kg, or at least about 0.1 mg/kg, or at least about 1 mg/kg, or at least about 2 mg/kg, or at least about 3 mg/kg, or at least about 4 mg/kg, or at least about 5 mg/kg, at least about 10 mg/kg, at least about 20 mg/kg, at least about 50 mg/kg, or more. In some embodiments, a translatable oligomer can be provided at a dose of about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 5 mg/kg, or about 6, 7, 8, 9, 10, 15, 20, 25, 50, 75, or 100 mg/kg.

Nucleobase sequences shown herein are from left to right, 5' to 3', unless stated otherwise.

Thiocarbamate and Carbamate-Containing Ionizable Lipid Formulations

Some examples of ionizable lipids and lipid compositions for delivery of an active molecule of this invention are given in WO/2015/074085 and U.S. patent application Ser. No. 15/387,067, each of which is hereby incorporated by reference in its entirety.

In certain embodiments, the lipid is a compound of the following formula:

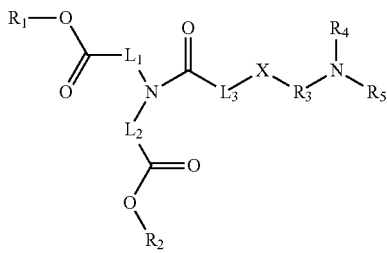

wherein $R_1$ and $R_2$ both consist of a linear or branched alkyl consisting of 1 to 14 carbons, or an alkenyl or alkynyl consisting of 2 to 14 carbons;

$L_1$ and $L_2$ both consist of a linear alkylene or alkenylene consisting of 5 to 18 carbons, or forming a heterocycle with N;

X is S;

$L_3$ consists of a bond or a linear alkylene consisting of 1 to 6 carbons, or forming a heterocycle with N;

$R_3$ consists of a linear or branched alkylene consisting of 1 to 6 carbons; and $R_4$ and $R_5$ are the same or different, each consisting of a hydrogen or a linear or branched alkyl consisting of 1 to 6 carbons;

or a pharmaceutically acceptable salt thereof.

A lipid formulation may contain one or more ionizable cationic lipids selected from ATX-001 to ATX-032, as disclosed in WO/2015/074085.

A lipid formulation may contain one or more ionizable cationic lipids selected from ATX-0081, ATX-0095, ATX-0102, and ATX-0126, as disclosed in U.S. patent application Ser. No. 15/387,067, and shown in Table 6.

TABLE 6

| Ionizable cationic lipids | |
|---|---|
| No. | Structure |
| ATX-0081 | |
| ATX-0095 | |

TABLE 6-continued

Ionizable cationic lipids

| No. | Structure |
|---|---|
| ATX-0102 | 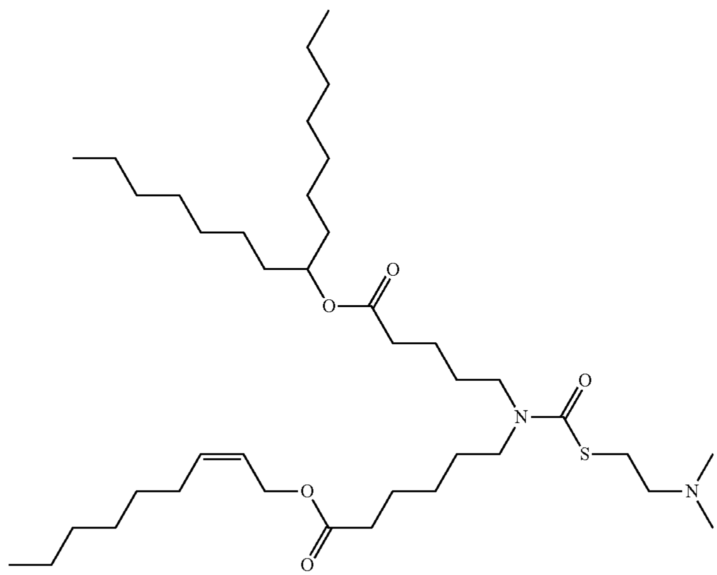 [SMILES: CCCCCC/C=C\COC(=O)CCCCCN(CCCCC(=O)OC(CCCCCCC)CCCCCCC)C(=O)SCCN(C)C] |
| ATX-0126 | 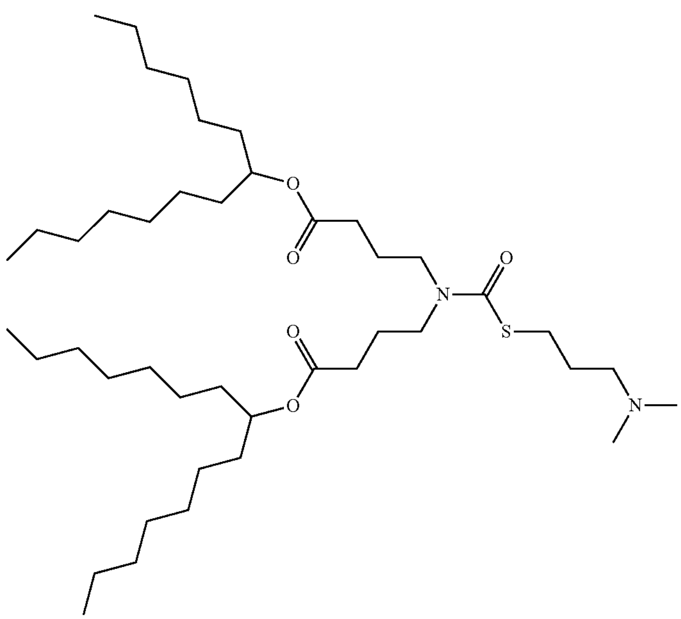 [SMILES: CCCCCCCC(CCCCCC)OC(=O)CCCN(CCCC(=O)OC(CCCCCCC)CCCCCCC)C(=O)SCCCN(C)C] |

Cationic Lipids

The lipid nanoparticle preferably includes a cationic lipid suitable for forming a lipid nanoparticle. Preferably, the cationic lipid carries a net positive charge at about physiological pH.

The cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DM A), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination of any of the foregoing. Other cationic lipids include, but are not limited to, N,N-distearyl-N,N-dimethylammonium bromide (DDAB), 3P-(N-(N',N'-dimethylaminoethane)-carbamoyl)cholesterol (DC-Choi), N-(1-(2,3-dioleyloxy)propyl)-N-2-(sperminecarboxamido)ethyl)-N,N-dimethylammoniumtrifluoroacetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL)

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al, PNAS, 107(5), 1864-69, 2010. Other suitable amino lipids include those having alternative fatty acid groups and other dialkylamino groups, including those, in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In a further preferred embodiment, the LNP comprises the cationic lipid with formula (III) according to the patent application PCT/EP2017/064066. In this context, the disclosure of PCT/EP2017/064066 is also incorporated herein by reference.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention. In certain embodiments, the protonatable lipids have a pKa of the protonatable group in the range of about 4 to about 11, e.g., a pKa of about 5 to about 7.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the particle. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle). In one embodiment, the ratio of cationic lipid to nucleic acid is from about 3 to about 15, such as from about 5 to about 13 or from about 7 to about 11.

Non-Cationic Lipids

The non-cationic lipid can be a neutral lipid, an anionic lipid, or an amphipathic lipid. Neutral lipids, when present, can be any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., lipid particle size and stability of the lipid particle in the bloodstream. Preferably, the neutral lipid is a lipid having two acyl groups (e.g. diacylphosphatidylcholine and diacylphosphatidylethanolamine). In one embodiment, the neutral lipids contain saturated fatty acids with carbon chain lengths in the range of CIO to C20. In another embodiment, neutral lipids with mono or diunsaturated fatty acids with carbon chain lengths in the range of CIO to C2o are used. Additionally, neutral lipids having mixtures of saturated and unsaturated fatty acid chains can be used.

Suitable neutral lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), dimyristoyl phosphatidylcholine (D PC), distearoyl-phosphatidyl-ethanolamine (DSPE), SM, 16-O-monomethyl PE, 16-O-dimethyl PE, 18-1-trans PE, 1-stearoyl-2-oleoyl-phosphatidyethanolamine (SOPE), cholesterol, or a mixture thereof. Anionic lipids suitable for use in lipid particles of the invention include, but are not limited to, phosphatidyl lycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

The non-cationic lipid can be from about 5 mol % to about 90 mol %, about 5 mol % to about 10 mol %, about 5, 10, 15, 20, 25, 30, 35, 40, 45, 50, 55, 60, 65, 70, 75, 80, 85, or about 90 mol % of the total lipid present in the particle. In one embodiment, the lipid nanoparticles include from about 0% to about 15 or 45% on a molar basis of neutral lipid, e.g., from about 3 to about 12% or from about 5 to about 10%. For instance, the lipid nanoparticles may include about 15%, about 10%, about 7.5%, or about 7.1% of neutral lipid on a molar basis (based upon 100% total moles of lipid in the lipid nanoparticle).

Sterols

A preferred sterol is cholesterol. The sterol can be about 10 mol % to about 60 mol % or about 25 mol % to about 40 mol % of the lipid particle. In one embodiment, the sterol is about 10, 15, 20, 25, 30, 35, 40, 45, 50, 55, or about 60 mol % of the total lipid present in the lipid particle. In another embodiment, the lipid nanoparticles include from about 5% to about 50% on a molar basis of the sterol, e.g., about 15% to about 45%, about 20% to about 40%, about 48%, about 40%, about 38.5%, about 35%, about 34.4%, about 31.5% or about 31% on a molar basis (based upon 100% total moles of lipid in the lipid nanoparticle).

Aggregation Reducing Agent

The aggregation reducing agent can be a lipid capable of reducing aggregation. Examples of such lipids include, but are not limited to, polyethylene glycol (PEG)-modified lipids, monosialoganglioside Gml, and polyamide oligomers (PAO) such as those described in U.S. Pat. No. 6,320,017, which is incorporated by reference in its entirety. Other compounds with uncharged, hydrophilic, steric-barrier moieties, which prevent aggregation during formulation, like PEG, Gml or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499 and 5,885,613, each of which is incorporated by reference in its entirety.

The aggregation reducing agent may be, for example, a polyethyleneglycol (PEG)-lipid including, without limitation, a PEG-diacylglycerol (DAG), a PEG-dialkylglycerol, a PEG-dialkyloxypropyl (DAA), a PEG-phospholipid, a PEG-ceramide (Cer), or a mixture thereof (such as PEG-Cer14 or PEG-Cer20). The PEG-DAA conjugate may be, for example, a PEG-dilauryloxypropyl (C12), a PEG-dimyristyloxypropyl (C14), a PEG-dipalmityloxypropyl (C16), or a PEG-distearyloxypropyl (C18). Other pegylated-lipids include, but are not limited to, polyethylene glycol-didimyristoyl glycerol (C14-PEG or PEG-C14, where PEG has an average molecular weight of 2000 Da) (PEG-DMG); (R)-2,3-bis(octadecyloxy)propyl-1-(methoxy poly(ethylene glycol)2000)propylcarbamate) (PEG-DSG); PEG-carbamoyl-1,2-dimyristyloxypropylamine, in which PEG has an average molecular weight of 2000 Da (PEG-cDMA); N-Acetylgalactosamine-((R)-2,3-bis(octadecyloxy)propyl-1-(methoxy poly(ethylene glycol)2000)propylcarbamate)) (GalNAc-PEG-DSG); mPEG (mw2000)-diastearoylphosphatidyl-ethanolamine (PEG-DSPE); and polyethylene glycol-dipalmitoylglycerol (PEG-DPG). In one embodiment, the aggregation reducing agent is PEG-DMG. In another embodiment, the aggregation reducing agent is PEG-c-DMA.

The average molecular weight of the PEG moiety in the PEG-modified lipids can range from about 500 to about 8,000 Daltons (e.g., from about 1,000 to about 4,000 Daltons). In one preferred embodiment, the average molecular weight of the PEG moiety is about 2,000 Daltons.

The concentration of the aggregation reducing agent may range from about 0.1 to about 15 mol %, based upon the 100% total moles of lipid in the lipid particle. In one embodiment, the formulation includes less than about 3, 2, or 1 mole percent of PEG or PEG-modified lipid, based upon the total moles of lipid in the lipid particle. In another embodiment, the lipid nanoparticles include from about 0.1% to about 20% on a molar basis of the PEG-modified lipid, e.g., about 0.5 to about 10%, about 0.5 to about 5%, about 10%, about 5%, about 3.5%, about 1.5%, about 0.5%, or about 0.3% on a molar basis (based on 100% total moles of lipids in the lipid nanoparticle).

Lipid Nanoparticles (LNPs)

Preferably, lipid nanoparticles may have the structure of a liposome. A liposome is typically a structure having lipid-containing membranes enclosing an aqueous interior. Liposomes preferably have one or more lipid membranes. In preferred embodiments, liposomes can be single-layered, referred to as unilamellar, or multi-layered, referred to as multilamellar. When complexed with nucleic acids (e.g. RNA), lipid particles may also be lipoplexes, which are preferably composed of cationic lipid bilayers sandwiched between nucleic acid layers. Liposomes can further be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. In certain embodiments, liposome design may include, but is not limited to, opsonins or ligands in order to improve the attachment of liposomes to unhealthy tissue or to activate events such as, but not limited to, endocytosis. Liposomes may contain a low (e.g. an acidic) or a high (e.g. a basic) pH in order to improve the delivery of the pharmaceutical formulations.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in their entirety. In preferred embodiments, the nucleic acid (e.g. an RNA as described herein) may be encapsulated by the liposome, and/or it may be contained in an aqueous core, which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

Transfections

In some experiments, translatable messenger molecules were transfected into Hepal-6 or AML12 cells in 96 well plates. The MESSENGERMAX transfection reagent (Life Technologies) was used by manufacture instruction for all transfections. Other suitable cell lines include HEK293 and Hep3B cells.

An example transfection protocol in vitro was as follows:

Plate hepatocyte Hepa1-6 cells 5000 cells per well in 96 well plate at least 8 hours before transfection.

Replace 90 μL DMEM medium containing 10% FBS and Non-essential amino acid) adding 90 μL into each well of 96 well plate immediately before beginning the transfection experiment.

Prepare Messenger Max transfection reagent (Life Technologies) translatable molecule complex according to manufacturer's instruction.

Transfer 10 μL of the complex into a well containing the cells in the 96-well plate.

Collect the medium after desired time points and add 100 μL fresh medium into each well. Medium will be kept at −80° C. until an ELISA assay is performed using the standard manufacturer protocol.

An example of a transfection protocol in vivo was as follows:

The translatable molecule is formulated with nanoparticles.

Inject the nanoparticle-formulated translatable molecule (1 mg/kg) into BL57BL/c mice (4-6 week-old) via standard i.v. injection in the lateral tail vein.

Collect approximately 50 µL of blood in a Heparin-coated microcentrifuge tube at a suitable time post-injection.

Centrifuge at 3,000×g for 10 minutes at 4° C.

Transfer the supernatant (plasma) into a fresh microcentrifuge tube. Plasma will be kept at −80° C. until an ELISA assay is performed using the standard manufacturer protocol.

Nanoparticle Formulations

Lipid nanoparticles can be prepared containing an mRNA, using appropriate volumes of lipids in an ethanol/aqueous buffer containing the mRNA. A Nanossemblr microfluidic device can be used for this purpose, followed by downstream processing. For example, to prepare nanoparticles, a desired amount of targeted mRNA can be dissolved into 5 mM Citric Acid buffer (pH 3.5). The lipids can be dissolved at the adequate molar ratio, in ethanol. The molar percentage ratio for the constituent lipids can be, for example, 50% ionizable lipid, 7% DSPC (1,2-distearoyl-sn-glycero-3-phosphocholine; Avanti Polar Lipids), 40% cholesterol (Avanti Polar Lipids), and 3% DMG-PEG (1,2-Dimyristoyl-sn-glycerol, methoxypolyethylene glycol, PEG chain molecular weight: 2000; NOF America Corporation). Next, the lipid and mRNA solutions can be combined in the microfluidic device (Precision NanoSystems) at a flow ratio of 1:3 (ethanol:aqueous phase). The total combined flow rate can be 12 mL/min. Lipid nanoparticles can be formed and subsequently purified by overnight dialysis using a phosphate buffer in a dialysis device (Float-a-lyzer, Spectrum Labs), followed by concentration using Amicon Ultra-15 centrifugal filters (Merck Millipore). The particle size can be determined by dynamic light scattering (ZEN3600, Malvern Instruments). An "encapsulation" efficiency can be calculated by determining the un-encapsulated mRNA content measured by the fluorescence upon the addition of RiboGreen (Molecular Probes) to the LNP slurry (Fi); then, the value was compared to the total mRNA content that is obtained upon lysis of the LNPs by 1% Triton X-100 (Ft), where percentage of "encapsulation"=(Ft−Fi)/Ft×100. Encapsulation can refer to inclusion of the mRNA in the nanoparticle, regardless of form.

In-Cell Western 96-well collagen plates were used to seed the cells at the appropriate density in DMEM/FBS culture media. At the optimal confluence, cells were transfected with the targeted mRNAs diluted in the transfection reagent mix (MessengerMax and Opti-MEM). Cells were placed in the CO2 incubator and let them grow. At the desire timepoint, media was removed and cells were fixed in 4% fresh PFA for 20 min. After that, fixative was removed and cells were permeabilized in TBST for 5 minutes several times. When permeabilization washes are complete, cells were incubated with the blocking buffer for 45 min. Primary antibody was then added and incubated for 1 h at room temperature. Following that, cells were washed several times in TBST, and then incubated for 1 h with the secondary antibody diluted in blocking buffer and containing the CellTag 700 stain. To finalize, cells were washed several times in TBST followed by a last wash in TBS. Then, plate was imaged using the Licor detection system and data was normalized to the total number of cells labeled by the CellTag 700.

Generating Tail PCR Products

Plasmid DNA (10 ng) containing each mRNA expression construct can be used to generate the poly A tail 120 PCR products in a 50 µl PCR reaction with 2×KAPA HiFi PCR mix (KR0370) as per the manufacturer's instructions. The product can be then checked on a 2% gel from Life Technologies and approximately quantified based on the intensity of the low molecular weight ladder (Life Technologies, 10068-013), and cleaned with the Qiagen PCR purification kit and resuspended in 50 ul water.

In some embodiments, a linearized plasmid is used to generate a polyA tail. The plasmid can be linearized using a restriction enzyme before in vitro transcription is performed.

In Vitro Transcription (IVT) for Synthesis

The following protocol is for a 200 µl IVT reaction using NEB HiScribe T7 RNA polymerase reagents, which should yield about 1 mg of RNA. 2.5×NTP mix was prepared as required by thawing individual 100 mM NTP stocks (ATP, GTP, CTP, and UTP nucleotides, or chemically modified counterparts) and pooling them together. For the IVT reaction, about 2-4 of the template was used for a 200 µl reaction. The 10×IVT reaction buffer, the 2.5× dNTP mix, the template DNA and the T7 RNA polymerase are mixed well by pipetting and incubated at 37° C. for 4 hours. To degrade the DNA template, the IVT reaction is diluted with 700 ul of nuclease-free water and then 10× DNase I buffer and 20 ul of the RNase-free DNase I are added to the IVT mix and incubated at 37° C. for 15 minutes. The diluted (to 1 ml) and DNase treated reaction is then purified by a Qiagen RNeasy Maxi columns as per the manufacturer's instructions with a final elution in RNase-free water. The purified RNA is then quantified by UV absorbance where the A260/A280 should be about 1.8-2.2, depending on the resuspension buffer used.

Enzymatic Capping of IVT RNA

For enzymatic capping, a 50× scaled-up version of NEB's one-step capping and 2'O-methylation reaction can be used, that is suitable for treating up to 1 mg of IVT transcripts. A 10 µg RNA in a 20 µl reaction is recommended, based on the assumption that transcript length would be as short as 100 nt. However, a higher substrate-to-reaction volume is acceptable for transcripts, which can be generally longer (about 300-600 nt) in length. Before initiating the capping reaction, the RNA is denatured at 65° C. for 5 minutes and then snap chilled to relieve any secondary conformations. For the total 1 ml capping reaction, 1 mg denatured RNA in 700 µl of nuclease-free water is used along with 100 µl (10×) capping buffer, 50 µl (10 mM) GTP, 50 µl (4 mM) SAM, 50 µl of (10 U/µl). Vaccinia capping enzyme and 50 µl of mRNA cap 2'-O-methyltransferase at (50 U/µl) are combined and incubated at 37° C. for 1 hour. The resulting capped mRNA is eluted using RNASE free water, re-purified on an RNeasy column, quantified by nanodrop. The mRNA is also visualized on the gel by running 500 ng of the purified product per lane in a denaturing gel after denaturation and snap-chill to remove secondary structures.

In some embodiments, RNA capping can be performed by co-transcriptional capping during IVT.

EXAMPLES

Example 1

In Vitro Transcription Evaluation of mRNA Contructs

In vitro transcription protocol. hEPO mRNAs with all of the 5' UTR and 3' UTR combinations of Table 7 were synthesized. hEPO mRNAs were synthesized in vitro using T7RNA polymerase-mediated DNA-dependent RNA transcription where UTP was substituted with 100% N$^1$-methylpseudouracil (N1MPU), using linearized template for each UTR combination of Table 7. The double strand contamination of all mRNAs were removed using enzymatic reaction and following by silica purification.

In vitro transfection protocol. The resulted mRNAs were transfected into Hepa1-6 cells (mouse hepatoma cell line was derived from the BW7756 tumor that arose in a C57BL/6 mouse) using MESSENGER MAX transfection reagents. The cell culture medium was collected 24, 48, and 72 hrs after transfection.

hEPO production in vitro by ELISA protocol. The hEPO protein production was detected in the cell culture medium in vitro using hEPO ELISA at 24, 48, and 72 hrs. The hEPO expressions for each time point were normalized using hEPO (5'TEV-CDS-3'XbG) as a control.

Example 2

Translatable Construct Molecules for hEPO

In this example, a translatable molecule was made and used for expressing human EPO with advantageously increased efficiency of translation.

FIG. 1 shows the results of enhanced expression control for human erythropoietin (hEPO) in vitro using translatable molecules of this invention. hEPO mRNAs were synthesized in vitro using T7RNA polymerase-mediated DNA-dependent RNA transcription, where UTP was substituted with 100% N$^1$-methylpseudouracil (N1MPU), using a linearized template for each UTR combination. mRNAs were synthesized having all combinations of different 5'UTR and 3'UTR of Table 7. The mRNAs were transfected into Hepa1-6 cells, a mouse hepatoma cell line derived from the BW7756 tumor that arose in a C57BL/6 mouse, using MESSENGER MAX transfection reagents. The cell culture medium was collected at 24, 48, and 72 hrs after transfection. hEPO protein production was detected using ELISA at 24, 48, and 72 hrs. The hEPO expressions for each time point were normalized using hEPO having 5'UTR of TEV and 3'UTR of XbG as a control. FIG. 1 shows the normalized expressions at 24 hrs, as compared to normalized expressions at 48 hrs. Using translatable molecules of this invention, expression for human erythropoietin (hEPO) was surprisingly increased over control by more than 100%.

Figure 2:
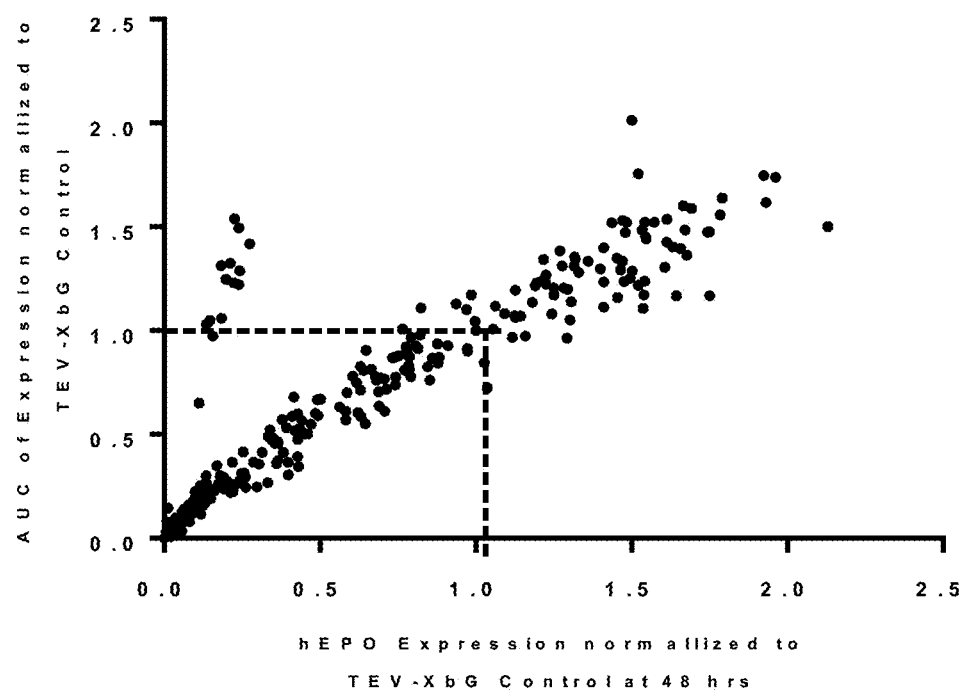
FIG. 2 shows the results of enhanced expression control for human erythropoietin (hEPO) in vitro using translatable molecules of this invention. hEPO mRNAs were synthesized in vitro using T7RNA polymerase-mediated DNA-dependent RNA transcription, where UTP was substituted with 100% $N^1$-methylpseudouracil (N1MPU), using a linearized template for each UTR combination. mRNAs were synthesized having all combinations of different 5'UTR and 3'UTR of Table 7. The mRNAs were transfected into Hepa1-6 cells, a mouse hepatoma cell line derived from the BW7756 tumor that arose in a C57L mouse, using MESSENGER MAX transfection reagents. The cell culture medium was collected at 24, 48, and 72 hrs after transfection. hEPO protein production was detected using ELISA at 24, 48, and 72 hrs. The hEPO expressions for each time point were normalized using hEPO having 5'UTR of TEV and 3'UTR of XbG as a control.

FIG. 2 shows the results of enhanced expression control for human erythropoietin (hEPO) in vitro using translatable molecules of this invention. hEPO mRNAs were synthesized in vitro using T7RNA polymerase-mediated DNA-dependent RNA transcription, where UTP was substituted with 100% N$^1$-methylpseudouracil (N1MPU), using a linearized template for each UTR combination. mRNAs were synthesized having all combinations of different 5'UTR and 3'UTR of Table 7. The mRNAs were transfected into Hepa1-6 cells, a mouse hepatoma cell line derived from the BW7756 tumor that arose in a C57BL/6 mouse, using MESSENGER MAX transfection reagents. The cell culture medium was collected at 24, 48, and 72 hrs after transfection. hEPO protein production was detected using ELISA at 24, 48, and 72 hrs. The hEPO expressions for each time point were normalized using hEPO having 5'UTR of TEV and 3'UTR of XbG as a control. FIG. 2 shows the area under the curve (AUC) for normalized expression, as compared to normalized expression at 48 hrs. Using translatable molecules of this invention, expression for human erythropoietin (hEPO) was surprisingly increased over control by more than 100%.

Figure 3:
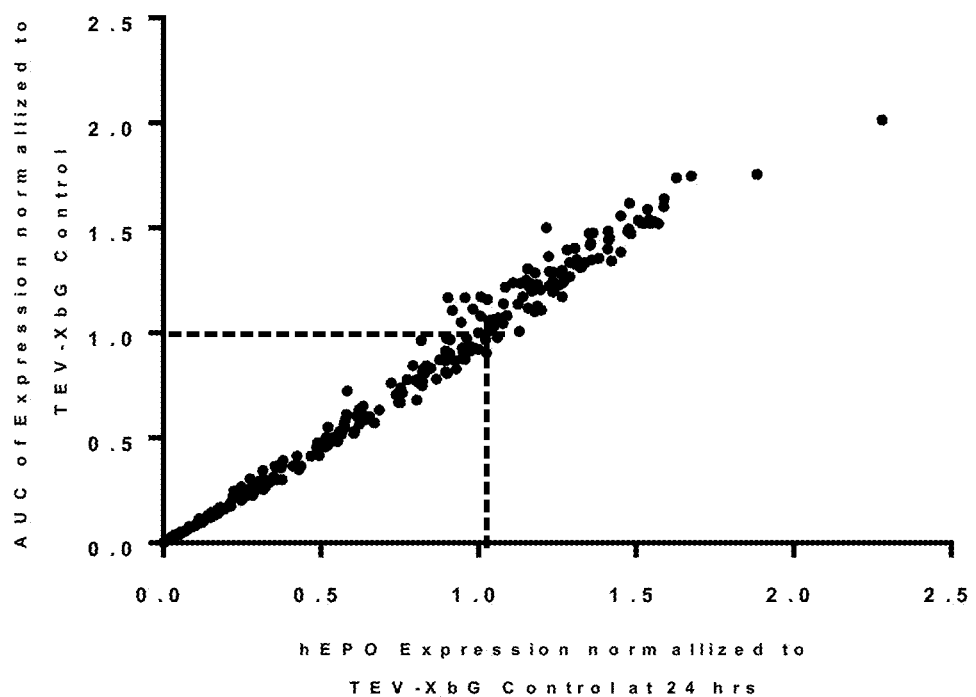
FIG. 3 shows the results of enhanced expression control for human erythropoietin (hEPO) in vitro using translatable molecules of this invention. hEPO mRNAs were synthesized in vitro using T7RNA polymerase-mediated DNA-dependent RNA transcription, where UTP was substituted with 100% $N^1$-methylpseudouracil (N1MPU), using a linearized template for each UTR combination. mRNAs were synthesized having all combinations of different 5'UTR and 3'UTR of Table 7. The mRNAs were transfected into Hepa1-6 cells, a mouse hepatoma cell line derived from the BW7756 tumor that arose in a C57L mouse, using MESSENGER MAX transfection reagents. The cell culture medium was collected at 24, 48, and 72 hrs after transfection. hEPO protein production was detected using ELISA at 24, 48, and 72 hrs. The hEPO expressions for each time point were normalized using hEPO having 5'UTR of TEV and 3'UTR of XbG as a control.

FIG. 3 shows the results of enhanced expression control for human erythropoietin (hEPO) in vitro using translatable molecules of this invention. hEPO mRNAs were synthesized in vitro using T7RNA polymerase-mediated DNA-dependent RNA transcription, where UTP was substituted with 100% N$^1$-methylpseudouracil (N1MPU), using a linearized template for each UTR combination. mRNAs were synthesized having all combinations of different 5'UTR and 3'UTR of Table 7. The mRNAs were transfected into Hepa1-6 cells, a mouse hepatoma cell line derived from the BW7756 tumor that arose in a C57BL/6 mouse, using MESSENGER MAX transfection reagents. The cell culture medium was collected at 24, 48, and 72 hrs after transfection. hEPO protein production was detected using ELISA at 24, 48, and 72 hrs. The hEPO expressions for each time point were normalized using hEPO having 5'UTR of TEV and 3'UTR of XbG as a control. FIG. 3 shows the area under the curve (AUC) for normalized expression, as compared to normalized expression at 24 hrs. Using translatable molecules of this invention, expression for human erythropoietin (hEPO) was surprisingly increased over control by more than 100%.

Example 3

5'UTR-3'UTR Combination Sequences for Constructs

Examples of mRNA construct structures made having various 5'UTR-3'UTR combination sequences are shown in Table 7. An mRNA construct may comprise a 5' cap (for example, m7GpppGm), a 5' UTR, a Kozak sequence, a target CDS, a 3'UTR, and a tail region. In some embodiments, an mRNA construct may comprise a cap, one or more 5' UTRs, a Kozak sequence, a target CDS, and one or more 3'UTRs.

TABLE 7

Examples of 5'UTR-3'UTR combination sequences for constructs

| mRNA | 5' UTR | 3' UTR |
|---|---|---|
| 101 | TEV | Mouse beta globin |
| 102 | TEV | Human beta globin |
| 103 | TEV | *Xenopus* beta globin |
| 104 | TEV | Human growth factor |
| 105 | TEV | Mouse Albumin |
| 106 | TEV | Human alpha globin |
| 107 | TEV | Human haptoglobin |
| 108 | TEV | Human antithrombin |
| 109 | TEV | Human complement C3 |
| 110 | TEV | Human hepcidin |
| 111 | TEV | Human fibrinogen alpha chain |
| 112 | TEV | Human apolipoprotein E |
| 113 | TEV | Alanine aminotransferase 1 |
| 114 | TEV | MALAT |
| 115 | TEV | 3xMALAT |
| 116 | TEV | ARC3-2 |
| 117 | AT1G58420 | Mouse beta globin |
| 118 | AT1G58420 | Human beta globin |
| 119 | AT1G58420 | *Xenopus* beta globin |
| 120 | AT1G58420 | Human growth factor |
| 121 | AT1G58420 | Mouse Albumin |
| 122 | AT1G58420 | Human alpha globin |
| 123 | AT1G58420 | Human haptoglobin |
| 124 | AT1G58420 | Human antithrombin |
| 125 | AT1G58420 | Human complement C3 |
| 126 | AT1G58420 | Human hepcidin |

TABLE 7-continued

Examples of 5'UTR-3'UTR combination sequences for constructs

| mRNA | 5' UTR | 3' UTR |
|---|---|---|
| 127 | AT1G58420 | Human fibrinogen alpha chain |
| 128 | AT1G58420 | Human apolipoprotein E |
| 129 | AT1G58420 | Alanine aminotransferase 1 |
| 130 | AT1G58420 | MALAT |
| 131 | AT1G58420 | 3xMALAT |
| 132 | AT1G58420 | ARC3-2 |
| 133 | SynK | Mouse beta globin |
| 134 | SynK | Human beta globin |
| 135 | SynK | *Xenopus* beta globin |
| 136 | SynK | Human growth factor |
| 137 | SynK | Mouse Albumin |
| 138 | SynK | Human alpha globin |
| 139 | SynK | Human haptoglobin |
| 140 | SynK | Human antithrombin |
| 141 | SynK | Human complement C3 |
| 142 | SynK | Human hepcidin |
| 143 | SynK | Human fibrinogen alpha chain |
| 144 | SynK | Human apolipoprotein E |
| 145 | SynK | Alanine aminotransferase 1 |
| 146 | SynK | MALAT |
| 147 | SynK | 3xMALAT |
| 148 | SynK | ARC3-2 |
| 149 | Truncated Rossi | Mouse beta globin |
| 150 | Truncated Rossi | Human beta globin |
| 151 | Truncated Rossi | *Xenopus* beta globin |
| 152 | Truncated Rossi | Human growth factor |
| 153 | Truncated Rossi | Mouse Albumin |
| 154 | Truncated Rossi | Human alpha globin |
| 155 | Truncated Rossi | Human haptoglobin |
| 156 | Truncated Rossi | Human antithrombin |
| 157 | Truncated Rossi | Human complement C3 |
| 158 | Truncated Rossi | Human hepcidin |
| 159 | Truncated Rossi | Human fibrinogen alpha chain |
| 160 | Truncated Rossi | Human apolipoprotein E |
| 161 | Truncated Rossi | Alanine aminotransferase 1 |
| 162 | Truncated Rossi | MALAT |
| 163 | Truncated Rossi | 3xMALAT |
| 164 | Truncated Rossi | ARC3-2 |
| 165 | Human Albumin | Mouse beta globin |
| 166 | Human Albumin | Human beta globin |
| 167 | Human Albumin | *Xenopus* beta globin |
| 168 | Human Albumin | Human growth factor |
| 169 | Human Albumin | Mouse Albumin |
| 170 | Human Albumin | Human alpha globin |
| 171 | Human Albumin | Human haptoglobin |
| 172 | Human Albumin | Human antithrombin |
| 173 | Human Albumin | Human complement C3 |
| 174 | Human Albumin | Human hepcidin |
| 175 | Human Albumin | Human fibrinogen alpha chain |
| 176 | Human Albumin | Human apolipoprotein E |
| 177 | Human Albumin | Alanine aminotransferase 1 |
| 178 | Human Albumin | MALAT |
| 179 | Human Albumin | 3xMALAT |
| 180 | Human Albumin | ARC3-2 |
| 181 | Mouse beta globin | Mouse beta globin |
| 182 | Mouse beta globin | Human beta globin |
| 183 | Mouse beta globin | *Xenopus* beta globin |
| 184 | Mouse beta globin | Human growth factor |
| 185 | Mouse beta globin | Mouse Albumin |
| 186 | Mouse beta globin | Human alpha globin |
| 187 | Mouse beta globin | Human haptoglobin |
| 188 | Mouse beta globin | Human antithrombin |
| 189 | Mouse beta globin | Human complement C3 |
| 190 | Mouse beta globin | Human hepcidin |
| 191 | Mouse beta globin | Human fibrinogen alpha chain |
| 192 | Mouse beta globin | Human apolipoprotein E |
| 193 | Mouse beta globin | Alanine aminotransferase 1 |
| 194 | Mouse beta globin | MALAT |
| 195 | Mouse beta globin | 3xMALAT |
| 196 | Mouse beta globin | ARC3-2 |
| 197 | Human beta globin | Mouse beta globin |
| 198 | Human beta globin | Human beta globin |
| 199 | Human beta globin | *Xenopus* beta globin |
| 200 | Human beta globin | Human growth factor |
| 201 | Human beta globin | Mouse Albumin |
| 202 | Human beta globin | Human alpha globin |
| 203 | Human beta globin | Human haptoglobin |
| 204 | Human beta globin | Human antithrombin |
| 205 | Human beta globin | Human complement C3 |
| 206 | Human beta globin | Human hepcidin |
| 207 | Human beta globin | Human fibrinogen alpha chain |
| 208 | Human beta globin | Human apolipoprotein E |
| 209 | Human beta globin | Alanine aminotransferase 1 |
| 210 | Human beta globin | MALAT |
| 211 | Human beta globin | 3xMALAT |
| 212 | Human beta globin | ARC3-2 |
| 213 | Mouse Albumin | Mouse beta globin |
| 214 | Mouse Albumin | Human beta globin |
| 215 | Mouse Albumin | *Xenopus* beta globin |
| 216 | Mouse Albumin | Human growth factor |
| 217 | Mouse Albumin | Mouse Albumin |
| 218 | Mouse Albumin | Human alpha globin |
| 219 | Mouse Albumin | Human haptoglobin |
| 220 | Mouse Albumin | Human antithrombin |
| 221 | Mouse Albumin | Human complement C3 |
| 222 | Mouse Albumin | Human hepcidin |
| 223 | Mouse Albumin | Human fibrinogen alpha chain |
| 224 | Mouse Albumin | Human apolipoprotein E |
| 225 | Mouse Albumin | Alanine aminotransferase 1 |
| 226 | Mouse Albumin | MALAT |
| 227 | Mouse Albumin | 3xMALAT |
| 228 | Mouse Albumin | ARC3-2 |
| 229 | Human alpha globin | Mouse beta globin |
| 230 | Human alpha globin | Human beta globin |
| 231 | Human alpha globin | *Xenopus* beta globin |
| 232 | Human alpha globin | Human growth factor |
| 233 | Human alpha globin | Mouse Albumin |
| 234 | Human alpha globin | Human alpha globin |
| 235 | Human alpha globin | Human haptoglobin |
| 236 | Human alpha globin | Human antithrombin |
| 237 | Human alpha globin | Human complement C3 |
| 238 | Human alpha globin | Human hepcidin |
| 239 | Human alpha globin | Human fibrinogen alpha chain |
| 240 | Human alpha globin | Human apolipoprotein E |
| 241 | Human alpha globin | Alanine aminotransferase 1 |
| 242 | Human alpha globin | MALAT |
| 243 | Human alpha globin | 3xMALAT |
| 244 | Human alpha globin | ARC3-2 |
| 245 | Human haptoglobin | Mouse beta globin |
| 246 | Human haptoglobin | Human beta globin |
| 247 | Human haptoglobin | *Xenopus* beta globin |
| 284 | Human antithrombin | Human antithrombin |
| 285 | Human antithrombin | Human complement C3 |
| 286 | Human antithrombin | Human hepcidin |
| 287 | Human antithrombin | Human fibrinogen alpha chain |
| 288 | Human antithrombin | Human apolipoprotein E |
| 289 | Human antithrombin | Alanine aminotransferase 1 |
| 290 | Human antithrombin | MALAT |
| 291 | Human antithrombin | 3xMALAT |
| 292 | Human antithrombin | ARC3-2 |
| 293 | Human C3 | Mouse beta globin |
| 294 | Human C3 | Human beta globin |
| 295 | Human C3 | *Xenopus* beta globin |
| 296 | Human C3 | Human growth factor |
| 297 | Human C3 | Mouse Albumin |
| 298 | Human C3 | Human alpha globin |
| 299 | Human C3 | Human haptoglobin |
| 300 | Human C3 | Human antithrombin |
| 301 | Human C3 | Human complement C3 |
| 302 | Human C3 | Human hepcidin |
| 303 | Human C3 | Human fibrinogen alpha chain |
| 304 | Human C3 | Human apolipoprotein E |
| 305 | Human C3 | Alanine aminotransferase 1 |
| 306 | Human C3 | MALAT |
| 307 | Human C3 | 3xMALAT |
| 308 | Human C3 | ARC3-2 |
| 309 | Human C5 | Mouse beta globin |
| 310 | Human C5 | Human beta globin |
| 311 | Human C5 | *Xenopus* beta globin |
| 312 | Human C5 | Human growth factor |
| 313 | Human C5 | Mouse Albumin |
| 314 | Human C5 | Human alpha globin |

TABLE 7-continued

Examples of 5'UTR-3'UTR combination sequences for constructs

| mRNA | 5' UTR | 3' UTR |
| --- | --- | --- |
| 315 | Human C5 | Human haptoglobin |
| 316 | Human C5 | Human antithrombin |
| 317 | Human C5 | Human complement C3 |
| 318 | Human C5 | Human hepcidin |
| 319 | Human C5 | Human fibrinogen alpha chain |
| 320 | Human C5 | Human apolipoprotein E |
| 321 | Human C5 | Alanine aminotransferase 1 |
| 322 | Human C5 | MALAT |
| 323 | Human C5 | 3xMALAT |
| 324 | Human C5 | ARC3-2 |
| 325 | Human AAT | Mouse beta globin |
| 326 | Human AAT | Human beta globin |
| 327 | Human AAT | *Xenopus* beta globin |
| 328 | Human AAT | Human growth factor |
| 329 | Human AAT | Mouse Albumin |
| 330 | Human AAT | Human alpha globin |
| 331 | Human AAT | Human haptoglobin |
| 332 | Human AAT | Human antithrombin |
| 333 | Human AAT | Human complement C3 |
| 334 | Human AAT | Human hepcidin |
| 335 | Human AAT | Human fibrinogen alpha chain |
| 336 | Human AAT | Human apolipoprotein E |
| 337 | Human AAT | Alanine aminotransferase 1 |
| 338 | Human AAT | MALAT |
| 339 | Human AAT | 3xMALAT |
| 340 | Human AAT | ARC3-2 |
| 341 | Human alpha-1-antichymotrypsin | Mouse beta globin |
| 342 | Human alpha-1-antichymotrypsin | Human beta globin |
| 343 | Human alpha-1-antichymotrypsin | *Xenopus* beta globin |
| 344 | Human alpha-1-antichymotrypsin | Human growth factor |
| 345 | Human alpha-1-antichymotrypsin | Mouse Albumin |
| 346 | Human alpha-1-antichymotrypsin | Human alpha globin |
| 347 | Human alpha-1-antichymotrypsin | Human haptoglobin |
| 348 | Human alpha-1-antichymotrypsin | Human antithrombin |
| 349 | Human alpha-1-antichymotrypsin | Human complement C3 |
| 350 | Human alpha-1-antichymotrypsin | Human hepcidin |
| 351 | Human alpha-1-antichymotrypsin | Human fibrinogen alpha chain |
| 352 | Human alpha-1-antichymotrypsin | Human apolipoprotein E |
| 353 | Human alpha-1-antichymotrypsin | Alanine aminotransferase 1 |
| 354 | Human alpha-1-antichymotrypsin | MALAT |
| 355 | Human alpha-1-antichymotrypsin | 3xMALAT |
| 356 | Human alpha-1-antichymotrypsin | ARC3-2 |
| 357 | Human Interleukin 6 | Mouse beta globin |
| 358 | Human Interleukin 6 | Human beta globin |
| 359 | Human Interleukin 6 | *Xenopus* beta globin |
| 360 | Human Interleukin 6 | Human growth factor |
| 361 | Human Interleukin 6 | Mouse Albumin |
| 362 | Human Interleukin 6 | Human alpha globin |
| 363 | Human Interleukin 6 | Human haptoglobin |
| 364 | Human Interleukin 6 | Human antithrombin |
| 365 | Human Interleukin 6 | Human complement C3 |
| 366 | Human Interleukin 6 | Human hepcidin |
| 367 | Human Interleukin 6 | Human fibrinogen alpha chain |
| 368 | Human Interleukin 6 | Human apolipoprotein E |
| 369 | Human Interleukin 6 | Alanine aminotransferase 1 |
| 370 | Human Interleukin 6 | MALAT |
| 371 | Human Interleukin 6 | 3xMALAT |
| 372 | Human Interleukin 6 | ARC3-2 |
| 373 | Human fibrinogen alpha chain | Mouse beta globin |
| 374 | Human fibrinogen alpha chain | Human beta globin |
| 375 | Human fibrinogen alpha chain | *Xenopus* beta globin |
| 376 | Human fibrinogen alpha chain | Human growth factor |
| 377 | Human fibrinogen alpha chain | Mouse Albumin |
| 378 | Human fibrinogen alpha chain | Human alpha globin |
| 379 | Human fibrinogen alpha chain | Human haptoglobin |
| 380 | Human fibrinogen alpha chain | Human antithrombin |
| 381 | Human fibrinogen alpha chain | Human complement C3 |
| 382 | Human fibrinogen alpha chain | Human hepcidin |
| 383 | Human fibrinogen alpha chain | Human fibrinogen alpha chain |
| 384 | Human fibrinogen alpha chain | Human apolipoprotein E |
| 385 | Human fibrinogen alpha chain | Alanine aminotransferase 1 |
| 386 | Human fibrinogen alpha chain | MALAT |
| 387 | Human fibrinogen alpha chain | 3xMALAT |
| 388 | Human fibrinogen alpha chain | ARC3-2 |
| 389 | Human ApoE | Mouse beta globin |
| 390 | Human ApoE | Human beta globin |
| 391 | Human ApoE | *Xenopus* beta globin |
| 392 | Human ApoE | Human growth factor |
| 393 | Human ApoE | Mouse Albumin |
| 394 | Human ApoE | Human alpha globin |
| 395 | Human ApoE | Human haptoglobin |
| 396 | Human ApoE | Human antithrombin |
| 397 | Human ApoE | Human complement C3 |
| 398 | Human ApoE | Human hepcidin |
| 399 | Human ApoE | Human fibrinogen alpha chain |
| 400 | Human ApoE | Human apolipoprotein E |
| 401 | Human ApoE | Alanine aminotransferase 1 |
| 402 | Human ApoE | MALAT |
| 403 | Human ApoE | 3xMALAT |
| 404 | Human ApoE | ARC3-2 |
| 405 | Human Ala Aminotransferase | Mouse beta globin |
| 406 | Human Ala Aminotransferase | Human beta globin |
| 407 | Human Ala Aminotransferase | *Xenopus* beta globin |
| 408 | Human Ala Aminotransferase | Human growth factor |
| 409 | Human Ala Aminotransferase | Mouse Albumin |
| 410 | Human Ala Aminotransferase | Human alpha globin |
| 411 | Human Ala Aminotransferase | Human haptoglobin |
| 412 | Human Ala Aminotransferase | Human antithrombin |
| 413 | Human Ala Aminotransferase | Human complement C3 |
| 414 | Human Ala Aminotransferase | Human hepcidin |
| 415 | Human Ala Aminotransferase | Human fibrinogen alpha chain |
| 416 | Human Ala Aminotransferase | Human apolipoprotein E |
| 417 | Human Ala Aminotransferase | Alanine aminotransferase 1 |
| 418 | Human Ala Aminotransferase | MALAT |
| 419 | Human Ala Aminotransferase | 3xMALAT |
| 420 | Human Ala Aminotransferase | ARC3-2 |
| 421 | HHV | Mouse beta globin |
| 422 | HHV | Human beta globin |
| 423 | HHV | *Xenopus* beta globin |
| 424 | HHV | Human growth factor |
| 425 | HHV | Mouse Albumin |
| 426 | HHV | Human alpha globin |
| 427 | HHV | Human haptoglobin |
| 428 | HHV | Human antithrombin |
| 429 | HHV | Human complement C3 |
| 430 | HHV | Human hepcidin |
| 431 | HHV | Human fibrinogen alpha chain |
| 432 | HHV | Human apolipoprotein E |
| 433 | HHV | Alanine aminotransferase 1 |
| 434 | HHV | MALAT |
| 435 | HHV | 3xMALAT |
| 436 | HHV | ARC3-2 |

Example 4

Translatable Molecule for hEPO

In this example, a translatable molecule can be made and used for expressing human EPO with advantageously increased efficiency of translation.

hEPO mRNA
SEQ ID NO: 122
AUGGGGGUGCACGAAUGUCCUGCCUGGCUGUGGCUUCUCCUGUCCCUGCU

GUCGCUCCCUCUGGGGCUCCCAGUCCUGGGCGCCCCACCACGCCUCAUCU

GUGACAGCCGAGUCCUGGAGAGGUACCUCUUGGAGGCCAAGGAGGCCGAG

AAUAUCACGACGGGCUGUGCUGAACACUGCAGCUUGAAUGAGAAUAUCAC

UGUCCCAGACACCAAAGUUAAUUUCUAUGCCUGGAAGAGGAUGGAGGUCG

GGCAGCAGGCCGUAGAAGUCUGGCAGGGCCUGGCCCUGCUGUCGGAAGCU

GUCCUGCGGGGCCAGGCCCUGUUGGUCAACUCUUCCCAGCCGUGGGAGCC

CCUGCAGCUGCAUGUGGAUAAAGCCGUCAGUGGCCUUCGCAGCCUCACCA

CUCUGCUUCGGGCUCUGGGAGCCCAGAAGGAAGCCAUCUCCCCUCCAGAU

GCGGCCUCAGCUGCUCCACUCCGAACAAUCACUGCUGACACUUUCCGCAA

ACUCUUCCGAGUCUACUCCAAUUUCCUCCGGGGAAAGCUGAAGCUGUACA

CAGGGGAGGCCUGCAGGACAGGGGACAGAUGA

Example 5

Translatable Molecule for *Homo sapiens* Coagulation Factor IX (F9), Transcript Variant 1, mRNA NCBI Reference Sequence: NM_000133.3.

In this example, a translatable molecule can be made and used for expressing human coagulation factor IX (F9) in vivo. In this embodiment, the translatable molecule can comprise a 5' cap (m7GpppGm), a 5' UTR, a Kozak sequence, a F9 CDS, a 3'UTR, and a Poly(A) tail region.

The translatable molecule may further comprise the sequence AUAAGUGAA (SEQ ID NO:123) immediately downstream of the F9 CDS.

The translatable molecule of this embodiment can be translated to produce human F9.

Details of the mRNA coding sequence of this translatable molecule are as follows:

F9 CDS
(SEQ ID NO: 124)
AUGCAGCGCGUGAACAUGAUCAUGGCAGAAUCACCAGGCCUCAUCACCAU

CUGCCUUUUAGGAUAUCUACUCAGUGCUGAAUGUACAGUUUUUCUUGAUC

AUGAAAACGCCAACAAAAUUCUGAAUCGGCCAAAGAGGUAUAAUUCAGGU

AAAUUGGAAGAGUUUGUUCAAGGGAACCUUGAGAGAGAAUGUAUGGAAGA

AAAGUGUAGUUUUGAAGAAGCACGAGAAGUUUUUGAAAACACUGAAAGAA

CAACUGAAUUUUGGAAGCAGUAUGUUGAUGGAGAUCAGUGUGAGUCCAAU

CCAUGUUUAAAUGGCGGCAGUUGCAAGGAUGACAUUAAUUCCUAUGAAUG

UUGGUGUCCCUUUGGAUUUGAAGGAAAGAACUGUGAAUUAGAUGUAACAU

GUAACAUUAAGAAUGGCAGAUGCGAGCAGUUUUGUAAAAAUAGUGCUGAU

AACAAGGUGGUUUGCUCCUGUACUGAGGGAUAUCGACUUGCAGAAAACCA

GAAGUCCUGUGAACCAGCAGUGCCAUUUCCAUGUGGAAGAGUUUCUGUUU

CACAAACUUCUAAGCUCACCCGUGCUGAGACUGUUUUUCCUGAUGUGGAC

UAUGUAAAUUCUACUGAAGCUGAAACCAUUUUGGAUAACAUCACUCAAAG

CACCCAAUCAUUUAAUGACUUCACUCGGGUUGUUGGUGGAGAAGAUGCCA

AACCAGGUCAAUUCCCUUGGCAGGUUGUUUUGAAUGGUAAAGUUGAUGCA

UUCUGUGGAGGCUCUAUCGUUAAUGAAAAAUGGAUUGUAACUGCUGCCCA

CUGUGUUGAAACUGGUGUUAAAAUUACAGUUGUCGCAGGUGAACAUAAUA

UUGAGGAGACAGAACAUACAGAGCAAAAGCGAAAUGUGAUUCGAAUUAUU

CCUCACCACAACUACAAUGCAGCUAUUAAUAAGUACAACCAUGACAUUGC

CCUUCUGGAACUGGACGAACCCUUAGUGCUAAACAGCUACGUUACACCUA

UUUGCAUUGCUGACAAGGAAUACACGAACAUCUUCCUCAAAUUUGGAUCU

GGCUAUGUAAGUGGCUGGGGAAGAGUCUUCCACAAAGGGAGAUCAGCUUU

AGUUCUUCAGUACCUUAGAGUUCCACUUGUUGACCGAGCCACAUGUCUUC

GAUCUACAAAGUUCACCAUCUAUAACAACAUGUUCUGUGCUGGCUUCCAU

GAAGGAGGUAGAGAUUCAUGUCAAGGAGAUAGUGGGGGACCCCAUGUUAC

UGAAGUGGAAGGGACCAGUUUCUUAACUGGAAUUAUUAGCUGGGGUGAAG

AGUGUGCAAUGAAAGGCAAAUAUGGAAUAUAUACCAAGGUAUCCCGGUAU

GUCAACUGGAUUAAGGAAAAAACAAAGCUCACUUAA

Example 6

Expression of hEPO mRNA Constructs In Vitro

Figure 4:
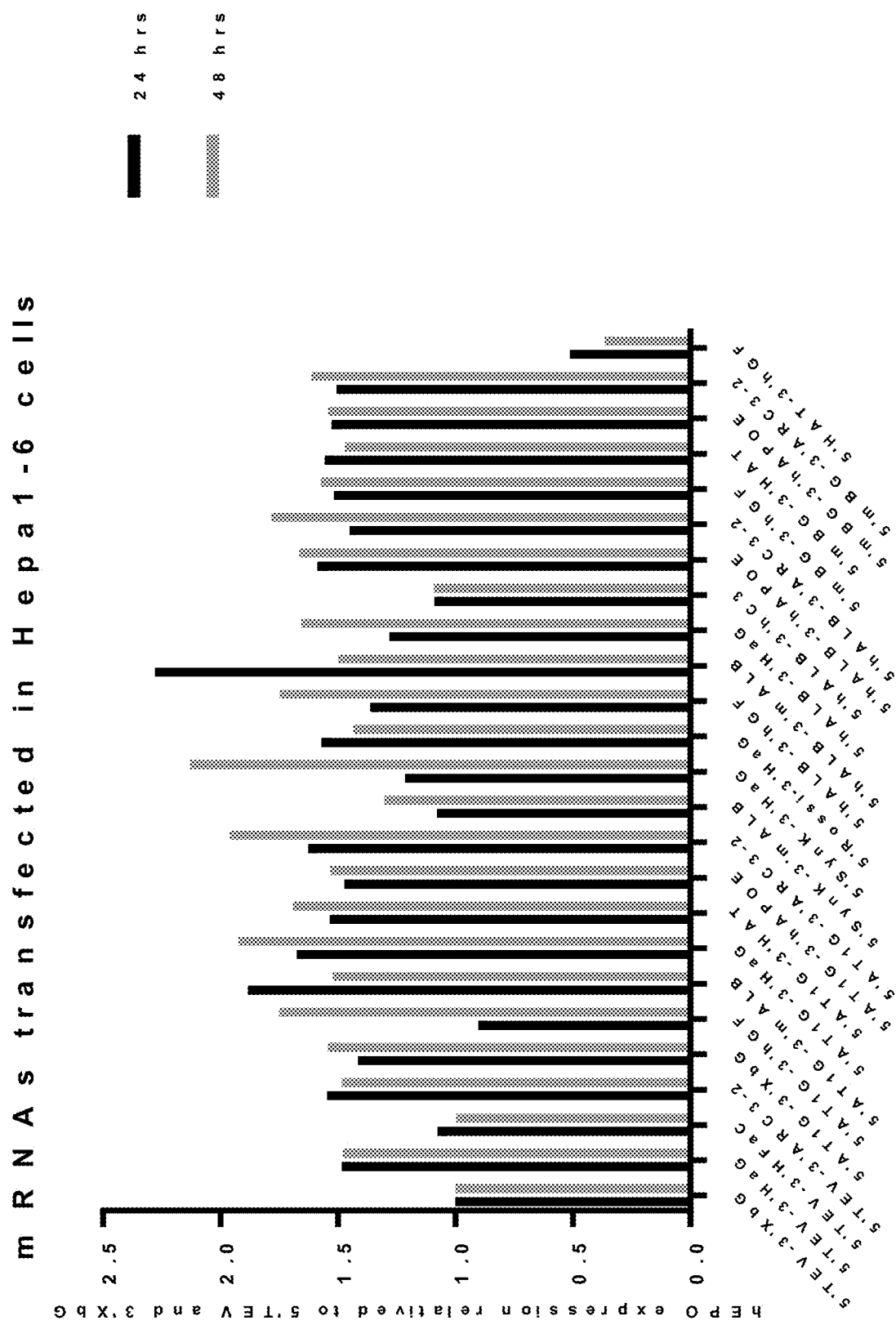
FIG. 4 shows the results of enhanced hEPO expression of mRNA constructs of this invention as compared the control mRNA construct 5'TEV-CDS-3'XbG in vitro in Hepa1-6 cells.

FIG. 4 shows the results of enhanced hEPO expression of mRNA constructs of this invention as compared the control mRNA construct 5' TEV-CDS-3'XbG in vitro in Hepa1-6 cells.

Example 7

Expression of hEPO mRNA Constructs In Vivo

Figure 5:
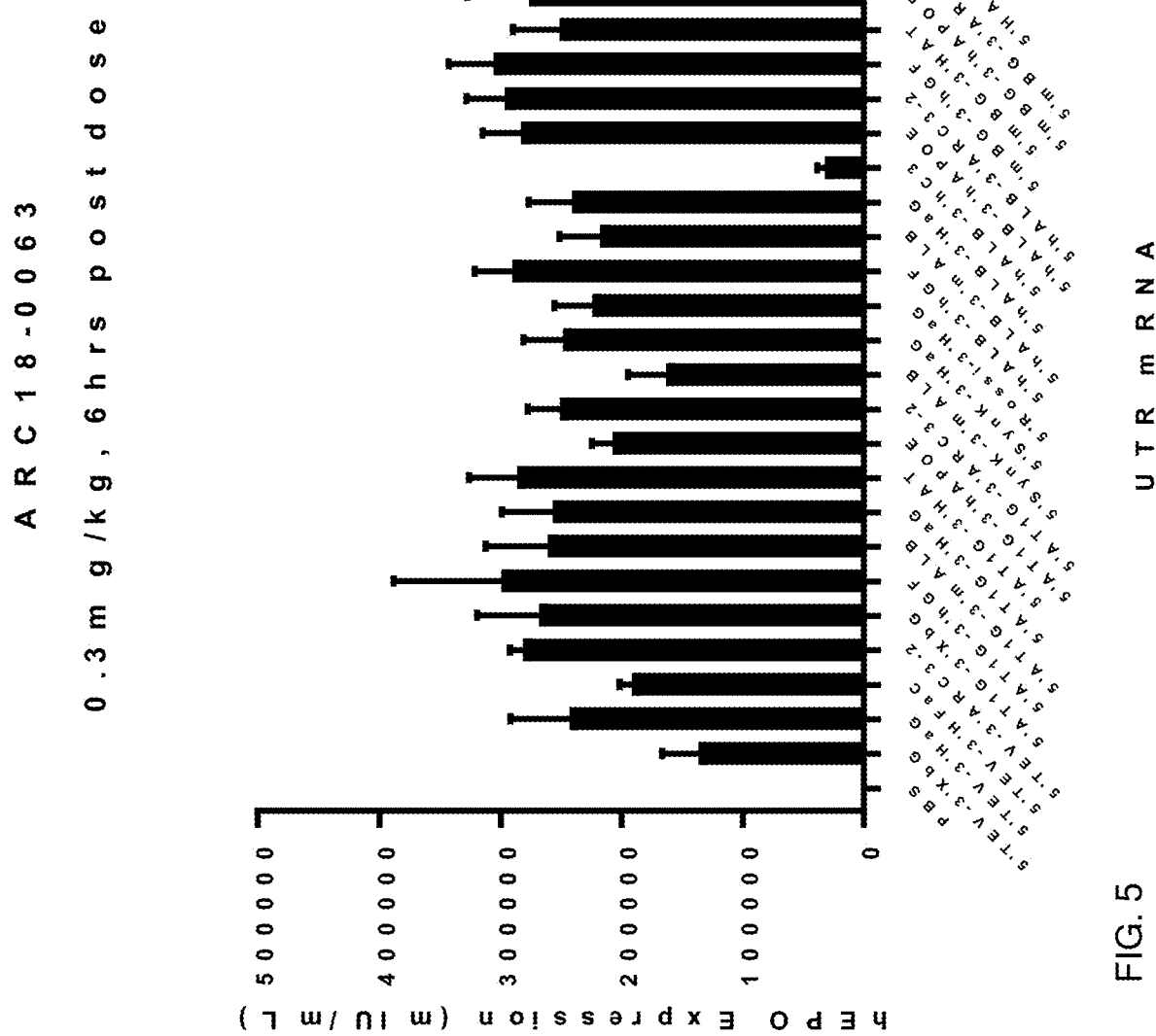
FIG. 5 shows the results of enhanced hEPO expression of mRNA constructs of this invention over the control mRNA construct 5'TEV-CDS-3'XbG in vivo at 6 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

FIG. 5 shows the results of enhanced hEPO expression of mRNA constructs of this invention over the control mRNA construct 5'TEV-CDS-3'XbG in vivo at 6 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

Example 8

Expression of hEPO mRNA Constructs In Vivo

Figure 6:
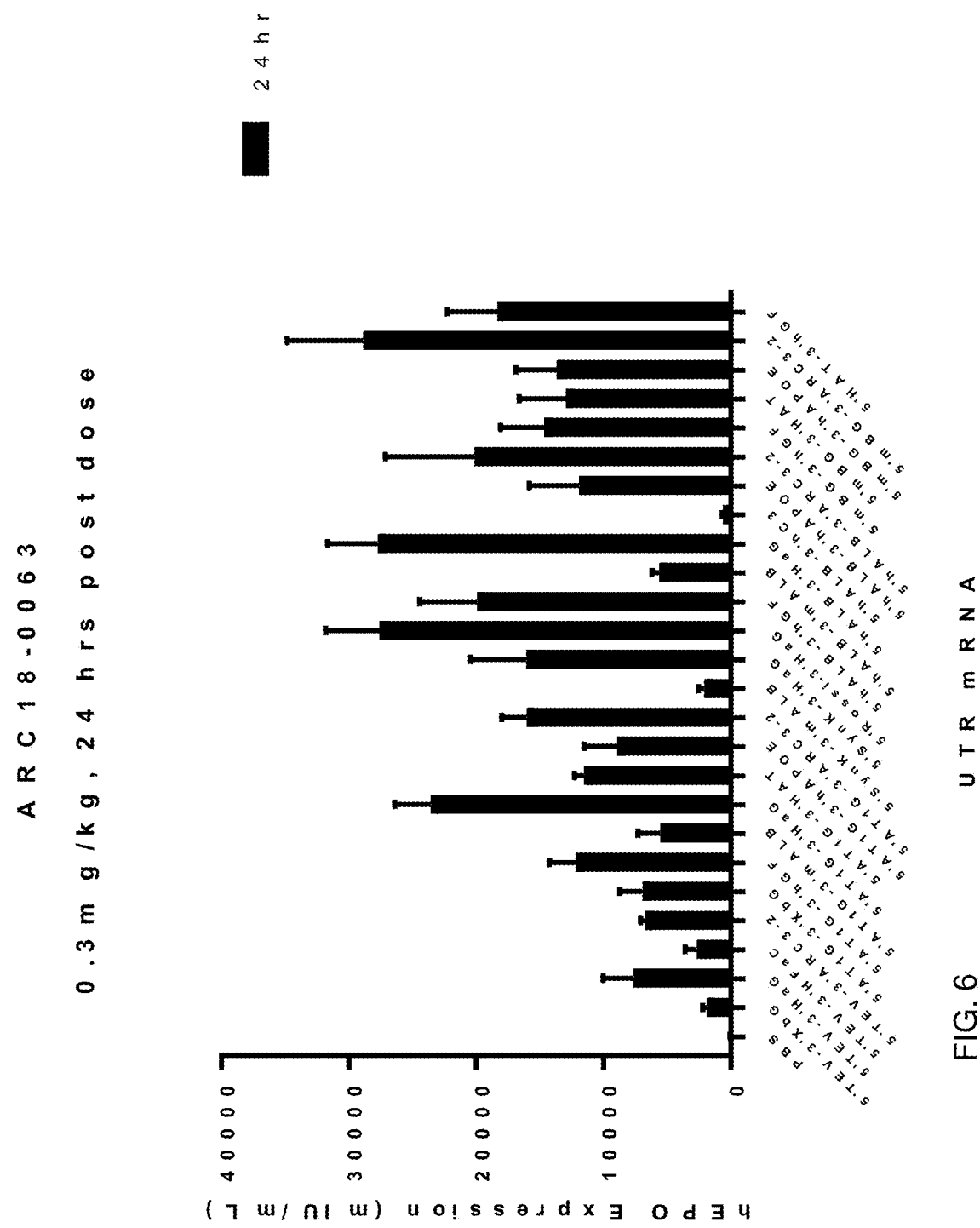
FIG. 6 shows the results of enhanced hEPO expression of mRNA constructs of this invention over the control mRNA construct 5'TEV-CDS-3'XbG in vivo at 24 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

FIG. 6 shows the results of enhanced hEPO expression of mRNA constructs of this invention over the control mRNA construct 5'TEV-CDS-3'XbG in vivo at 24 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

Example 9

Expression of hEPO mRNA Constructs In Vivo

Figure 7:
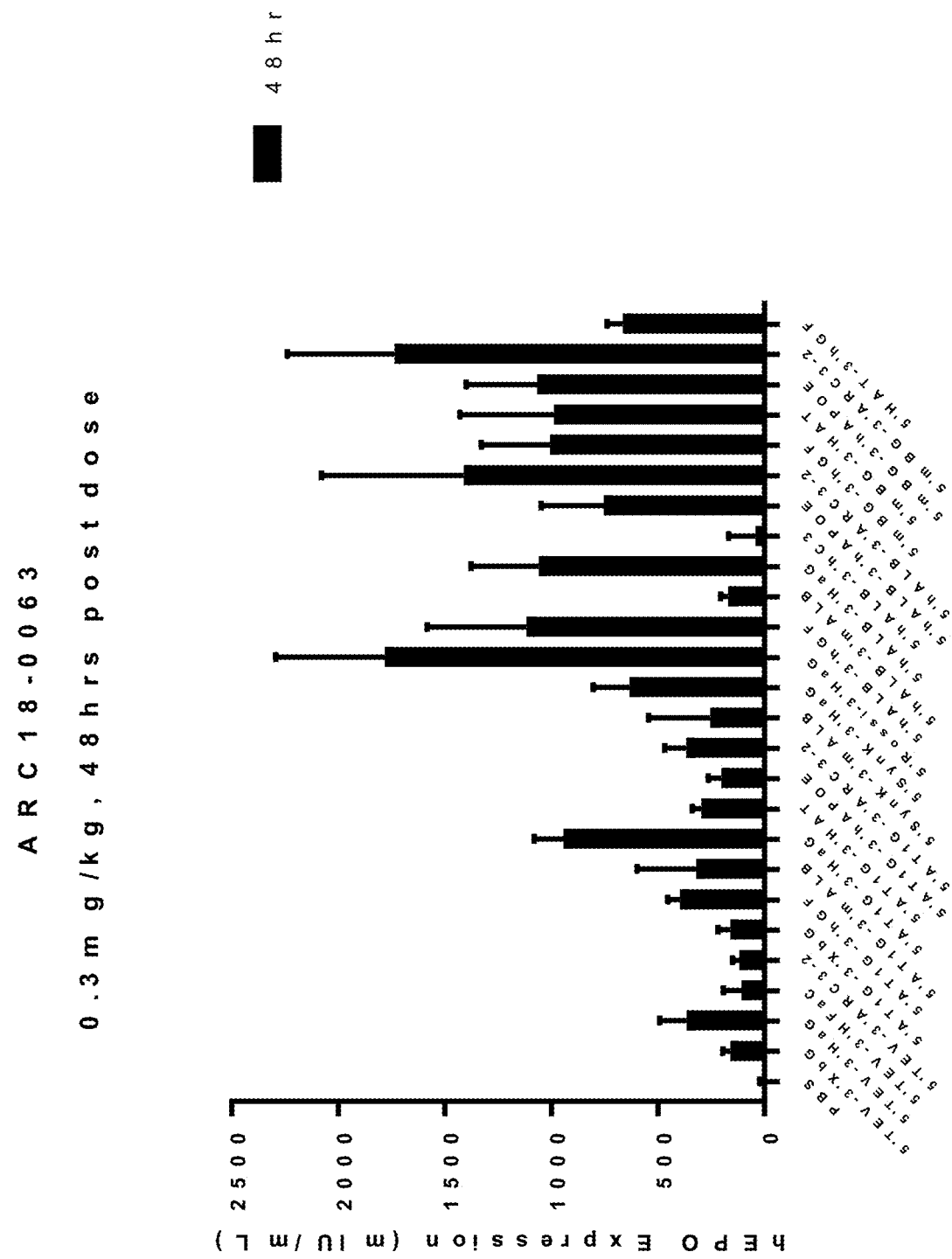
FIG. 7 shows the results of enhanced hEPO expression of mRNA constructs of this invention over the control mRNA construct 5' TEV-CDS-3'XbG in vivo at 48 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

FIG. 7 shows the results of enhanced hEPO expression of mRNA constructs of this invention over the control mRNA construct 5'TEV-CDS-3'XbG in vivo at 48 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

Example 10

Expression of hEPO mRNA Constructs In Vivo

Figure 8:
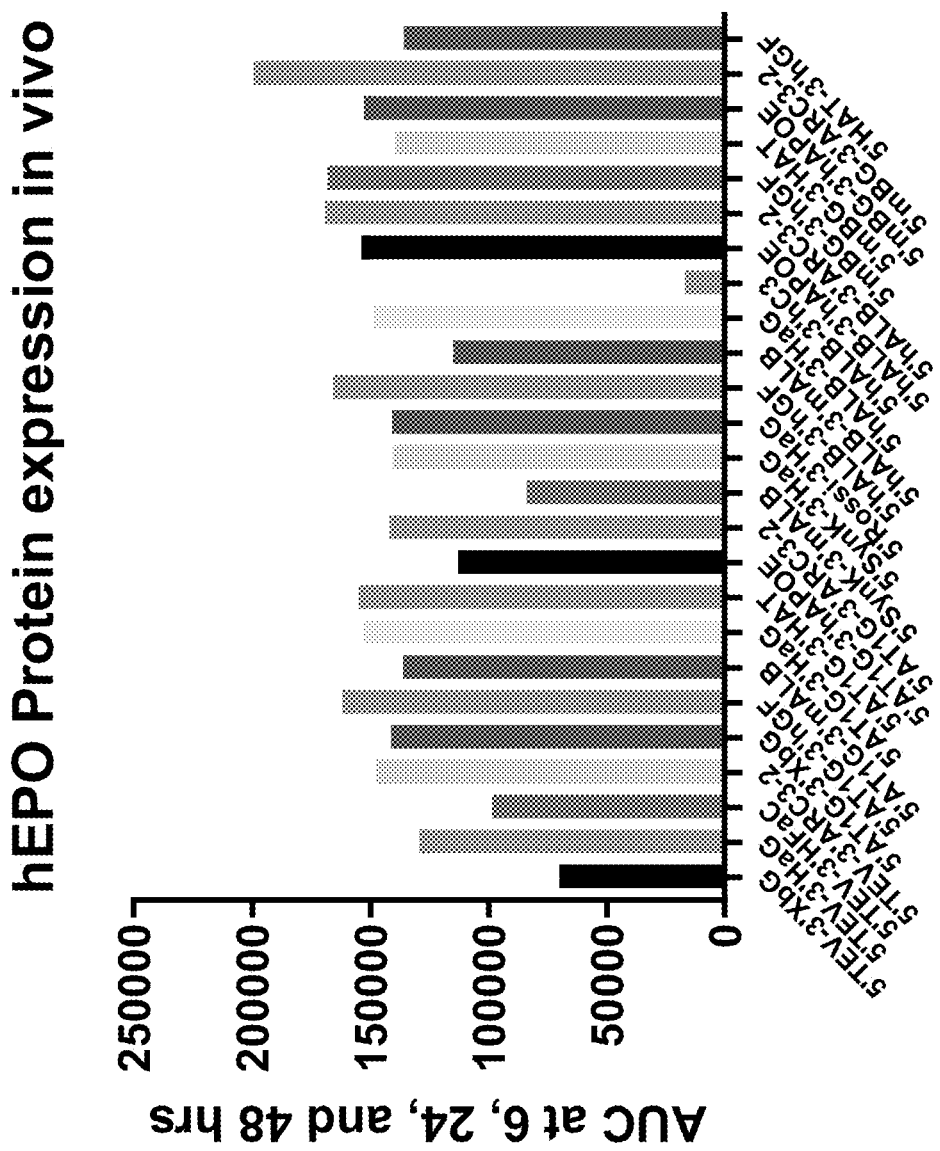
FIG. 8 shows the results of AUC analysis for enhanced hEPO expression of mRNA constructs of this invention over the control mRNA construct 5'TEV-CDS-3'XbG in vivo at 6, 24 and 48 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

FIG. 8 shows the results of AUC analysis for enhanced hEPO expression of mRNA constructs of this invention over the control mRNA construct 5'TEV-CDS-3'XbG in vivo at 6, 24 and 48 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

Example 11

Expression of hGDF15 mRNA Constructs In Vivo

Figure 9:
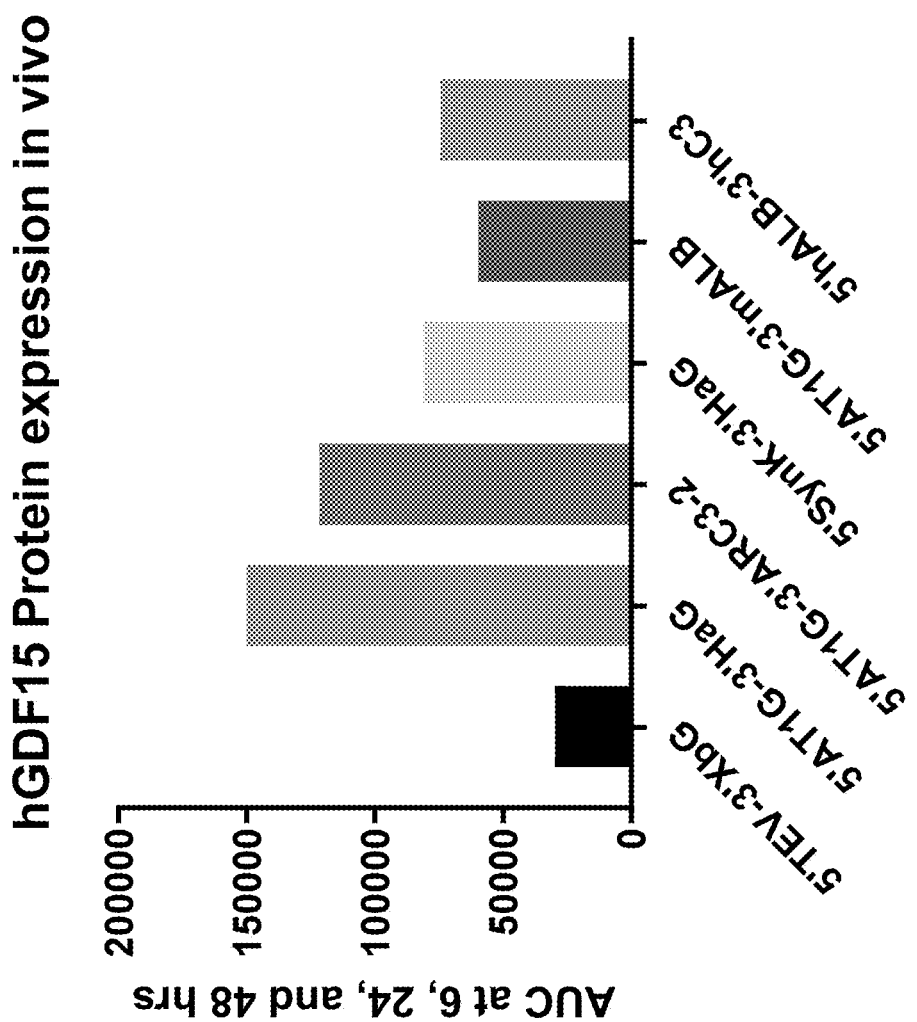
FIG. 9 shows the results of AUC analysis for enhanced hGDF15 expression of mRNA constructs of this invention over the control mRNA construct 5'TEV-CDS-3'XbG in vivo at 6, 24 and 48 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

FIG. 9 shows the results of AUC analysis for enhanced hGDF15 expression of mRNA constructs of this invention over the control mRNA construct 5'TEV-CDS-3'XbG in vivo at 6, 24 and 48 hours post IV-administration in male 6-8 week-old C57BL/6 mice at a dose of 0.3 mg/kg, 4 animals per group. Each construct was formulated as a lipid nanoparticle comprising the ATX-081 ionizable lipid.

Example 12

Expression of hGDF15 mRNA Constructs In Vivo

Figure 10:
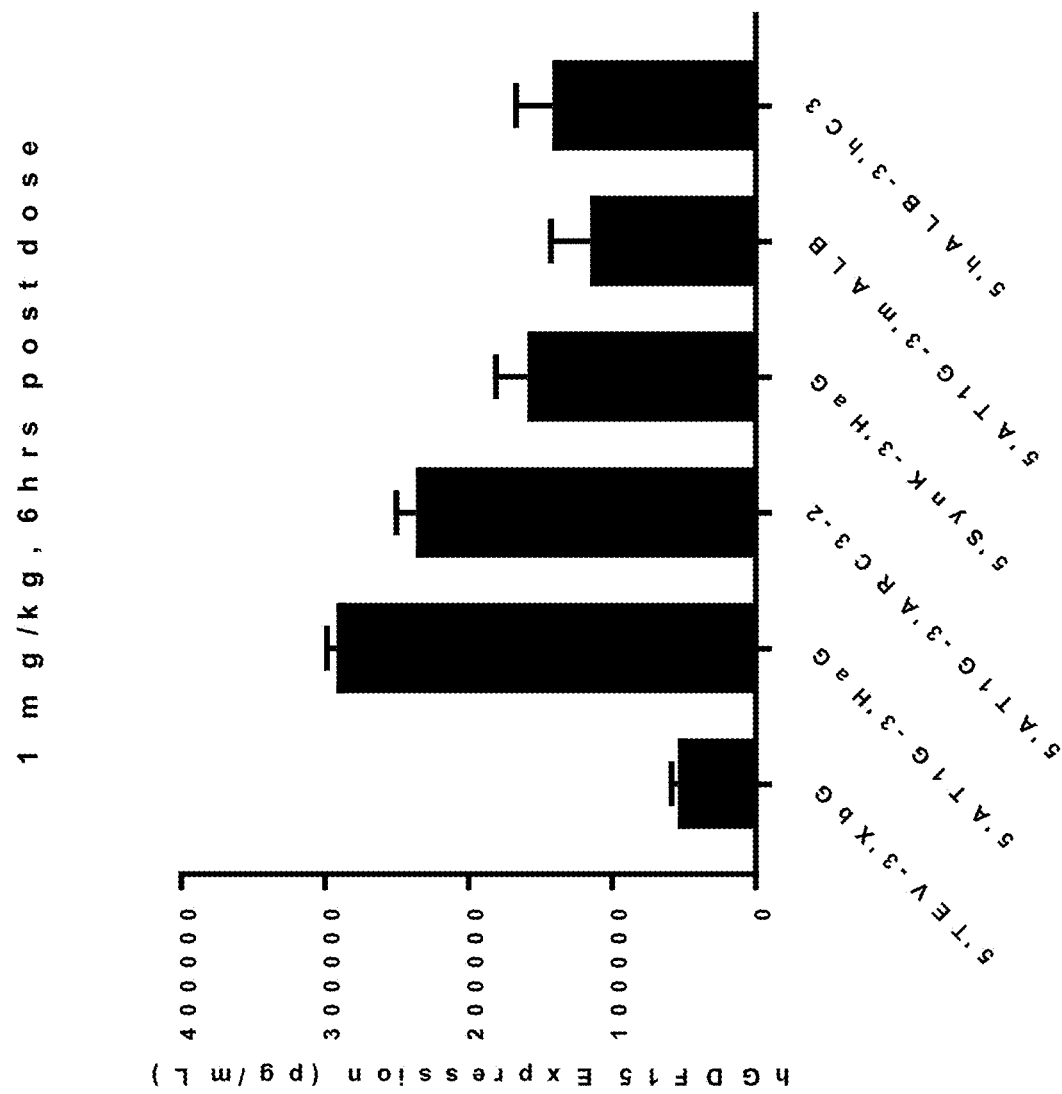
FIG. 10 shows the results of enhanced hGDF15 expression of mRNA constructs of this invention over the control mRNA construct 5'TEV-CDS-3'XbG in vivo at 6 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

FIG. 10 shows the results of enhanced hGDF15 expression of mRNA constructs of this invention over the control mRNA construct 5'TEV-CDS-3'XbG in vivo at 6 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

Example 13

Expression of hGDF15 mRNA Constructs In Vivo

Figure 11:
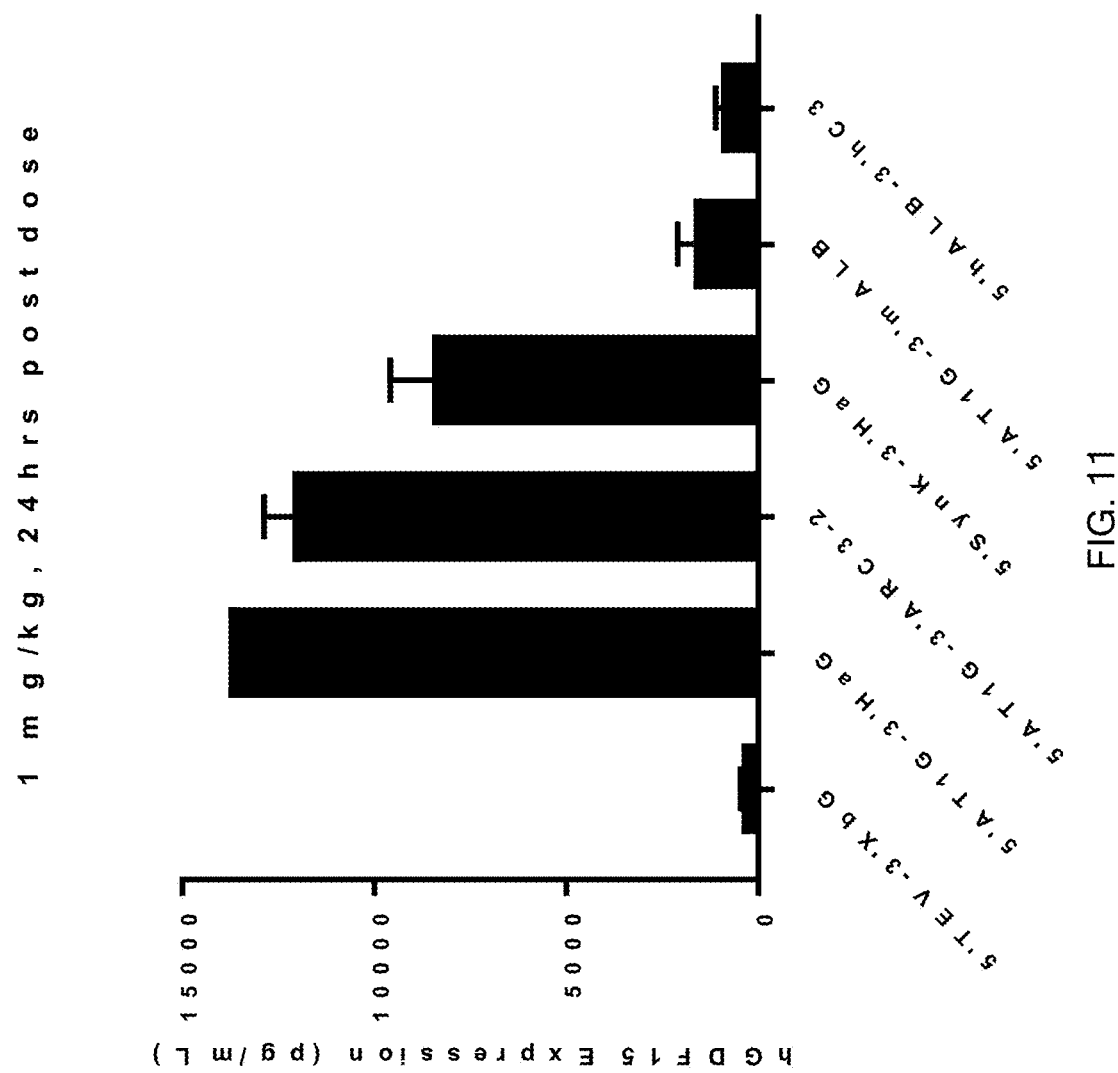
FIG. 11 shows the results of enhanced hGDF15 expression of mRNA constructs of this invention over the control mRNA construct 5'TEV-CDS-3'XbG in vivo at 24 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

FIG. 11 shows the results of enhanced hGDF15 expression of mRNA constructs of this invention over the control mRNA construct 5'TEV-CDS-3'XbG in vivo at 24 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

Example 14

Expression of hGDF15 mRNA Constructs In Vivo

Figure 12:
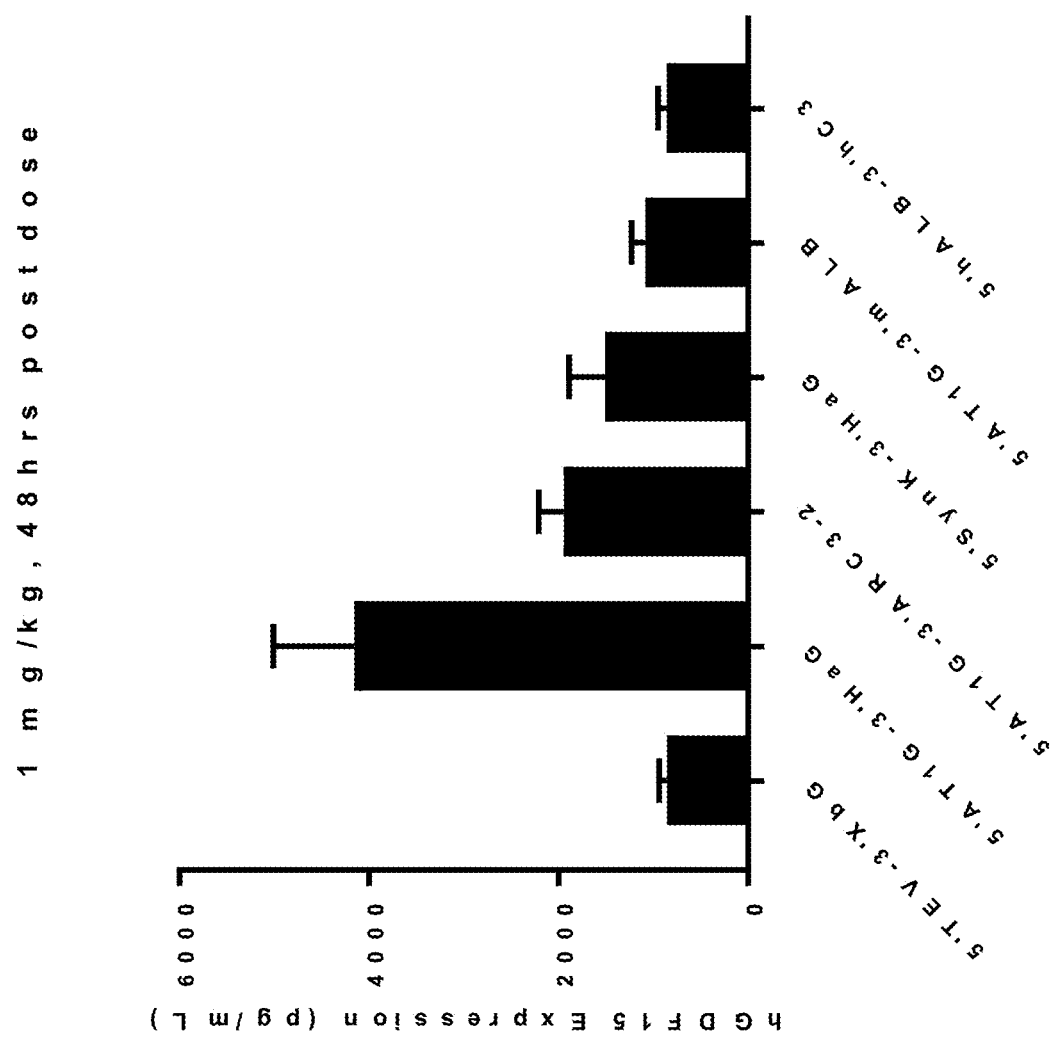
FIG. 12 shows the results of enhanced hGDF15 expression of mRNA constructs of this invention over the control mRNA construct 5'TEV-CDS-3'XbG in vivo at 48 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

FIG. 12 shows the results of enhanced hGDF15 expression of mRNA constructs of this invention over the control mRNA construct 5'TEV-CDS-3'XbG in vivo at 48 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

Example 15

Expression of hGDF15 mRNA Constructs In Vivo

Figure 13:
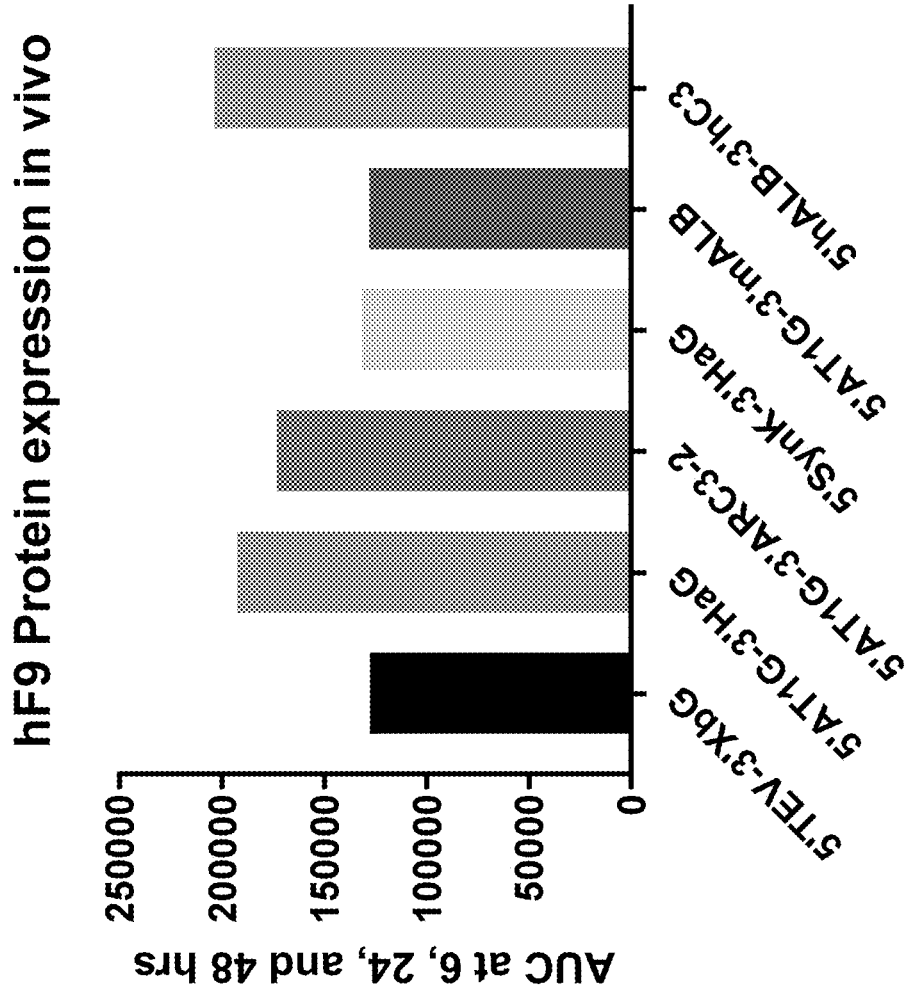
FIG. 13 shows the results of AUC analysis for enhanced hF9 expression of mRNA constructs of this invention over the control mRNA construct 5'TEV-CDS-3'XbG in vivo at 6, 24 and 48 hours post IV-administration in male 6-8 week-old C57BL/6 mice. Each construct was formulated as a lipid nanoparticle comprising the ATX-081 ionizable lipid.

FIG. 13 shows the results of AUC analysis for enhanced hF9 expression of mRNA constructs of this invention over the control mRNA construct 5'TEV-CDS-3'XbG in vivo at 6, 24 and 48 hours post IV-administration in male 6-8 week-old C57BL/6 mice. Each construct was formulated as a lipid nanoparticle comprising the ATX-081 ionizable lipid.

Example 16

Expression of hF9 mRNA Constructs In Vivo

Figure 14:
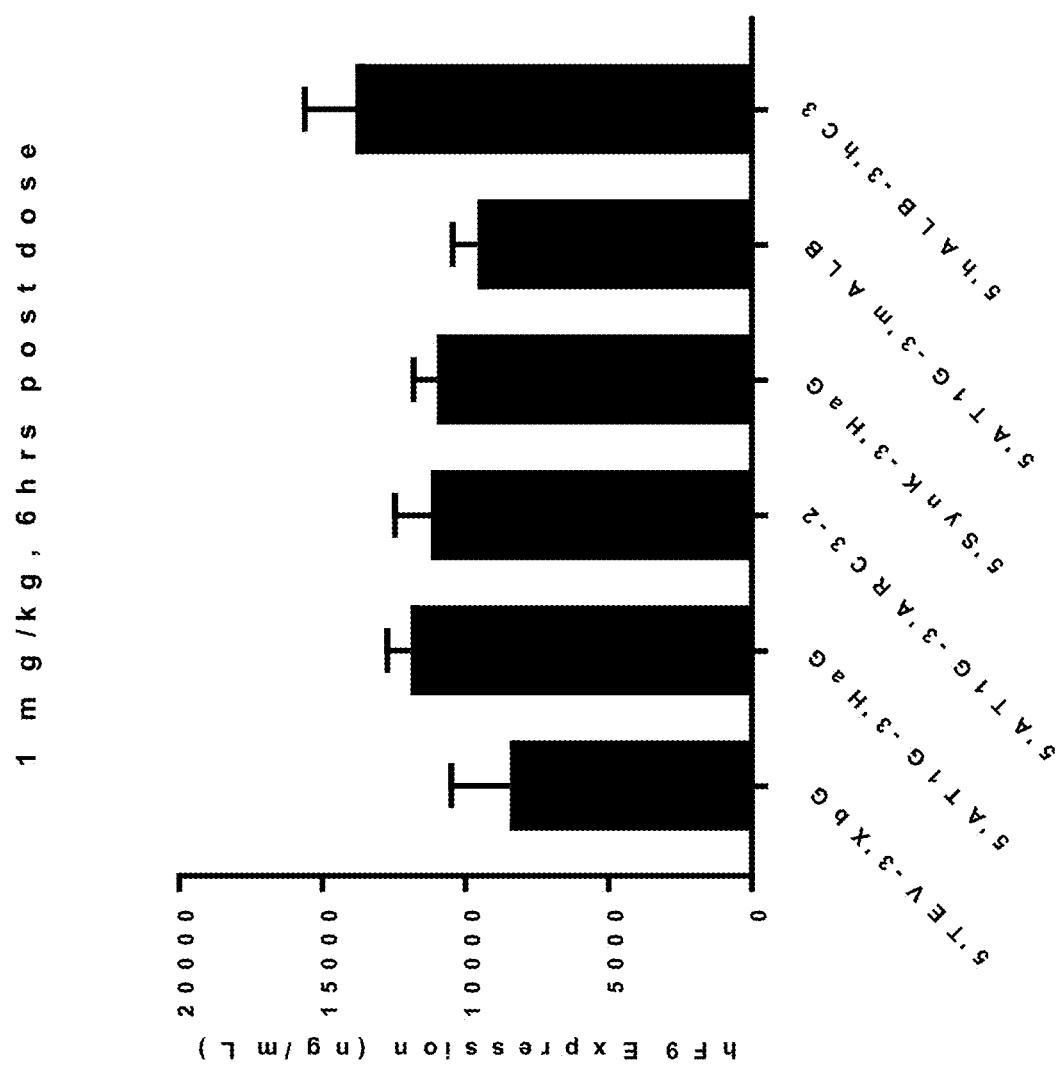
FIG. 14 shows the results of enhanced hF9 expression of mRNA constructs of this invention over the control mRNA construct 5'TEV-CDS-3'XbG in vivo at 6 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

FIG. 14 shows the results of enhanced hF9 expression of mRNA constructs of this invention over the control mRNA construct 5'TEV-CDS-3'XbG in vivo at 6 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

Example 17

Expression of hF9 mRNA Constructs In Vivo

Figure 15:
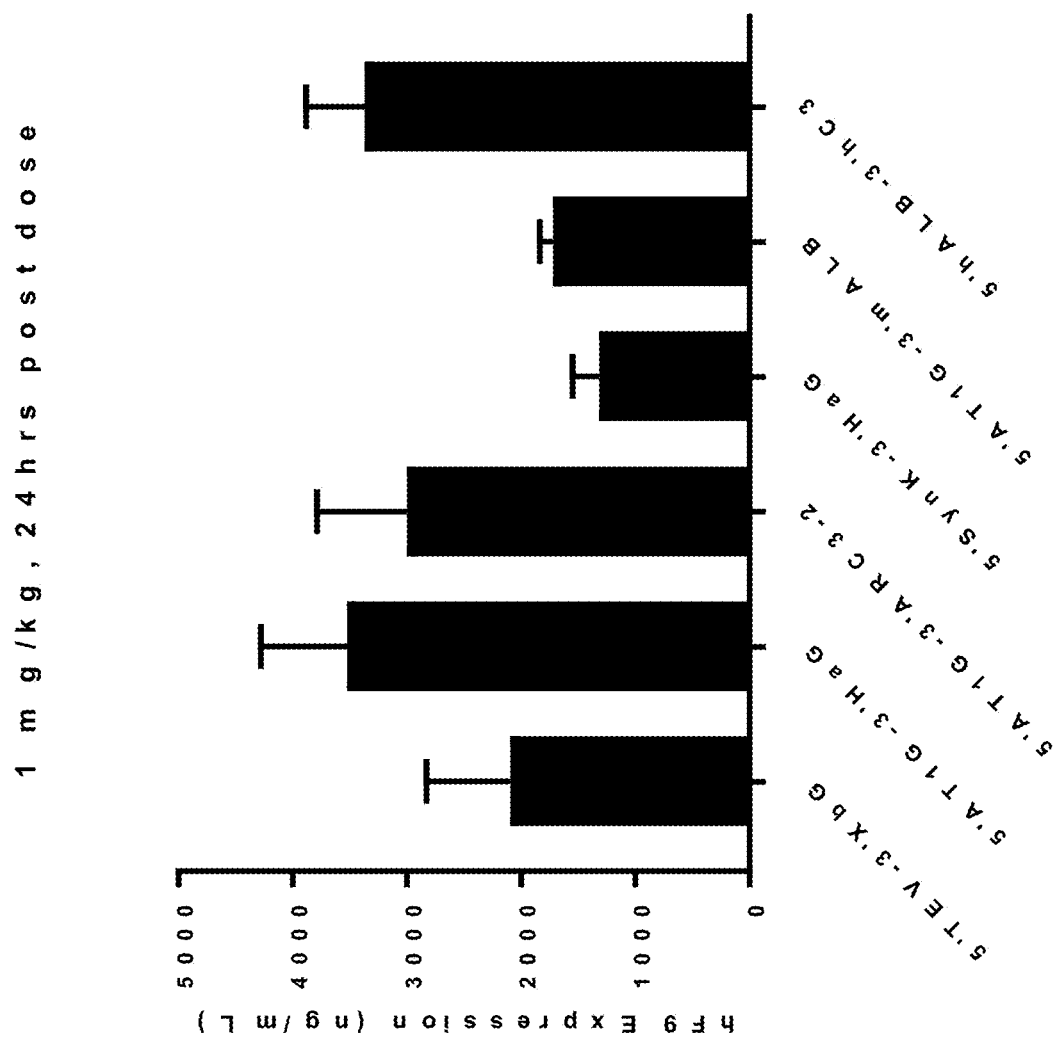
FIG. 15 shows the results of enhanced hF9 expression of mRNA constructs of this invention over the control mRNA construct 5'TEV-CDS-3'XbG in vivo at 24 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

FIG. 15 shows the results of enhanced hF9 expression of mRNA constructs of this invention over the control mRNA construct 5'TEV-CDS-3'XbG in vivo at 24 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

Example 18

Expression of hF9 mRNA Constructs In Vivo

Figure 16:
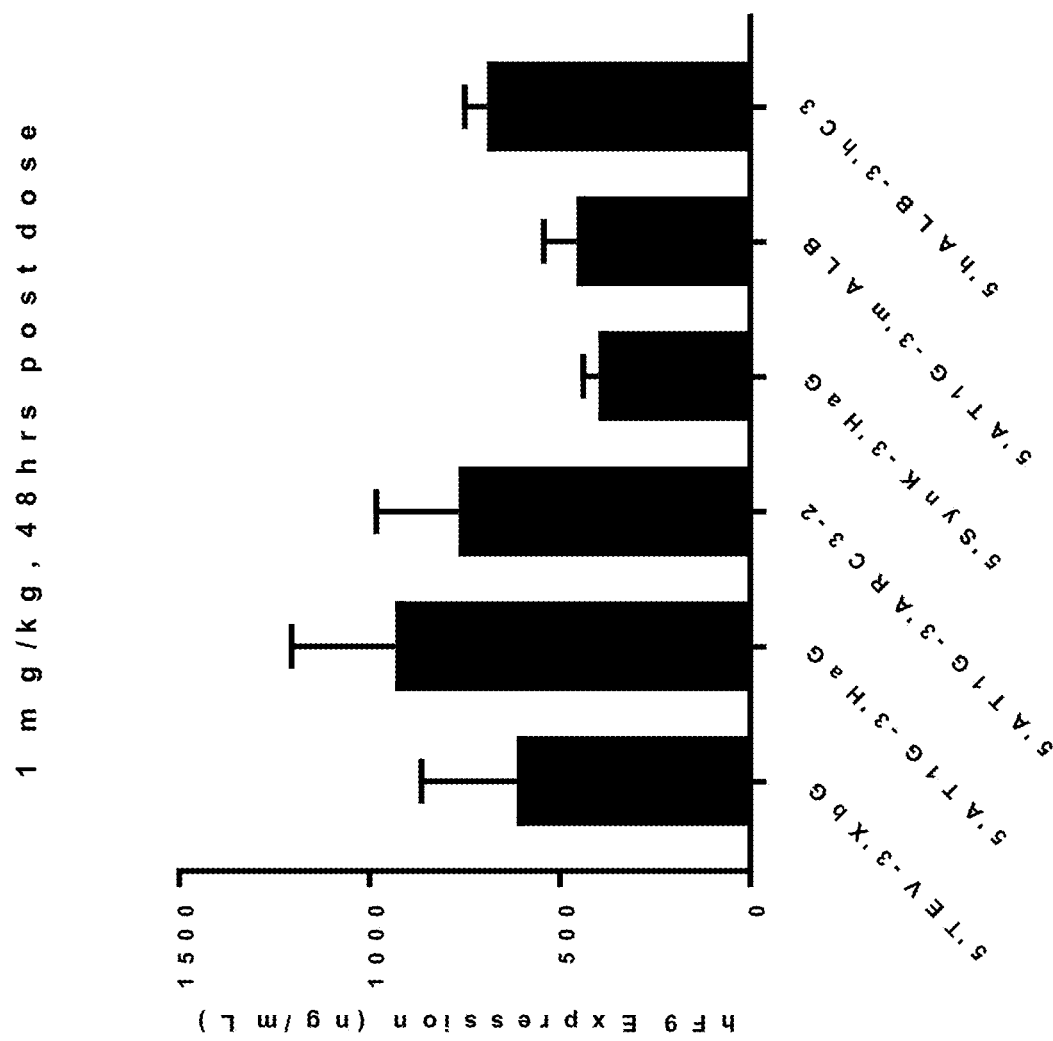
FIG. 16 shows the results of enhanced hF9 expression of mRNA constructs of this invention over the control mRNA construct 5'TEV-CDS-3'XbG in vivo at 48 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

FIG. 16 shows the results of enhanced hF9 expression of mRNA constructs of this invention over the control mRNA construct 5'TEV-CDS-3'XbG in vivo at 48 hours post IV-administration in male 6-8 week-old C57BL/6 mice at a dose of 1.0 mg/kg, 4 animals per group. Each construct was formulated as a lipid nanoparticle comprising the ATX-081 ionizable lipid.

Example 19

DNA Templates for EPO

```
Wt hEPO: 20.2% (118/582) * 100
Complementary strand.
                                (SEQ ID NO: 125)
Atgggggtgcacgaatgtcctgcctggctgtggcttctcctgtccctgct gtcgctccctctgggcctcccagtcctgggcgccccaccacgcctcatct gtgacagccgagtcctggagaggtacctcttggaggccaaggaggccgag aatatcacgacgggctgtgctgaacactgcagcttgaatgagaatatcac
```

```
tgtcccagacaccaaagttaatttctatgcctggaagaggatggaggtcg ggcagcaggccgtagaagtctggcagggcctggccctgctgtcggaagct gtcctgcggggccaggccctgttggtcaactcttcccagccgtgggagcc cctgcagctgcatgtggataaagccgtcagtggccttcgcagcctcacca ctctgcttcgggctctgggagcccagaaggaagccatctcccctccagat gcggcctcagctgctccactccgaacaatcactgctgacactttccgcaa actcttccgagtctactccaatttcctccggggaaagctgaagctgtaca caggggaggcctgcaggacaggggacagatga ARC-EPO 13% (76/582) * 100
Complementary strand.
                                          (SEQ ID NO: 126)
atgggcgtgcacgagtgccccgcctggctgtggctgctcctgagcctgct cagcctgccccctcggactgccgtgctcggagccccacccaggctgatct gcgacagcagggtgctggagaggtacctcctggaggccaaggaggccgag aacatcaccacaggctgcgccgagcactgcagcctgaacgagaacatcac cgtgcccgacaccaaggtgaacttctacgcctggaagaggatggaggtgg gccagcaggccgtggaggtgtggcagggcctggccctcctgagcgaggcc gtgctgagaggccaggccctgctcgtgaacagcagccagccctgggagcc actgcagctgcacgtggacaaggccgtgagcggcctgaggagcctgacca cactgctcagggccctgggcgcacagaaggaggccatcagcccacccgac gccgcaagcgccgcacccctgaggaccatcaccgccgacaccttcaggaa gctgttcagagtgtacagcaacttcctgagaggcaagctgaagctgtaca ccggcgaggcctgcaggaccggcgacagatga
```

Example 20

DNA Templates for Factor 9

```
Wt hF9: 27.6% (383/1386) * 100
Complementary strand.
                                          (SEQ ID NO: 127)
atgcagcgcgtgaacatgatcatggcagaatcaccaggcctcatcaccat ctgccttttaggatatctactcagtgctgaatgtacagttttttcttgatc atgaaaacgccaacaaaattctgaatcggccaagaggtataattcaggt aaattggaagagtttgttcaagggaaccttgagagagaatgtatggaaga aaagtgtagttttgaagaagcacgagaagtttttgaaaacactgaaagaa caactgaattttggaagcagtatgttgatggagatcagtgtgagtccaat ccatgtttaaatggcggcagttgcaaggatgacattaattcctatgaatg ttggtgtccctttggatttgaaggaaagaactgtgaattagatgtaacat gtaacattaagaatggcagatgcgagcagttttgtaaaaatagtgctgat aacaaggtggtttgctcctgtactgagggatatcgacttgcagaaaacca gaagtcctgtgaaccagcagtgccatttccatgtggaagagtttctgttt cacaaacttctaagctcacccgtgctgagactgtttttcctgatgtggac tatgtaaattctactgaagctgaaaccattttggataacatcactcaaag
```

```
cacccaatcatttaatgacttcactcgggttgttggtggagaagatgcca aaccaggtcaattcccttggcaggttgttttgaatggtaaagttgatgca ttctgtggaggctctatcgttaatgaaaaatggattgtaactgctgccca ctgtgttgaaactggtgttaaaattacagttgtcgcaggtgaacataata ttgaggagacagaacatacagagcaaaagcgaaatgtgattcgaattatt cctcaccacaactacaatgcagctattaataagtacaaccatgacattgc ccttctggaactggacgaaccttagtgctaaacagctacgttacaccta tttgcattgctgacaaggaatacacgaacatcttcctcaaatttggatct ggctatgtaagtggctggggaagagtcttccacaaagggagatcagcttt agttcttcagtacctagagttccacttgttgaccgagccacatgtcttc gatctacaaagttcaccatctataacaacatgttctgtgctggcttccat gaaggaggtagagattcatgtcaaggagatagtgggggacccccatgttac tgaagtggaagggaccagtttcttaactggaattattagctggggtgaag agtgtgcaatgaaaggcaaatatggaatatataccaaggtatcccggtat gtcaactggattaaggaaaaaacaaagctcacttaa ARC-F9: 17.9% (249/1386) * 100
Complementary strand.
                                          (SEQ ID NO: 128)
atgcagagagtgaacatgatcatggccgagagccctggcctgattaccat ctgcctgctgggctatctgctgtccgccgagtgtaccgtgttcctggacc acgagaacgccaataagatcctcaacaggcccaagaggtacaacagcgga aagctggaggagtttgtccagggcaacctggagagagagtgcatggagga gaagtgtagcttcgaagaggccagggaagtgttcgagaacaccgaaagga caaccgagttctgtgaagcagtacgtggacggagaccaatgcgaatccaac ccctgcctgaatggaggcagctgcaaggacgatatcaacagctacgagtg ctggtgccccttttggattcgaaggcaagaactgcgagctggacgtcacat gtaatattaaaaacggcagatgcgagcagttctgcaagaattccgccgat aacaaggtcgtgtgcagctgtaccgagggctacagactcgccgagaatca gaagagctgtgagcccgccgtccccttccctgtggaagggtgtccgtgt cccagacatccaagctgacaagggccgaaacagtgttccccgacgtggat tacgtgaacagcaccgaggctgaaaccatcctcgacaacatcacccagtc cacccagtccttcaatgacttcaccagggtcgtcggcggcgaagacgcca agccccgacaattcccctggcaggtcgtgctgaatggcaaggtcgatgcc ttttgcggaggctccatcgtgaacgagaagtggatcgtcaccgctgctca ctgtgtggagaccggcgtcaaaatcacagtggtcgctggcgagcacaaca ttgaggaaaccgagcacaccgagcagaagagaaacgtgatcaggattatt ccccaccacaactacaatgccgccatcaacaagtacaaccacgacatcgc tctgttagaactcgatgagcctctggtgctcaacagctatgtgacaccca tctgtatcgccgacaaggagtacaccaacatcttcctgaagttcggcagc ggatatgtcagcggatggggaaggtcttcacaaaggaaggtccgccct cgtgctgcaatacctgagagtgccctggtggacagggccacctgtctga ggtccacaaaattcaccatctacaacaacatgttctgcgccggcttccat
```

-continued
gagggcggcagagattcctgccaaggcgattccggaggcccccacgtgac agaggtcgagggcacctccttcctgaccggaatcattagctggggagagg agtgcgccatgaagggaaagtacggcatctacaccaaggtgtccaggtat gtcaactggatcaaggagaagacaaaactgacctaa

Example 21

Homo sapiens Ornithine Carbamoyltransferase (OTC)

mRNA is NCBI Reference Sequence: NM_000531.5.

In this example, a translatable molecule can be made and used for expressing human ornithine carbamoyltransferase (OTC) in vivo. In this embodiment, the translatable molecule may comprise a 5' cap (m7GpppGm), a 5' UTR, a Kozak sequence, a OTC CDS, a 3'UTR, and a Poly(A) tail region.

The translatable molecule may further comprise the sequence AUAAGUGAA (SEQ ID NO:129) immediately downstream of the OTC CDS. The molecule can be synthesized with $N^1$-methylpseudouridine in place of uridine.

The translatable molecule of this embodiment can be translated in C57BL/c mouse to produce human OTC.

Details of the mRNA coding sequence of this translatable molecule are as follows:

NM_000531.5 Homo sapiens ornithine
carbamoyltransferase (OTC), mRNA
CDS
(SEQ ID NO: 130)
AUGCUGUUUAAUCUGAGGAUCCUGUUAAACAAUGCAGCUUUUAGAAAUGG

UCACAACUUCAUGGUUCGAAAUUUUCGGUGUGGACAACCACUACAAAAUA

AAGUGCAGCUGAAGGGCCGUGACCUUCUCACUCUAAAAAACUUUACCGGA

GAAGAAAUUAAAUAUAUGCUAUGGCUAUCAGCAGAUCUGAAAUUUAGGAU

AAAACAGAAAGGAGAGUAUUUGCCUUUAUUGCAAGGGAAGUCCUUAGGCA

UGAUUUUUGAGAAAAGAAGUACUCGAACAAGAUUGUCUACAGAAACAGGC

UUUGCACUUCUGGGAGGACAUCCUUGUUUUCUUACCACACAAGAUAUUCA

UUUGGGUGUGAAUGAAAGUCUCACGGACACGGCCCGUGUAUUGUCUAGCA

UGGCAGAUGCAGUAUUGGCUCGAGUGUAUAAACAAUCAGAUUUGGACACC

CUGGCUAAAGAAGCAUCCAUCCCAAUUAUCAAUGGGCUGUCAGAUUUGUA

CCAUCCUAUCCAGAUCCUGGCUGAUUACCUCACGCUCCAGGAACACUAUA

GCUCUCUGAAAGGUCUUACCCUCAGCUGGAUCGGGGAUGGGAACAAUAUC

CUGCACUCCAUCAUGAUGAGCGCAGCGAAAUUCGGAAUGCACCUUCAGGC

AGCUACUCCAAAGGGUUAUGAGCCGGAUGCUAGUGUAACCAAGUUGGCAG

AGCAGUAUGCCAAAGAGAAUGGUACCAAGCUGUUGCUGACAAAUGAUCCA

UUGGAAGCAGCGCAUGGAGGCAAUGUAUUAAUUACAGACACUUGGAUAAG

CAUGGGACAAGAAGAGGAGAAGAAAAAGCGGCUCCAGGCUUUCCAAGGUU

ACCAGGUUACAAUGAAGACUGCUAAAGUUGCUGCCUCUGACUGGACAUUU

UUACACUGCUUGCCCAGAAAGCCAGAAGAAGUGGAUGAUGAAGUCUUUUA

UUCUCCUCGAUCACUAGUGUUCCCAGAGGCAGAAAACAGAAAGUGGACAA

UCAUGGCUGUCAUGGUGUCCCUGCUGACAGAUUACUCACCUCAGCUCCAG

AAGCCUAAAUUUUGA

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A synthetic mammalian mRNA expression construct for producing a protein or polypeptide, the synthetic mammalian mRNA expression construct comprising a 5' UTR, wherein the 5' UTR comprises a 5' UTR sequence of *Arabidopsis*, wherein the 5' UTR sequence is a sequence of AT1G58420.

2. The synthetic mammalian mRNA expression construct of claim 1, wherein the synthetic mammalian mRNA expression construct comprises a 3' UTR from an mRNA selected from ARC3-2, Human alpha globin, Human antithrombin, Human apolipoprotein E, Human growth factor, Mouse Albumin, and *Xenopus* beta globin.

3. The synthetic mammalian mRNA expression construct of claim 1, wherein the synthetic mammalian mRNA expression construct comprises a 3' UTR selected from a sequence of SEQ ID NO:78, SEQ ID NO:79, SEQ ID NO:80, SEQ ID NO:81, SEQ ID NO:83, SEQ ID NO:87, and SEQ ID NO:91.

4. The synthetic mammalian mRNA expression construct of claim 1, wherein the synthetic mammalian mRNA expression construct comprises a 5' cap, a coding sequence for encoding the protein or polypeptide, a 3' UTR, and a poly(A) or poly(C) tail.

5. The synthetic mammalian mRNA expression construct of claim 1, wherein the synthetic mammalian mRNA expression construct further comprises a Kozak sequence and a coding sequence encoding a protein deficient in a rare disease, wherein the rare disease is Aminoacylase 1 deficiency, Apo A-I deficiency, Carbamoyl phosphate synthetase 1 deficiency, Ornithine transcarbamylase deficiency, Plasminogen activator inhibitor type 1 deficiency, Flaujeac factor deficiency, High-molecular-weight kininogen deficiency congenital, PEPCK 1 deficiency, Pyruvate kinase deficiency liver type, Alpha 1-antitrypsin deficiency, Anti-plasmin deficiency congenital, Apolipoprotein C 2I deficiency, Butyrylcholinesterase deficiency, Complement component 2 deficiency, Complement component 8 deficiency type 2, Congenital antithrombin deficiency type 1, Congenital antithrombin deficiency type 2, Congenital antithrombin deficiency type 3, Cortisone reductase deficiency 1, Factor VII deficiency, Factor X deficiency, Factor XI deficiency, Factor XII deficiency, Factor XIII deficiency, Fibrinogen deficiency congenital, Fructose-1 6-bisphosphatase deficiency, Gamma aminobutyric acid transaminase deficiency, Gamma-cystathionase deficiency, Glut2 deficiency, GTP cyclohydrolase I deficiency, Isolated growth hormone deficiency type 1B, Molybdenum cofactor deficiency, Prekallikrein deficiency congenital, Proconvertin deficiency congenital, Protein S deficiency, Pseudocholinesterase deficiency, Stuart factor deficiency congenital, Tetrahydrobiopterin deficiency, Type 1 plasminogen deficiency, Urocanase deficiency, Chondrodysplasia *punctata* with steroid sulfatase deficiency, Homocystinuria due to CBS deficiency, Guanidinoacetate methyltransferase deficiency, Pulmonary surfactant protein B deficiency, Acid Sphingomyelinase Deficiency, Adenylosuccinate Lyase Deficiency, Aggressive Angiomyxoma, Albrights Hereditary Osteodystrophy, Carney Stratakis Syndrome, Carney Triad Syndrome, CDKL5 Mutation, CLOVES Syndrome, Cockayne Syndrome, Congenital Disorder of Glycosylation type 1R, Cowden Syndrome, DEND Syndrome, Dercum's Disease, Febrile Infection-Related Epilepsy Syndrome, Fibular Aplasia Tibial Campomelia Oligosyndactyly Syndrome, Food Protein-Induced Enterocolitis Syndrome, Foreign Body Giant Cell Reactive Tissue Disease, Galloway-Mowat, Gitelman syndrome, Glycerol Kinase Deficiency, Glycogen Storage Disease type 9, gm1 gangliosidosis, Hereditary spherocytosis, Hidradenitis Suppurativa Stage III, Horizonatal Gaze Palsy with Progressive Scoliosis, IMAGe syndrome, Isodicentric chromosome 15, isolated hemihyperplasia, Juvenile Xanthogranuloma, Kasabach-Merritt Syndrome, Kniest Dysplasia, Koolen de-Vries Syndrome, Lennox-Gastaut syndrome, Lymphangiomatosis, Lymphangiomiomytosis, MASA Syndrome, Mast Cell Activation disorder, Mecp2 Duplication Syndrome, Mucha Habermann, Neonatal Hemochromatosis, N-glycanase deficiency, Opsoclonus Myoclonus Syndrome, Persistent genital arousal disorder, Pompe Disease, Progressive Familial Intrahepatic Cholestasis, Pseudohypoparathyroidism type 1a, PTEN Hamartoma Tumor Syndrome, Schnitzler syndrome, Scleroderma, Semi Lobar Holoprosencephany, Sjogren's Syndrome, Specific Antibody Deficiency Disease, SYNGAP 1 deficiency, Trigeminal Trophic Syndrome, Undifferentiated Connective Tissue Disease, or X-linked hypophosphatemia.

6. The synthetic mammalian mRNA expression construct of claim 1, wherein the synthetic mammalian mRNA expression construct comprises a 5' cap selected from m7GpppGm, m7GpppA, m7GpppC, an unmethylated cap analog, a dimethylated cap analog, a trimethylated cap analog, a dimethylated symmetrical cap analog, and an anti-reverse cap analog.

7. The synthetic mammalian mRNA expression construct of claim 1, wherein the synthetic mammalian mRNA expression construct comprises a Kozak sequence.

8. The synthetic mammalian mRNA expression construct of claim 1, wherein the synthetic mammalian mRNA expression construct comprises a coding sequence for encoding the protein or polypeptide, wherein the coding sequence comprises a sequence of SEQ ID NO:130, SEQ ID NO:124, SEQ ID NO:122, or a codon-optimized variant thereof.

9. The synthetic mammalian mRNA expression construct of claim 1, wherein the protein or polypeptide is a human rare disease protein.

10. The synthetic mammalian mRNA expression construct of claim 1, wherein the protein or polypeptide is human ornithine transcarbamylase (hOTC).

11. A synthetic mammalian mRNA expression construct for producing a protein or polypeptide, the synthetic mammalian mRNA expression construct comprising 5' cap m7GpppGm, a 5' UTR of AT1G58420 (SEQ ID NO:10), a Kozak sequence (SEQ ID NO:121), a coding sequence encoding human ornithine transcarbamylase (hOTC), a 3' UTR of human alpha globin (hAG) (SEQ ID NO:81), and a poly(A) tail.

12. The synthetic mammalian mRNA expression construct of claim 1, wherein the protein or polypeptide is human coagulation factor IX (F9).

13. The synthetic mammalian mRNA expression construct of claim 1, wherein the synthetic mammalian mRNA expression construct further comprises 5' cap m7GpppGm, a Kozak sequence (SEQ ID NO:121), a coding sequence encoding human coagulation factor IX (F9), a 3' UTR of human alpha globin (hAG) (SEQ ID NO:81), and a poly(A) tail.

14. The synthetic mammalian mRNA expression construct of claim 1, wherein the protein or polypeptide is selected from Aminoacylase 1, Apo A-I, Carbamoyl phosphate synthetase 1, Ornithine transcarbamylase, Plasminogen activator inhibitor type 1, Flaujeac factor (High-molecular-weight kininogen), PEPCK 1, Pyruvate kinase liver type, Alpha 1-antitrypsin, Anti-plasmin, Apolipoprotein C 2I, Butyrylcholinesterase, Complement component 2, Complement component 8 type 2, Antithrombin, Antithrombin type 2, Antithrombin type 3, Cortisone reductase, Factor VII, Factor X, Factor XI, Factor XII, Factor XIII, Fibrinogen, Fructose-1 6-bisphosphatase, Gamma aminobutyric acid transaminase, Gamma-cystathionase, Glut2, GTP cyclohydrolase I, Isolated growth hormone type 1B, Molybdenum cofactor, Prekallikrein, Proconvertin, Protein S, Pseudocholinesterase, Stuart factor, Tetrahydrobiopterin, Plasminogen, Urocanase, steroid sulfatase, cystathionine beta-synthase (CBS), Guanidinoacetate methyltransferase, Pulmonary surfactant protein B, Acid Sphingomyelinase, Adenylosuccinate Lyase, CDKL5, Glycerol Kinase, Mecp2, N-glycanase, PTEN, and SYNGAP 1.

15. The synthetic mammalian mRNA expression construct of claim 1, wherein the coding sequence for encoding the protein or polypeptide has alternative codons as compared to a native mRNA encoding the human protein or polypeptide.

16. The synthetic mammalian mRNA expression construct of claim 1, wherein the coding sequence for encoding the protein or polypeptide has a high codon adaptation index.

17. The synthetic mammalian mRNA expression construct of claim 1, wherein one or more codons of a codon-optimized coding sequence of the synthetic mammalian mRNA expression construct that encodes the protein or polypeptide have been replaced such that the occurrence of uridine monomers in the codon-optimized coding sequence is reduced as compared to the coding sequence of a native mRNA encoding the protein or polypeptide.

18. The synthetic mammalian mRNA expression construct of claim 1, wherein a coding sequence of the synthetic mRNA expression construct, the 5' UTR, or both a coding sequence of the synthetic mammalian mRNA expression construct and the 5'UTR comprise one or more chemically-modified nucleotides selected from the group of 5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 4-thiouridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine;

pseudouridine, 2'-O-methyl-pseudouridine, $N^1$-hydroxypseudouridine, $N^1$-methylpseudouridine, 2'-O-methyl-$N^1$-methylpseudouridine, $N^1$-ethylpseudouridine, $N^1$-hydroxymethylpseudouridine, and Arauridine;

5-hydroxycytidine, 5-methylcytidine, 5-hydroxymethylcytidine, 5-carboxycytidine, 5-formylcytidine, 5-methoxycytidine, 5-propynylcytidine, 2-thiocytidine;

5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuri dine, 2'-azido-2'-deoxyuridine, 4-thiouridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine;

$N^6$-methyladenosine, 2-aminoadenosine, 3-methyl adenosine, 7-deazaadenosine, 8-oxoadenosine, inosine; thienoguanosine, 7-deazaguanosine, 8-oxoguanosine, and 6-O-methylguanine.

19. A DNA template for making the synthetic mammalian mRNA expression construct of claim 1 by in vitro transcription.

20. A composition comprising the synthetic mammalian mRNA expression construct of claim 1 and a pharmaceutically acceptable carrier.

21. The composition of claim 20, wherein the carrier comprises a transfection reagent, a nanoparticle, or a liposome.

22. The composition of claim 21, wherein the nanoparticle is a lipid nanoparticle.

23. The composition of claim 22, wherein the lipid nanoparticle comprises a thiocarbamate or carbamate-containing lipid molecule.

24. The composition of claim 23, wherein the thiocarbamate or carbamate-containing lipid molecule has Formula I:

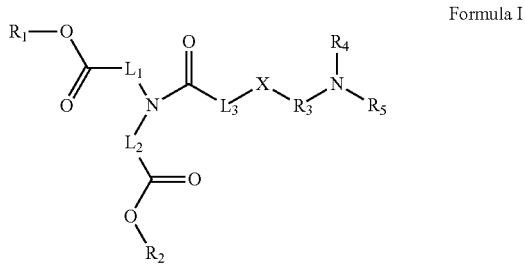

Formula I wherein
$R_1$ and $R_2$ both consist of a branched or linear alkyl consisting of 1 to 14 carbons, or an alkenyl or alkynyl consisting of 2 to 14 carbons;
$L_1$ and $L_2$ both consist of a linear alkylene or alkenylene consisting of 5 to 18 carbons, or forming a heterocycle with N;
X is S;
$L_3$ consists of a bond or a linear alkylene consisting of 1 to 6 carbons, or forming a heterocycle with N;
$R_3$ consists of a linear or branched alkylene consisting of 1 to 6 carbons; and
$R_4$ and $R_5$ are the same or different, each consisting of a hydrogen or a linear or branched alkyl consisting of 1 to 6 carbons;
or a pharmaceutically acceptable salt thereof.

25. The composition of claim 23, wherein the thiocarbamate or carbamate-containing lipid molecule is selected from ATX-001, ATX-002, ATX-003, ATX-004, ATX-005, ATX-006, ATX-007, ATX-008, ATX-009, ATX-010, ATX-011, ATX-012, ATX-013, ATX-014, ATX-015, ATX-016, ATX-017, ATX-018, ATX-019, ATX-020, ATX-021, ATX-022, ATX-023, ATX-024, ATX-025, ATX-026, ATX-027, ATX-028, ATX-031, ATX-032, ATX-0081, ATX-0095, ATX-0102, and ATX-0126.

26. A composition comprising
a synthetic mammalian mRNA expression construct for producing a protein or polypeptide, the synthetic mammalian mRNA expression construct comprising 5' cap m7GpppGm, a 5' UTR of AT1G58420 (SEQ ID NO:10), a Kozak sequence (SEQ ID NO:121), a coding sequence encoding human ornithine transcarbamylase (hOTC), a 3' UTR of human alpha globin (hAG) (SEQ ID NO:81), and a poly(A) tail, and
a pharmaceutically acceptable carrier,
wherein the carrier comprises a lipid nanoparticle comprising a lipid molecule of ATX-0081.

27. The composition of claim 23, wherein the synthetic mammalian mRNA expression construct comprises 5' cap m7GpppGm, a 5' UTR of AT1G58420 (SEQ ID NO:10), a Kozak sequence (SEQ ID NO:121), a coding sequence encoding human coagulation factor IX (hF9), a 3' UTR of human alpha globin (hAG) (SEQ ID NO:81), and a poly(A) tail, and the lipid molecule is ATX-0081.

28. An isolated cell or vector comprising the synthetic mammalian mRNA expression construct of claim 1.

* * * * *

UNITED STATES PATENT AND TRADEMARK OFFICE
CERTIFICATE OF CORRECTION

PATENT NO. : 11,015,204 B2
APPLICATION NO. : 15/994683
DATED : May 25, 2021
INVENTOR(S) : Pattraranee Limphong et al.

It is certified that error appears in the above-identified patent and that said Letters Patent is hereby corrected as shown below:

In the Specification

Column 29, Line 39, replace "Undiffentiated" with --Undifferentiated--.

In the Claims

Claim 5, Column 155, Lines 6-7, replace "Undiffentiated" with --Undifferentiated--.

Claim 18, Column 156, Lines 41-52, replace "5-hydroxycytidine, 5-methylcytidine, 5-hydroxymethylcytidine, 5-carboxycytidine, 5-formylcytidine, 5-methoxycytidine, 5-propynylcytidine, 2-thiocytidine; 5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 4-thiouridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine; N6-methyladenosine, 2-aminoadenosine, 3-methyladenosine, 7-deazaadenosine, 8-oxoadenosine, inosine;" with --5-hydroxycytidine, 5-methylcytidine, 5-hydroxymethylcytidine, 5-carboxycytidine, 5-formylcytidine, 5-methoxycytidine, 5-propynylcytidine, 2-thiocytidine;--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 130

<210> SEQ ID NO 1
<211> LENGTH: 21
<212> TYPE: DNA
<213> ORGANISM: Arabidopsis thaliana

<400> SEQUENCE: 1
cacaaagagt aaagaagaac a                                        21

<210> SEQ ID NO 2
<211> LENGTH: 21
<212> TYPE: DNA
<213> ORGANISM: Arabidopsis thaliana

```
<400> SEQUENCE: 2
aacactaaaa gtagaagaaa a                                              21

<210> SEQ ID NO 3
<211> LENGTH: 21
<212> TYPE: DNA
<213> ORGANISM: Arabidopsis thaliana

<400> SEQUENCE: 3
ctcagaaaga taagatcagc c                                              21

<210> SEQ ID NO 4
<211> LENGTH: 21
<212> TYPE: DNA
<213> ORGANISM: Arabidopsis thaliana

<400> SEQUENCE: 4
aaccaatcga agaaaccaa a                                               21

<210> SEQ ID NO 5
<211> LENGTH: 21
<212> TYPE: DNA
<213> ORGANISM: Arabidopsis thaliana

<400> SEQUENCE: 5
ctctaatcac caggagtaaa a                                              21

<210> SEQ ID NO 6
<211> LENGTH: 21
<212> TYPE: DNA
<213> ORGANISM: Arabidopsis thaliana

<400> SEQUENCE: 6
gagagagatc ttaacaaaaa a                                              21

<210> SEQ ID NO 7
<211> LENGTH: 21
<212> TYPE: DNA
<213> ORGANISM: Arabidopsis thaliana

<400> SEQUENCE: 7
tgtgtaacaa caacaacaac a                                              21

<210> SEQ ID NO 8
<211> LENGTH: 21
<212> TYPE: DNA
<213> ORGANISM: Arabidopsis thaliana

<400> SEQUENCE: 8
ccgcagtagg aagagaaagc c                                              21

<210> SEQ ID NO 9
<211> LENGTH: 21
<212> TYPE: DNA
<213> ORGANISM: Arabidopsis thaliana

<400> SEQUENCE: 9
aaaaaaaaaa gaaatcataa a                                              21

<210> SEQ ID NO 10
<211> LENGTH: 21
<212> TYPE: DNA
```

<213> ORGANISM: Arabidopsis thaliana

<400> SEQUENCE: 10
attattacat caaaacaaaa a                                              21

<210> SEQ ID NO 11
<211> LENGTH: 21
<212> TYPE: DNA
<213> ORGANISM: Arabidopsis thaliana

<400> SEQUENCE: 11
gagagaagaa agaagaagac g                                              21

<210> SEQ ID NO 12
<211> LENGTH: 21
<212> TYPE: DNA
<213> ORGANISM: Arabidopsis thaliana

<400> SEQUENCE: 12
caattaaaaa tacttaccaa a                                              21

<210> SEQ ID NO 13
<211> LENGTH: 21
<212> TYPE: DNA
<213> ORGANISM: Arabidopsis thaliana

<400> SEQUENCE: 13
gcaaacagag taagcgaaac g                                              21

<210> SEQ ID NO 14
<211> LENGTH: 21
<212> TYPE: DNA
<213> ORGANISM: Arabidopsis thaliana

<400> SEQUENCE: 14
gcgaagaaga cgaacgcaaa g                                              21

<210> SEQ ID NO 15
<211> LENGTH: 21
<212> TYPE: DNA
<213> ORGANISM: Arabidopsis thaliana

<400> SEQUENCE: 15
ttaggactgt attgactggc c                                              21

<210> SEQ ID NO 16
<211> LENGTH: 21
<212> TYPE: DNA
<213> ORGANISM: Arabidopsis thaliana

<400> SEQUENCE: 16
atcatcggaa ttcggaaaaa g                                              21

<210> SEQ ID NO 17
<211> LENGTH: 21
<212> TYPE: DNA
<213> ORGANISM: Arabidopsis thaliana

<400> SEQUENCE: 17
aaaacaaaag ttaaagcaga c                                              21

<210> SEQ ID NO 18
<211> LENGTH: 21

```
<212> TYPE: DNA
<213> ORGANISM: Arabidopsis thaliana

<400> SEQUENCE: 18
tttatctcaa ataagaaggc a                                              21

<210> SEQ ID NO 19
<211> LENGTH: 21
<212> TYPE: DNA
<213> ORGANISM: Arabidopsis thaliana

<400> SEQUENCE: 19
ggtggggagg tgagatttct t                                              21

<210> SEQ ID NO 20
<211> LENGTH: 21
<212> TYPE: DNA
<213> ORGANISM: Arabidopsis thaliana

<400> SEQUENCE: 20
tgattaggaa actacaaagc c                                              21

<210> SEQ ID NO 21
<211> LENGTH: 21
<212> TYPE: DNA
<213> ORGANISM: Arabidopsis thaliana

<400> SEQUENCE: 21
catttttcaa tttcataaaa c                                              21

<210> SEQ ID NO 22
<211> LENGTH: 21
<212> TYPE: DNA
<213> ORGANISM: Arabidopsis thaliana

<400> SEQUENCE: 22
ttacttttaa gcccaacaaa a                                              21

<210> SEQ ID NO 23
<211> LENGTH: 21
<212> TYPE: DNA
<213> ORGANISM: Arabidopsis thaliana

<400> SEQUENCE: 23
ggcgtgtgtg tgtgttgttg a                                              21

<210> SEQ ID NO 24
<211> LENGTH: 21
<212> TYPE: DNA
<213> ORGANISM: Arabidopsis thaliana

<400> SEQUENCE: 24
gtggtgaagg ggaaggttta g                                              21

<210> SEQ ID NO 25
<211> LENGTH: 21
<212> TYPE: DNA
<213> ORGANISM: Arabidopsis thaliana

<400> SEQUENCE: 25
ttgttttttt ttggtttggt t                                              21

<210> SEQ ID NO 26
```

```
<211> LENGTH: 129
<212> TYPE: RNA
<213> ORGANISM: Tobacco etch virus

<400> SEQUENCE: 26
ucaacacaac auauacaaaa caaacgaauc ucaagcaauc aagcauucua cuucuauugc    60 agcauuuaa aucauuucuu uuaaagcaaa agcaauuuuc ugaaaauuuu caccauuuac   120
gaacgauag                                                          129

<210> SEQ ID NO 27
<211> LENGTH: 30
<212> TYPE: RNA
<213> ORGANISM: Arabidopsis thaliana

<400> SEQUENCE: 27
auuauuacau caaaacaaaa agccgccacc                                    30

<210> SEQ ID NO 28
<211> LENGTH: 33
<212> TYPE: DNA
<213> ORGANISM: Synechocystis sp.

<400> SEQUENCE: 28
aacttaaaaa aaaaaatcaa aatggccgcc acc                                33

<210> SEQ ID NO 29
<211> LENGTH: 92
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucaagcuuuu ggacccucgu acagaagcua auacgacuca cuauagggaa auaagagaga    60
aaagaagagu aagaagaaau auaagagcca cc                                 92

<210> SEQ ID NO 30
<211> LENGTH: 89
<212> TYPE: RNA
<213> ORGANISM: Homo sapiens

<400> SEQUENCE: 30
aauuauuggu uaagaaguaa uauuagugcu aauucccuc cguuugyccu agcuuuucuc    60
uucugucaac cccacacgcc uuuggcaca                                     89

<210> SEQ ID NO 31
<211> LENGTH: 53
<212> TYPE: RNA
<213> ORGANISM: Mus sp.

<400> SEQUENCE: 31
cacauuugcu ucugacauag uuguguugac ucacaacccc agaaacagac auc           53

<210> SEQ ID NO 32
<211> LENGTH: 50
<212> TYPE: RNA
<213> ORGANISM: Homo sapiens

<400> SEQUENCE: 32
acauuugcuu cugacacaac uguguucacu agcaaccuca aacagacacc                50
```

```
<210> SEQ ID NO 33
<211> LENGTH: 46
<212> TYPE: RNA
<213> ORGANISM: Mus sp.

<400> SEQUENCE: 33
ugcacacaga ucaccuuucc uaucaacccc acuagccucu ggcaaa          46

<210> SEQ ID NO 34
<211> LENGTH: 66
<212> TYPE: RNA
<213> ORGANISM: Homo sapiens

<400> SEQUENCE: 34
cauaaacccu ggcgcgcucg cgggccggca cucuucuggu ccccacagac ucagagagaa     60
cccacc                                                              66

<210> SEQ ID NO 35
<211> LENGTH: 58
<212> TYPE: RNA
<213> ORGANISM: Homo sapiens

<400> SEQUENCE: 35
auaaaaagac cagcagaugc cccacagcac ugcucuucca gaggcaagac caaccaag      58

<210> SEQ ID NO 36
<211> LENGTH: 177
<212> TYPE: RNA
<213> ORGANISM: Homo sapiens

<400> SEQUENCE: 36
agacaagguu cauauuugua uggguuacuu auucucucuu guugacuaa gucaauaauc     60 agaaucagca gguuugcagu cagauuggca gggauaagca gccuagcuca ggagaaguga   120
guauaaaagc cccaggcugg gagcagccau cacagaaguc cacucauucu uggcagg      177

<210> SEQ ID NO 37
<211> LENGTH: 119
<212> TYPE: RNA
<213> ORGANISM: Homo sapiens

<400> SEQUENCE: 37
ucugccccac ccuguccucu ggaaccucug cgagauuuag aggaaagaac caguuuucag    60
gcggauugcc ucagaucaca cuaucuccac uugcccagcc cuguggaaga uuagcggcc   119

<210> SEQ ID NO 38
<211> LENGTH: 93
<212> TYPE: RNA
<213> ORGANISM: Homo sapiens

<400> SEQUENCE: 38
agauaaaaag ccagcuccag caggcgcugc ucacuccucc ccauccucuc ccucuguccc    60
ucugucccuc ugacccugca cugucccagc acc                                93

<210> SEQ ID NO 39
<211> LENGTH: 30
<212> TYPE: RNA
<213> ORGANISM: Homo sapiens

<400> SEQUENCE: 39
uauauccgug guuuccugcu accuccaacc                                    30
```

```
<210> SEQ ID NO 40
<211> LENGTH: 34
<212> TYPE: RNA
<213> ORGANISM: Homo sapiens

<400> SEQUENCE: 40
ggcaccacca cugaccuggg acagugaauc gaca                                 34

<210> SEQ ID NO 41
<211> LENGTH: 79
<212> TYPE: RNA
<213> ORGANISM: Homo sapiens

<400> SEQUENCE: 41
auucaugaaa auccacuacu ccagacagac ggcuuuggaa uccaccagcu acauccagcu     60
cccugaggca gaguugaga                                                 79

<210> SEQ ID NO 42
<211> LENGTH: 116
<212> TYPE: RNA
<213> ORGANISM: Homo sapiens

<400> SEQUENCE: 42
aauauuagag ucucaacccc caauaaauau aggacuggag augucugagg cucauucugc     60
ccucgagccc accgggaacg aaagagaagc ucuaucuccc cuccaggagc ccagcu        116

<210> SEQ ID NO 43
<211> LENGTH: 79
<212> TYPE: RNA
<213> ORGANISM: Homo sapiens

<400> SEQUENCE: 43
aggaugggaa cuaggagugg cagcaauccu uucuuucagc uggagugcuc cucaggagcc     60
agccccaccc uuagaaaag                                                 79

<210> SEQ ID NO 44
<211> LENGTH: 111
<212> TYPE: RNA
<213> ORGANISM: Homo sapiens

<400> SEQUENCE: 44 aggggggagcc cuauaauugg acaagucugg gauccuugag uccuacucag ccccagcgga    60
ggugaaggac guccuucccc aggagccgac uggccaauca caggcaggaa g             111

<210> SEQ ID NO 45
<211> LENGTH: 223
<212> TYPE: RNA
<213> ORGANISM: Unknown
<220> FEATURE:
<223> OTHER INFORMATION: Description of Unknown:
      Alanine aminotransferase 1 sequence

<400> SEQUENCE: 45 agacggguugg ggcggggccc aacugucccc agccccuuca gcccuuucug ucccucccag    60
ugaggccagc ugcggugaag agggugcucu cuugccugga guucccucug cuacggcugc   120
ccccucccag cccuggccca cuaagccaga cccagcuguc gccauuccca cuucuggucc   180
ugccaccucc ugagcugccu ucccgccugg ucuggguaga guc                     223
```

```
<210> SEQ ID NO 46
<211> LENGTH: 137
<212> TYPE: RNA
<213> ORGANISM: Human herpesvirus

<400> SEQUENCE: 46
cagaucgccu ggagacgcca uccacgcugu uuugaccucc auagaagaca ccgggaccga      60
uccagccucc gcggccggga acggugcauu ggaacgcgga uuccccgugc aagagugac     120 ucaccguccu ugacacg                                                    137

<210> SEQ ID NO 47
<211> LENGTH: 200
<212> TYPE: RNA
<213> ORGANISM: Unknown
<220> FEATURE:
<223> OTHER INFORMATION: Description of Unknown:
      ARC5-1 sequence

<400> SEQUENCE: 47
gggagaaagc uuaccauggu gccccaggcc cugcucuugg cccgcugcu gguuccccc       60 ucugcuucgg caaguccccc aucuacacca uccccgacaa gcuggggccg uggagcccca    120
ucgacaucca ccaccugucc ugccccaaca ccucguggu cgaggacgag ggcugcacca    180
accugagcgg guucuccuac                                                200

<210> SEQ ID NO 48
<211> LENGTH: 239
<212> TYPE: RNA
<213> ORGANISM: Unknown
<220> FEATURE:
<223> OTHER INFORMATION: Description of Unknown:
      ARC5-2 sequence

<400> SEQUENCE: 48
ggggcgcugc cuacggaggu ggcagccauc uccuucucgg caucaagcuu accauggugc     60
cccaggcccu gcucuugguc ccgcugcugg uguuccccu cugcuucggc aaguccccca    120
ucuacaccau ccccgacaag cuggggccgu ggagccccau cgacauccac caccugaccu    180
gccccaacaa ccucguggu cgaggacgag gcugcaccaa ccugagcggg uucuccuac      239

<210> SEQ ID NO 49
<211> LENGTH: 147
<212> TYPE: RNA
<213> ORGANISM: Mus sp.

<400> SEQUENCE: 49
gaauaaaugu auaggggga aggcaggagc cuugggggucg aggaaaacag guagggauua     60
aaaagggcac gcaagggacc aaguccagca uccuagagucc cagauuccaa acugcucaga   120
guccugugga cagaucacug cuuggca                                        147

<210> SEQ ID NO 50
<211> LENGTH: 35
<212> TYPE: RNA
<213> ORGANISM: Mus sp.

<400> SEQUENCE: 50
gacacuucug auucugacag acucaggaag aaacc                                35

<210> SEQ ID NO 51
<211> LENGTH: 158
<212> TYPE: RNA
```

<213> ORGANISM: Mus sp.

<400> SEQUENCE: 51

| ugcaaacaca gaaauggagg aggaggggaa ggaggaggag gaggagaagg aggaggaggu | 60 |
| ggugguggug guggugggau aaaacccug aggcauaaag ggcucggccg gagucagcac | 120 |
| agcccagccc uuccagagag aggcaagaga gguccacg | 158 |

<210> SEQ ID NO 52
<211> LENGTH: 189
<212> TYPE: RNA
<213> ORGANISM: Mus sp.

<400> SEQUENCE: 52

| cuaaucuccc uaggcaaggu ucauauuugu guagguuacu uauucuccuu uuguugacua | 60 |
| agucaauaau cagaaucagc agguuuggag ucagcuuggc agggaucagc agccgggguu | 120 |
| ggaaggaggg gguauaaaag ccccuucacc aggagaagcc gucacacaga uccacaagcu | 180 |
| ccugacagg | 189 |

<210> SEQ ID NO 53
<211> LENGTH: 212
<212> TYPE: RNA
<213> ORGANISM: Mus sp.

<400> SEQUENCE: 53

| auagguaauu uuagaaauag aucugauuug uaucugagac auuuuaguga aguggugaga | 60 |
| uauaagacau aaucagaaga cauaucuacc ugaagacuuu aaggggagag ucccucccc | 120 |
| caccuggccu cuggaccucu cagauuuagg ggaaagaacc aguuucgga gugaucgucu | 180 |
| cagucagcac caucucugua ggagcaucgg cc | 212 |

<210> SEQ ID NO 54
<211> LENGTH: 101
<212> TYPE: RNA
<213> ORGANISM: Mus sp.

<400> SEQUENCE: 54

| agagaggaga gccauauaaa gagccagcgg cuacagcccc agcucgccuc ugcccacccc | 60 |
| ugccccuuac cccuucauuc cuuccaccuu uuuccuucac u | 101 |

<210> SEQ ID NO 55
<211> LENGTH: 43
<212> TYPE: RNA
<213> ORGANISM: Mus sp.

<400> SEQUENCE: 55

| uuuaaaagga aagugguuac agggaggcca ugcccauggg uuu | 43 |

<210> SEQ ID NO 56
<211> LENGTH: 34
<212> TYPE: RNA
<213> ORGANISM: Mus sp.

<400> SEQUENCE: 56

| aguccuuaga cugcacagca gaacagaagg caug | 34 |

<210> SEQ ID NO 57
<211> LENGTH: 102
<212> TYPE: RNA
<213> ORGANISM: Mus sp.

<400> SEQUENCE: 57
cccccauauc cccuuggcu cccauugcuu aaauacagac uaggacaggg cucugucucc    60
ucagccucgg ucaccaccca gcucugggac agcaagcuga aa    102

<210> SEQ ID NO 58
<211> LENGTH: 62
<212> TYPE: RNA
<213> ORGANISM: Mus sp.

<400> SEQUENCE: 58 agucagaguccu ccuucgcuuc agcuccaguu cuccucauga gccaucccua aacgcagaca    60
cc    62

<210> SEQ ID NO 59
<211> LENGTH: 201
<212> TYPE: RNA
<213> ORGANISM: Homo sapiens

<400> SEQUENCE: 59
uuuccucugc ccugcuguga agggggagag aacaacccgc cucgugacag ggggcuggca    60
cagcccgccc uagcccugag gaggggcgg gacaggggga guccuauaau uggaccgguc    120
ugggauccga uccccugcuc agacccugga ggcuaaggac uuguuucgga aggagcugac    180
uggccaauca caauugcgaa g    201

<210> SEQ ID NO 60
<211> LENGTH: 95
<212> TYPE: RNA
<213> ORGANISM: Unknown
<220> FEATURE:
<223> OTHER INFORMATION: Description of Unknown:
      Alanine aminotransferase sequence

<400> SEQUENCE: 60
ggccggccac cggguuuggg agcagcccag gcucaccuua accggagcgg ugcggacggu    60
cccgcggcga cagggcuaau cucggcaggu ucgcg    95

<210> SEQ ID NO 61
<211> LENGTH: 59
<212> TYPE: RNA
<213> ORGANISM: Unknown
<220> FEATURE:
<223> OTHER INFORMATION: Description of Unknown:
      Cytochrome P450, family 1(CYP1A2) sequence

<400> SEQUENCE: 61
guccuggacu gacucccaca acucugccag ucuccagccc cugcccuuca gugguacag    59

<210> SEQ ID NO 62
<211> LENGTH: 59
<212> TYPE: RNA
<213> ORGANISM: Unknown
<220> FEATURE:
<223> OTHER INFORMATION: Description of Unknown:
      Plasminogen sequence

<400> SEQUENCE: 62
uuuaagucaa caccaggaac uaggacacag uuguccaggu gcuguuggcc agucccaac    59

<210> SEQ ID NO 63
<211> LENGTH: 81

```
<212> TYPE: RNA
<213> ORGANISM: Mus sp.

<400> SEQUENCE: 63
aaggagcugg ggaguggagu guaggcacua uaaccugaaa gacguggucc ugacaggagg    60
acaauucuau ucccuaccaa a                                              81

<210> SEQ ID NO 64
<211> LENGTH: 25
<212> TYPE: RNA
<213> ORGANISM: Mus sp.

<400> SEQUENCE: 64
accagccaga agccacaguc ucauc                                          25

<210> SEQ ID NO 65
<211> LENGTH: 218
<212> TYPE: RNA
<213> ORGANISM: Unknown
<220> FEATURE:
<223> OTHER INFORMATION: Description of Unknown:
      HNF-1alpha sequence

<400> SEQUENCE: 65
aaacagagca ggcaggggcc cugauucacu ggccgcuggg gccaggguug ggggcugggg    60
gugcccacag agcuugacua gugggauuug ggggggcagu gggugcagcg agcccggucc   120
guugacugcc agccugccgg cagguagaca ccggccgugg ugggggagg cggcuagcuc    180 aguggccuug ggccgcgugg ccugguggca gcggagcc                           218

<210> SEQ ID NO 66
<211> LENGTH: 67
<212> TYPE: RNA
<213> ORGANISM: Mus sp.

<400> SEQUENCE: 66
ggacuucagc aggacugcuc gaaacauccc acuuccagca cugccugcgg ugaaggaacc    60
agcagcc                                                              67

<210> SEQ ID NO 67
<211> LENGTH: 252
<212> TYPE: RNA
<213> ORGANISM: Mus sp.

<400> SEQUENCE: 67
agggccucgu gggggcggg aagguacugu cccauauaag ccucugcucu ugggcucaa     60 ccgcucgcac ccgcugcgcu gcacaggggg agaaaaggag cccagggugu gagccggaca   120
acuucugguc cucuccuucc aucccuuac cggcgucccc accucaggac uuuucccgca    180
ggcugcgagg ggaccacag uucguggcca cuugccuccu ggggagggcg acucuccucc    240
cauccacuca ag                                                       252

<210> SEQ ID NO 68
<211> LENGTH: 253
<212> TYPE: RNA
<213> ORGANISM: Mus sp.

<400> SEQUENCE: 68
gggggaaaaa aaacagcca aaauaugcca aaaagcuucu cacaacagcu ccucaguaga    60
agcaggggcc acuugggaaa gccaggggccu ggacgcuaau guuccaggcu acaucauagg  120
```

-continued ucccuuuucg cucagugagg ccaccaucac cacaccaugg ccacguaggc cuccagccag    180
ggcaacagga ccuggaggcc acccaagacu gcagcuggcu gccgcugggu ccccgggcca    240
gcucuuggcc ccg    253

<210> SEQ ID NO 69
<211> LENGTH: 136
<212> TYPE: RNA
<213> ORGANISM: Mus sp.

<400> SEQUENCE: 69
gaaccgcggc gaggagggggg gucggaggcc cagacuuaua aaggcugcug gacccgcgcu    60
acccgccaga ccccgccgcc cggauccccc gcgcugccug ucgccccacg ugaccacacu    120
acuaagcuug gucgcc    136

<210> SEQ ID NO 70
<211> LENGTH: 120
<212> TYPE: RNA
<213> ORGANISM: Mus sp.

<400> SEQUENCE: 70
agggacucau caaccaggcc uggccucuga guucaacgca gagcuagcug ggaaauguuc    60
cggauguugg ccaaggccag ugugacgcug ggcuccagag cggcagguug ggucggacc    120

<210> SEQ ID NO 71
<211> LENGTH: 146
<212> TYPE: RNA
<213> ORGANISM: Unknown
<220> FEATURE:
<223> OTHER INFORMATION: Description of Unknown:
      Aldehyde dehydrogenase 1 family, member L1 (ALDH1L1) sequence

<400> SEQUENCE: 71
gcugccccug ugcugacugc ugacagcuga cugacgcucg cagcuagcag guacuucugg    60
guugcuagcc cagagcccug ggccggugac ccuguuuucc cuacuucccg ucuuugaccu    120
ugggugccuu ccaaccuucu guugcc    146

<210> SEQ ID NO 72
<211> LENGTH: 219
<212> TYPE: RNA
<213> ORGANISM: Unknown
<220> FEATURE:
<223> OTHER INFORMATION: Description of Unknown:
      Fumarylacetoacetate hydrolase (FAH) sequence

<400> SEQUENCE: 72
gggugcuaaa agaaucacua ggguggggag gcggucccag uggggcgggu aggggugugu    60
gccagguggu accggguauu ggcuggagga agggcagccc ggggguucggg gcggucccug    120 aaucuaaagg cccucggcua gucugauccu ugcccuaagc auaguccgu uagccaaccc    180 ccuacccgcc gugggcucug cugcccggug cucgucagc    219

<210> SEQ ID NO 73
<211> LENGTH: 239
<212> TYPE: RNA
<213> ORGANISM: Unknown
<220> FEATURE:
<223> OTHER INFORMATION: Description of Unknown:
      Fructose bisphosphatase 1 (FBP1) sequence

<400> SEQUENCE: 73

-continued

| | |
|---|---|
| aggaggaccu uggccagcgg gcagaauggc aguugguaga ggaagggagc aaggggugu | 60 |
| uuccgggac aggggggcgg agaccuggag acuauaggcu cccccaggac ucaaguucau | 120 |
| ugaguuucug cagacacuga acggcuuuca gucuucccgc ugugacuauc accugugggc | 180 |
| uccaccugcc ugcaccuuua gucagcaccu uuagccagca ccugcgccag accccagca | 239 |

<210> SEQ ID NO 74
<211> LENGTH: 14
<212> TYPE: RNA
<213> ORGANISM: Mus sp.

<400> SEQUENCE: 74
aggcgccggu cagg                                                      14

<210> SEQ ID NO 75
<211> LENGTH: 10
<212> TYPE: RNA
<213> ORGANISM: Mus sp.

<400> SEQUENCE: 75
accaucaacc                                                           10

<210> SEQ ID NO 76
<211> LENGTH: 142
<212> TYPE: RNA
<213> ORGANISM: Mus sp.

<400> SEQUENCE: 76

| | |
|---|---|
| acccccuuuc cugcucuugc cugugaacaa ugguuaauug uucccaagag agcaucuguc | 60 |
| aguuguuggc aaaaugauaa agacauuuga aaaucugucu ucugacaaau aaaaagcauu | 120 |
| uauuucacug caaugauguu uu | 142 |

<210> SEQ ID NO 77
<211> LENGTH: 134
<212> TYPE: RNA
<213> ORGANISM: Homo sapiens

<400> SEQUENCE: 77

| | |
|---|---|
| gcucgcuuuc uugcugucca auuucuauua aagguuccuu uguucccuaa guccaacuac | 60 |
| uaaacugggg gauauuauga agggccuuga gcaucuggau ucugccuaau aaaaaacauu | 120 |
| uauuuucauu gcaa | 134 |

<210> SEQ ID NO 78
<211> LENGTH: 158
<212> TYPE: RNA
<213> ORGANISM: Xenopus sp.

<400> SEQUENCE: 78

| | |
|---|---|
| cuagugacug acuaggaucu gguuaccacu aaaccagccu caagaacacc cgaauggagu | 60 |
| cucuaagcua cauaauacca acuuacacuu acaaaauguu gucccccaaa auguagccau | 120 |
| ucguaucugc uccuaauaaa aagaaaguuu cuucacau | 158 |

<210> SEQ ID NO 79
<211> LENGTH: 106
<212> TYPE: RNA
<213> ORGANISM: Homo sapiens

<400> SEQUENCE: 79

```
uggcaucccu gugaccccuc cccagugccu cuccuggccc uggaaguugc cacuccagug    60
cccaccagcc uuguccuaau aaaauuaagu ugcaucauuu ugucug                  106

<210> SEQ ID NO 80
<211> LENGTH: 170
<212> TYPE: RNA
<213> ORGANISM: Mus sp.

<400> SEQUENCE: 80
acacaucaca accacaaccu ucucaggcua cccugagaaa aaagacaug aagacucagg    60 acucaucuuu ucuguuggug uaaaaucaac acccuaagga acacaaauuu cuuuaaacau   120
uugacuucuu gucucugugc ugcaauuaau aaaaaaugga aagaaucuac              170

<210> SEQ ID NO 81
<211> LENGTH: 110
<212> TYPE: RNA
<213> ORGANISM: Homo sapiens

<400> SEQUENCE: 81
gcuggagccu cgguagccgu uccuccugcc cgcugggccu cccaacgggc ccuccuccc    60 uccuugcacc ggcccuuccu ggucuuugaa uaaagucuga gugggcagca              110

<210> SEQ ID NO 82
<211> LENGTH: 166
<212> TYPE: RNA
<213> ORGANISM: Homo sapiens

<400> SEQUENCE: 82
ugcaaggcug gccggaagcc cuugccugaa agcaagauuu cagccuggaa gagggcaaag   60
uggacgggag uggacaggag uggaugcgau aagauguggu uugaagcuga ugggugccag   120
cccugcauug cugagucaau caauaaagag cuuucuuuug acccau                 166

<210> SEQ ID NO 83
<211> LENGTH: 80
<212> TYPE: RNA
<213> ORGANISM: Homo sapiens

<400> SEQUENCE: 83
aauguucuua uucuuugcac cucuuccuau uuuuggguuug ugaacagaag uaaaauaaa   60 uacaaacuac uuccaucuca                                               80

<210> SEQ ID NO 84
<211> LENGTH: 178
<212> TYPE: RNA
<213> ORGANISM: Homo sapiens

<400> SEQUENCE: 84
ccacaccccc auuccccacc uccagauaaa gcuucaguua uaucucacgu gucuggaguu   60
cuuugccaag agggagaggc ugaaauccccc agccgccuca ccugcagcuc agcuccaucc  120
uacuugaaac cucaccuguu cccaccgcau uuucuccugg cguucgccug cuagugug     178

<210> SEQ ID NO 85
<211> LENGTH: 101
<212> TYPE: RNA
<213> ORGANISM: Homo sapiens

<400> SEQUENCE: 85
aaccuaccug cccugcccc guccccuccc uuccuuauuu auuccugcug cccagaaca     60
```

```
uaggucuugg aauaaaaugg cugguucuuu uguuuuccaa a                         101
```

<210> SEQ ID NO 86
<211> LENGTH: 234
<212> TYPE: RNA
<213> ORGANISM: Homo sapiens

<400> SEQUENCE: 86

```
acuaaguuaa auauuucugc acaguguucc cauggccccu ugcauuuccu ucuuaacucu      60 cguuacacg ucauugaaac uacacuuuuu uggucuguuu uugugcuaga cguuaaguuc      120
cuugggggca gggccuuugu cugcucucauc ucguauucc caaaugccua acaguacaga    180
gccaugacuc aauaaauaca uguuaaaugg augaaugaau uccucugaaa cucu           234
```

<210> SEQ ID NO 87
<211> LENGTH: 143
<212> TYPE: RNA
<213> ORGANISM: Homo sapiens

<400> SEQUENCE: 87

```
acgccgaagc cugcagccau gcgacccac gccaccccgu gccuccugcc uccgcgcagc      60
cugcagcggg agacccuguc cccgcccag ccguccuccu ggguggacc cuaguuuaau      120 aaagauucac caaguuucac gca                                             143
```

<210> SEQ ID NO 88
<211> LENGTH: 171
<212> TYPE: RNA
<213> ORGANISM: Unknown
<220> FEATURE:
<223> OTHER INFORMATION: Description of Unknown:
      Alanine aminotransferase 1 sequence

<400> SEQUENCE: 88

```
gcacccagc uggggccagg cugggucgcc cuggacugug ugcucaggag cccugggagg      60
cucuggagcc cacuguacuu gcucuugaug ccuggcgggg uggguggg ggggugcugg      120 gccccugccu cucugcaggu cccuaauaaa gcugugugc agucugacuc c               171
```

<210> SEQ ID NO 89
<211> LENGTH: 110
<212> TYPE: RNA
<213> ORGANISM: Unknown
<220> FEATURE:
<223> OTHER INFORMATION: Description of Unknown:
      MALAT sequence

<400> SEQUENCE: 89

```
gauucgucag uagggguugua aagguuuuuc uuuuccugag aaaacaaccu uuuguuuucu    60
cagguuuugc uuuuuggccu uucccuagcu uuaaaaaaaa aaaagcaaaa                110
```

<210> SEQ ID NO 90
<211> LENGTH: 74
<212> TYPE: RNA
<213> ORGANISM: Unknown
<220> FEATURE:
<223> OTHER INFORMATION: Description of Unknown:
      ARC3-1 sequence

<400> SEQUENCE: 90

```
ggacuaguua uaagacugac uagcccgaug ggccucccaa cgggcccucc uccccuccuu    60
gcaccgagau uaau                                                       74
```

```
<210> SEQ ID NO 91
<211> LENGTH: 100
<212> TYPE: RNA
<213> ORGANISM: Homo sapiens

<400> SEQUENCE: 91
ggguggcauc ccugugaccc cucccccagug ccucuccugg cccuggaagu ugccacucca      60
gugcccacca gccuuguccu aauaaaauua aguugcauca                           100

<210> SEQ ID NO 92
<211> LENGTH: 105
<212> TYPE: RNA
<213> ORGANISM: Mus sp.

<400> SEQUENCE: 92
ccacucacca gugucucugc ugcacucucc ugugccuccc ugcccccugg caacugccac       60
cccugcgcuu uguccuaaua aaauuaagau gcaucauauc acccg                     105

<210> SEQ ID NO 93
<211> LENGTH: 105
<212> TYPE: RNA
<213> ORGANISM: Mus sp.

<400> SEQUENCE: 93
gcugccuucu gcggggcuug ccuucuggcc augcccuucu ucucucccuu gcaccuguac       60
cucuuggucu uugaauaaag ccgaguagg aagaaaaaaa aaaaa                      105

<210> SEQ ID NO 94
<211> LENGTH: 163
<212> TYPE: RNA
<213> ORGANISM: Mus sp.

<400> SEQUENCE: 94
uucagggcuc acuagaaggc ugcacauggc agggcaggcu gggagccaug gaagagggg       60 aaguggaagg guugggcuau acucugaugg guucuagccc ugcacugcuc agucaacaau     120
aaaaaaaugu gcuuuggacc cauaaaaaaa aaaaaaaaaa aaa                       163

<210> SEQ ID NO 95
<211> LENGTH: 604
<212> TYPE: RNA
<213> ORGANISM: Mus sp.

<400> SEQUENCE: 95
gagacucagc ccaggaggac caggaucuug ccaaagcagu agcaucccau uuguaccaaa       60 acaguuucu ugcucuauaa accguuuag cagcucagga agaugccgug aagcauucuu       120
auuaaaccac cugcuauuuc auucaaacug uguucuuuu uuauuccuc auuuuucccc        180 ccugcuccua aaaccccaaaa ucuucuaaag aauucuagaa gguaugcgau caaacuuuuu    240
aaagaaagaa aauacuuuuu gacucauggu uuaaaggcau ccuuuccauc uuggggaggu     300 cauggggugcu ccuggcaacu ugcuugagga agauagguca gaaagcagag uggaccaacc    360
guucaauguu uuacaagcaa aacauacacu aagcaugguc uguagcuauu aaaagcacac    420
aaucugaagg gcguagaug cacaguagug uuucccaga gcauguucaa aagcccuggg     480
uucaaucaca auacguaaaa guaggccaaa aacauucug aaaaugaaau auuugggguu    540 uuuuuauaa ccuuuaguga cuaaauaaag acaaaucuaa gagacuaaaa aaaaaaaaaa     600
```

```
aaaa                                                             604

<210> SEQ ID NO 96
<211> LENGTH: 561
<212> TYPE: RNA
<213> ORGANISM: Mus sp.

<400> SEQUENCE: 96
aauauucuua aucuuugcac cuuuuccuac uuugguguuu ugaauagaa guaaaaauaa     60 auacgacugc caccucacga gaauggacuu uccacuuga agacgagaga cuggaguaca    120
gaugcuacac cacuuuuggg caagugaagg gggagcagcc agccacggug gcacaaaccu    180
auauccuggu gcuuuugaag guagaagcag ggcggucagg aguuaaggcc aguugaggcu    240
gggcugcaga gugaaagacc augcucaag auggucuuuc uccucccaa aguagaaaag      300 aaaaccauaa aaacaagagg uaaauauauu acuauuucau cuuagaggau agcaggcauc    360
uugaaagggu agagggaccu uaaauucuca uuauugcccc cauacuacaa acuaaaaaac    420
aaacccgaau caaucccca uaaagacaga gauucaaaua agaguauuaa acguuuauu     480 ucucaaaacca cucacaugca uaauguucuu auacacagug ucaaaauaaa gagaaaugca    540
uuuuuauaca aaaaaaaaaa a                                              561

<210> SEQ ID NO 97
<211> LENGTH: 46
<212> TYPE: RNA
<213> ORGANISM: Mus sp.

<400> SEQUENCE: 97
cuacagccca gcccucuaau aaagcuucag uuguauuuca cccauc                    46

<210> SEQ ID NO 98
<211> LENGTH: 347
<212> TYPE: RNA
<213> ORGANISM: Mus sp.

<400> SEQUENCE: 98
aaaguucugc ugcacgaaga uuccuccugc ggcgggggga uugcuccucc ucuggcuugg     60
aaaccuagcc uagaaucaga uacacuuucu uuagaguaaa gcacaagcug augaguuacg    120
acuuugugaa auggauagcc uugaggggag gcgaaaacag gucccccaag gcuaucagau    180
gucagugcca auagacugaa acaagucugu aaaguuagca gucaggggug uugguugggg    240
ccggaagaag agaccacug aaacuguagc cccuuaucaa aacauauccu ugcuugaaag    300
aaaaauacca aggacagaaa augccauaaa aucuugacuu ugcacuc                  347

<210> SEQ ID NO 99
<211> LENGTH: 124
<212> TYPE: RNA
<213> ORGANISM: Mus sp.

<400> SEQUENCE: 99
ccuagagcca cauccugacc ucucuacacc ccugcagccc cucaaccccca uuauuuauuc     60 cugcccuccc caccaaugac cuugaaauaa agacgauuuu auuuucaaaa aaaaaaaaaa    120
aaaa                                                                 124

<210> SEQ ID NO 100
<211> LENGTH: 380
<212> TYPE: RNA
<213> ORGANISM: Mus sp.
```

```
<400> SEQUENCE: 100
ccacccuaaa augcauccu ccuucugaa uuggguuccu uccauuaaac acaggcuggc      60
cuggcucgug ccugaugcua cagcaaguuc uugacucugu ggguugugug uguguguug    120 ugugugugug ugugugugug ugugugugug ugugugugug ugugugugug ugugugugug    180
ugugucuuua ugcccugagu uuguguggga cuugagauca uaguaugucu ugauaucucc    240
uccagccaug caaauagguu guggguagag gacuguggcu gagaccacag acucuggucc    300
aagaaccauc ugcucuaaaa aaauaaauc ugucaucucu ggaaaauaaa gaggacaugc    360
ucaaugacuc aggguccagc                                               380

<210> SEQ ID NO 101
<211> LENGTH: 217
<212> TYPE: RNA
<213> ORGANISM: Mus sp.

<400> SEQUENCE: 101
cugaaggguu agaaaguggg ggcucuguuu ucuuugcucg guuauccgag aagaaagaca     60
aaacggaaga ugaaggcugc acggaucuug ugaacuuuuu aaaacuuuca aggugcuauu    120 ccauguucu uuguacugua gcuaaaugua acugaugua guuacugcuu ugaaaaaaua    180 aaguuuaca uuuuuuccac ccuuuaaaaa aaaaaaa                              217

<210> SEQ ID NO 102
<211> LENGTH: 141
<212> TYPE: RNA
<213> ORGANISM: Unknown
<220> FEATURE:
<223> OTHER INFORMATION: Description of Unknown:
      Apolipoprotein E sequence

<400> SEQUENCE: 102
guauccuucu ccugccugc aacaacaucc auauccagcc aggugcccu gucucaagca      60 ccucucuggc ccucuggugg cccuugcuua auaaagauuc uccgagcaca uucugagucu    120
cugugaguga uucaaaaaaa a                                              141

<210> SEQ ID NO 103
<211> LENGTH: 1932
<212> TYPE: RNA
<213> ORGANISM: Unknown
<220> FEATURE:
<223> OTHER INFORMATION: Description of Unknown:
      Alanine aminotransferase sequence

<400> SEQUENCE: 103
ggacgccuca ggcaccggag ccagacccuc ccaagaccac ccaggccuuc cucaaggacu     60
cugccucaga cccagacag gccaccaacg cuguucaucu ucauuuccc aaggagacuu    120 cuuucuuugu gccuugaugu uugagaguuc uucgagcaaa caguggcuuu gcaaugucuc    180
acaggcccug uuuuuguuuu uguuuugguu uguuuugu uguucuuuu uuaaaugca    240 accaaaguag agucaaccug cucggcagau guacuggau ucucugaauc gcuauucugu     300
uuggagaguu ccuuugggu uuaagcagcc agauacaug gaaaugagau uaugucagau     360
cuggagaaac aagcaggugu ugggaaauau ugacuugac augauaaggg cugggaaucc    420
agaaaucaau agugagaucc augaaaucaa acccugacca gugugaaaau guagcuuuu    480 ggacaguaag ccugcaaguc uagugagaac ucagagaaag cugaccauuc uggucugaag   540
```

| | |
|---|---:|
| auaggcagcg caucacaggc aagaauaucg aagucaguag uaggacaggg gucacaucag | 600 |
| auaccagcuc aaauugcacu agcuaucuag aacaguuuuc uccagguuug ccugagccuu | 660 |
| gaugcauacc aucgcccucu gcuggucgca gcagagauaa gcaagggcug aaaauggagg | 720 |
| caauccuuuc ccaaggcccu gaaaguugu uuucauggu ucaaacugaa uuuggcucau | 780 |
| uuguaacuaa cugaucacgg ugccugguua cacuggcugc caagaaggag cgcaugcaau | 840 |
| cugauucagu gcucucuuca caucaguuuc cugccuccca cccucaucug cggacagcau | 900 |
| ccuaucucau caggcuuccc ugugugucac aaaguagcag ccaccaagca aauauauucc | 960 |
| uugaauuagc acaccugggu gggccaugug cgcaccaagg aaacaggugc uauagggagc | 1020 |
| gccaggccag gcuugucucu aacugucuc guucuucagu gagaguggga aagcuguccg | 1080 |
| gagcucccgc gcaggagccu gguacccac gcagcgaguc aagggaguuu ucggagccag | 1140 |
| agagagaaag augugaaggc uggaguaa ggcugaaacc agccuccugc ccuauagucc | 1200 |
| cacacugcag ggggugcgac uuuaaaacag aacuucaagu uguuaacacu cacaagcauu | 1260 |
| gcauuacugu gaaggaagua gccgcaucca uaacaggaug ugauggucua cagcuuuucc | 1320 |
| uuuaaaagcu gaaaaggguac caugugugcu cgcuaggcau auaaccaga uaugcuccag | 1380 |
| aguucugaga ucuuccaug aaagguuaac uagaagcuag aauauuuuuu uauauuuugg | 1440 |
| uaacaauugg cuuuuuucau gggggaggg gaguagaggg uuaguauuua uaguccuaac | 1500 |
| aaguccaaaa auuuuuauaa guguucuucag auuuauaaaua accccuccaaa uuuugcaaug | 1560 |
| uuuacauguu uuuuuuuaa gaugacaaau augcuugauu ugcuuuuaa auaaaaguuu | 1620 |
| agcuguucua agagauuaac uucaaguagg auggcuggu augauaguuu ggauuuucua | 1680 |
| cagguucugu ugccaugccu uuugggguuc agcaucacuc gagucgcagc augugggugg | 1740 |
| ggcuguggaa accuggccag gcuggaccug gucagccaca ccucagagac auuguuccca | 1800 |
| uuuggaugug agcaggcgca ggccugcaug cucuuuccua cuuagcauca ucaguucuuc | 1860 |
| cgccuccuua gcauggucu uuguaacagc caugcuggga agcucugaac aauaaaauac | 1920 |
| uuccagagug gu | 1932 |

<210> SEQ ID NO 104
<211> LENGTH: 291
<212> TYPE: RNA
<213> ORGANISM: Unknown
<220> FEATURE:
<223> OTHER INFORMATION: Description of Unknown:
      Cytochrome P450, family 1(CYP1A2) sequence

<400> SEQUENCE: 104

| | |
|---|---:|
| agauugucga ggcaucggug gggccgucac ccuuguuucu uuuccuuuuu uaaaaaaaaa | 60 |
| aaaaaaacag cuuuuuuuuu uuugagagau acaauucuuu ccccauuuaa uucaucucca | 120 |
| agcaauuuua caauaguguc uaucauguuc accccauaac ccauacucau uaggacuuau | 180 |
| gauuuaagau uccuccuacc cugucuugcu ugccgcaccu caugcuaauc uaguuuuga | 240 |
| cucaauagau uugccuacuc uggcugucuc auauaaaucg aaugaauuau g | 291 |

<210> SEQ ID NO 105
<211> LENGTH: 257
<212> TYPE: RNA
<213> ORGANISM: Unknown
<220> FEATURE:
<223> OTHER INFORMATION: Description of Unknown:
      Plasminogen sequence

<400> SEQUENCE: 105

```
cuagguggaa ggccgagcaa aaccucugcu uacuaaagcu uacugaauau ggggagaggg      60
cuuagggugu uuggaaaaac ugacaguaau caaacuggga cacuacacug aaccacagcu    120
uccugucgcc ccucagcccc uccccuuuuu uuguauuauu ugggguaaaa uuuuccuguc    180
uguggacuuc uggauuuugu gacaauagac caucacugcu gugaccuuug uugaaaauaa    240
acucgauacu uacuuug                                                   257

<210> SEQ ID NO 106
<211> LENGTH: 282
<212> TYPE: RNA
<213> ORGANISM: Mus sp.

<400> SEQUENCE: 106
agaauggccu gagccuccag uguugagugg agacuuuuca ccaggacucc agcaucaucc     60
cuuccuaucc auacagacuc ccaugccaag gucugugauc ugcucccac cugucucaca    120 gagaagugca aucccguucu cuccagcaug uuaccuagga uaacucauca agaaucaaag    180
acuuucuuua aauuucucuu ugccaacaca uggaaauucu ccaugauuuu cuuuccuguc    240
cuguucaaua aaugauuaca cuugcacuua aaaaaaaaaa aa                       282

<210> SEQ ID NO 107
<211> LENGTH: 509
<212> TYPE: RNA
<213> ORGANISM: Mus sp.

<400> SEQUENCE: 107
cuccuuggau agcccaaccc gucccaagaa ggaagcuacg gccugugaag cuguucuaug     60
gacuuuccug cuauucuugu guaagggaag agaaugagau aaagagagag ugaagaaagc    120 agaggggag guaaaugaga gaggcuggga aaggggaaac agaaagcagg gccgggggaa     180
gagucuaagu uagagacuca caaagaaacu caagaggggc ugggcagugc agucacaguc    240
aggcagcuga ggggcagggu gucccugagg gaggcgaggc ucaggccuug ucccgucuc    300 cccguagcug ccuccugucu gcaugcauuc ggucugcagu acuacacagu agguaugcac    360
augagcacgu aggacacgug aaugugccgc augcaugucu gugccugugu guccaucauu    420
ggcacuguug cucacuugug cuuccuguga gcacccuguc uugguuucaa uuaaaugaga    480
aacaugguca aaaaaaaaaa aaaaaaaa                                       509

<210> SEQ ID NO 108
<211> LENGTH: 1098
<212> TYPE: RNA
<213> ORGANISM: Unknown
<220> FEATURE:
<223> OTHER INFORMATION: Description of Unknown:
      HNF-1alpha sequence

<400> SEQUENCE: 108
ccguggugac ugccucccag gagcuggguc cccagggccu gcacugccug cauaggggu     60 gaggagggcc gcagccacac ugccuggagg auaucugagc cugccaugcc accugacaca    120
ggcugcuggc cuucccagaa gucuacgcau ucauugacac ugcugucccu ccaucaucag    180
gaagggaugg cucugaggug ucucagccug acaagcgagc cucgaggagc uggaggacgg    240
cccaaucugg gcaguauugu ggaccaccau cccugcuguu uagaauagga aauuuaaugc    300
uuggacagag agugggaag cucgguggugc ccgcaccccc ccagcagag ccugcaggcc    360 uucaaggauc ugugcugagc ucugaggccc uagaucaaca cagcugccug cugccuccug    420
```

```
caccuccccca ggccauucca cccugcacca gagacccacg ugccuguuug aggauuaccc     480
uccccaccac ggggauuucc uaccagcug uucugcuagg cucggagcu gaggggaagc        540 cacucggggc ucuccuaggc uuuccccuac caagccaucc cuucucccag ccccaggacu      600
gcacuugcag gccaucuguu cccuuggaug ugucuucuga ugccagccug gcaacuugca      660
uccacuagaa aggccauuuc agggcucggg uugucauccc uguuccuuag gaccugcaac      720
ucaugccaag accacaccau ggacaauucca cccucucugcc uguaggcccc ugacaacuuc    780
cuuccugcua ugagggagac cugcagaacu cagaagucaa ggccugggca gugucuagug      840 gagagggguac caagaccagc agagagaagc caccuaagug gccuggggc uagcagccau      900 ucugagaaau ccugggucc gagcagccca gggaaacaca gcacacauga cugucuccuc      960
gggccuacug cagggaaccu ggccuucagc cagcuccuuu gucauccugg acuguagccu     1020
acggccaacc auaagugagc cuguauguuu auuaacuuu uaguaaaguc aguaaaaagc      1080
aaaaaaaaaa aaaaaaaa                                                  1098

<210> SEQ ID NO 109
<211> LENGTH: 201
<212> TYPE: RNA
<213> ORGANISM: Mus sp.

<400> SEQUENCE: 109
acaucuccag aaggaagagu ggacaaaaaa augguguugac ucuuuggugu gagccuuuug     60
gcuuaacugu aacugcuagu acuuuaacca cauggugaag auguccaugu gagauuucua    120
uaccuuagga auaaaaacuu ucaacuauu ucucuucucc uaagucugcuu uuuuuuauu     180 aaaaaauacu uuuuuccauu u                                              201

<210> SEQ ID NO 110
<211> LENGTH: 739
<212> TYPE: RNA
<213> ORGANISM: Mus sp.

<400> SEQUENCE: 110
ucuuuccagc cccacccuac aagugucucu cuaccaaggu caauccacac cccagugaug      60
uuagcagacc cuccaucuuu gagugguccu uucacccuua agccuuuugc ucuggagcca     120
uguucucagc uucagcacaa uuuacagcuu uccaagcau cgccccgugg gauguuuuga     180
gacuucucuc ucaauggug acaguugguc accuguucu gcuucagggu uucaguacug      240 cucagguguug uuuaagagaa ucaaaaguuc uaugguuu gucugggauc aauagggaaa     300
cacagguagc caacuaggag gaaaugacu gaaugcuagu acccaagacc uugagcagga     360
aagucaccca gacaccucug cuuucuuuug ccaucgacc ugcagcacug ucaggacaug      420
gccuguggcu gugguucaa acaccccucc cacaggacuc acuuugcccc aacaauucag      480
auugccuaga aauaccuuuc ucuuaccugu uuguuauuua ucaauuuuuc ccaguauuuu     540
uauacggaaa aaauuguauu gaagacacuu uguaugcagu ugauaagagg aauucaguau     600
aauuaugguu ggugauauau uuauaaagca caugccaacg cuuuacuacu gugaaagac      660 aagguuuuua auaaaagau uuacauucca ugaugggac gucauucuu uuuuuuuua        720 acaucaugug uuuggagag                                                 739

<210> SEQ ID NO 111
<211> LENGTH: 252
<212> TYPE: RNA
```

<213> ORGANISM: Mus sp.

<400> SEQUENCE: 111

```
caacgucuag gaugugaagu uugaagauuu cugauuagcu uucauccggu cuucaucucu      60
auuuaucuua gaaguuuagu uuccccacc uccccuaccu ucucuaggug gacauuaaac     120
caucguccaa aguacaugag agucacugac ucuguucaca caacuguaug ucuuacugaa    180
ggucccugaa agauguuuga ggcuugggau uccaaacuug guuuauuaaa cauauaguca    240
ccaucuuccu au                                                        252
```

<210> SEQ ID NO 112
<211> LENGTH: 188
<212> TYPE: RNA
<213> ORGANISM: Mus sp.

<400> SEQUENCE: 112

```
gcccaucacc ccaccugggu ggcuggcauu caggaaccua acugaagucu ucucugcacc     60
cccugccaac cccuucccau cuacaguguu aguguccccg gugccacaga gaagagccca    120
guuggaagcu auacccgauu uaauuccaga auuagucaac caucaauuag aauccaucca    180
cccccuc                                                              188
```

<210> SEQ ID NO 113
<211> LENGTH: 254
<212> TYPE: RNA
<213> ORGANISM: Mus sp.

<400> SEQUENCE: 113

```
gcauccucuc accagacuau gcccuccugg aggggcuggg aauauagcaa gaacgaaaag     60
acugugcaag gccuagagcc agcaaagaug cugauguagc caggccaugc cggaaggagc    120
agggugaagc uuccccucuc ccuacaaaug gaaccuugug gaaacaggau gcuaaacacc    180
uucugaugga gcguugccu gcaggccacu ggucuuuggg aauuuucaau aaagugcuug    240
cgaggaaucu ccua                                                      254
```

<210> SEQ ID NO 114
<211> LENGTH: 243
<212> TYPE: RNA
<213> ORGANISM: Unknown
<220> FEATURE:
<223> OTHER INFORMATION: Description of Unknown:
      Aldehyde dehydrogenase 1 family, member L1 (ALDH1L1) sequence

<400> SEQUENCE: 114

```
agccaagacu gugauacuuc uccuguaccc uguugaccuc agggagugcu gacccugucu     60
ggugacuuag cacccuccug uccccagcac ugcccuuuc agcugcugga gcucuuggcc    120
uggaccccug cuggugacag gacacccucu gaacaaucag aaguggcucc aaguggagug    180
agcagucaug uccccauga auaaaaauug ugagcagagg ucgccuacaa aaaaaaaaa    240
aaa                                                                  243
```

<210> SEQ ID NO 115
<211> LENGTH: 118
<212> TYPE: RNA
<213> ORGANISM: Unknown
<220> FEATURE:
<223> OTHER INFORMATION: Description of Unknown:
      Fumarylacetoacetate hydrolase (FAH) sequence

<400> SEQUENCE: 115

```
agcuccggaa gucacaagac acacccuugc cuuaugagga ucaugcuacc acugcaucag    60
ucaggaauga auaaagcuac uuugauugug ggaaaugcca cagaaaaaaa aaaaaaaa    118
```

<210> SEQ ID NO 116
<211> LENGTH: 223
<212> TYPE: RNA
<213> ORGANISM: Unknown
<220> FEATURE:
<223> OTHER INFORMATION: Description of Unknown:
      Fructose bisphosphatase 1 (FBP1) sequence

<400> SEQUENCE: 116

```
aggccagccu ugcccugcc ccagagcaga gcucaaguga cgcuacucca uucugcaugu    60
uguacauucc uagaaacaaa ccuaacagcg uggauaguuu cacagcuuaa ugcuuugcaa   120
ugcccaaggu cacuucaucc ucaugcuaua augccacugu aucagguaau auauauuuug   180
aguaggugaa ggagaaauaa acacaucuuu ccuuuauaaa uua                    223
```

<210> SEQ ID NO 117
<211> LENGTH: 146
<212> TYPE: RNA
<213> ORGANISM: Mus sp.

<400> SEQUENCE: 117

```
guuucuccgg cucccagaag cccaugcuca ggcaauggcc ccuacccuaa gaccaucccc    60
uaaugcagau auugcauuug ggugcagaug uggggggucgg gcaaacggag uaaacaauac   120
agucugcauu ccucaaaaaa aaaaaa                                        146
```

<210> SEQ ID NO 118
<211> LENGTH: 216
<212> TYPE: RNA
<213> ORGANISM: Mus sp.

<400> SEQUENCE: 118

```
gcccccaucc acacauggac cacgcaaagu gcuggacaca ucagucaucu ccaacuggcu    60
gaaaggcuga accucagggc uccacccacg ucauggccac gcccccucua uuacaagagu   120
ccgccuugcc ugagucccuc cugcugaggua aagcuacccu cccaggucca aaaaaaaaaa   180
aaaaaaaaaa aaaaaaaaaa aaaaaaaaaa aaaaaa                              216
```

<210> SEQ ID NO 119
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119

```
auaagugaa                                                            9
```

<210> SEQ ID NO 120
<211> LENGTH: 6
<212> TYPE: DNA
<213> ORGANISM: Unknown
<220> FEATURE:
<223> OTHER INFORMATION: Description of Unknown:
      Kozak sequence

<400> SEQUENCE: 120

```
gccacc                                                               6
```

```
<210> SEQ ID NO 121
<211> LENGTH: 9
<212> TYPE: DNA
<213> ORGANISM: Unknown
<220> FEATURE:
<223> OTHER INFORMATION: Description of Unknown:
      Kozak sequence

<400> SEQUENCE: 121 gccgccacc                                                             9

<210> SEQ ID NO 122
<211> LENGTH: 582
<212> TYPE: RNA
<213> ORGANISM: Homo sapiens

<400> SEQUENCE: 122 auggggugc  acgaaugucc  ugccuggcug  uggcuucucc  uguccugcu   gucgcuccu    60 cugggccucc  cagaccuggg  cgccccacca  cgccucaucu  gugacagccg  aguccuggag  120
agguaccucu  uggaggccaa  ggaggccgag  aauaucacga  cgggcugugc  ugaacacugc  180
agcuugaaug  agaauaucac  ugucccagac  accaaaguua  auuucuaugc  cuggaagagg  240
auggaggucg  ggcagcaggc  cguagaaguc  uggcagggcc  uggcccugcu  gucggaagcu  300
guccugcggg  gccaggcccu  guuggucaac  ucuucccagc  cguggagcc   ccugcagcug  360 caugggauaa  agccgucag  uggccuucgc  agccucacca  cucugcuucg  ggcucuggga  420
gcccagaagg  aagccaucuc  cccuccagau  gcggccucag  cugcuccacu  ccgaacaauc  480
acugcugaca  cuuccgcaa   acucuuccga  gucuacucca  auuccuccg   gggaaagcug  540 aagcuguaca  cagggggaggc  cugcaggaca  ggggacagau  ga                    582

<210> SEQ ID NO 123
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123 auaagugaa                                                             9

<210> SEQ ID NO 124
<211> LENGTH: 1386
<212> TYPE: RNA
<213> ORGANISM: Homo sapiens

<400> SEQUENCE: 124
augcagcgcg  ugaacaugau  cauggcagaa  ucaccaggcc  ucaucaccau  cugccuuuua  60
ggauaucuac  ucagugcuga  auguacaguu  uuucuugauc  augaaaacgc  caacaaaauu  120
cugaaucggc  caaagaggua  uaauucaggu  aaauuggaag  aguuuguuca  agggaaccuu  180
gagagagaau  guaaggaaga  aaaguguagu  uuugaagaag  cacgagaagu  uuugaaaac   240 acugaaagaa  caacugaauu  uuggaagcag  uauguugaug  gagaucagug  ugagccaau   300 ccauguuuaa  auggcggcag  uugcaaggau  gacauuaauu  ccuaugaaug  uugguguccc  360
uuuggauuug  aaggaaagaa  cugugaauua  gauguaacau  guaacauuaa  gaauggcaga  420
ugcgagcagu  uuguaaaaaa  uagugcugau  aacaagguug  uuugcuccug  uacugaggga  480
```

| | |
|---|---:|
| uaucgacuug cagaaaacca gaaguccugu gaaccagcag ugccauuucc augugggaaga | 540 |
| guuucuguuu cacaaacuuc uaagcucacc cgugcugaga cuguuuuccc ugaugugggac | 600 |
| uauguaaauu cuacugaagc ugaaaccauu uuggauaaca ucacucaaag cacccaauca | 660 |
| uuuaaugacu ucacucgggu uguuggugga gaagaugcca aaccagguca auucccuugg | 720 |
| cagguuguuu ugaauggguaa aguugaugca uucuguggag gcucuaucgu uaaugaaaaa | 780 |
| uggauuguaa cugcugccca cuguguugaa acugguguua aaauuacagu gucgcaggu | 840 |
| gaacauaaua uugaggagac agaacauaca gagcaaaagc gaaaugugau ucgaauuauu | 900 |
| ccucaccaca acuacaaugc agcuauuaau aaguacaacc augacauugc ccuucuggaa | 960 |
| cuggacgaac ccuuagugcu aaacagcuac guuacaccua uuugcauugc ugacaaggaa | 1020 |
| uacacgaaca ucuuccucaa auuuggaucu ggcuauguaa guggcugggg aagagucuuc | 1080 |
| cacaaaggga gaucagcuuu aguucuucag uaccuuagag uuccacuugu ugaccgagcc | 1140 |
| acaugucuuc gaucuacaaa guucaccauc uauaacaaca uguucugugc uggcuuccau | 1200 |
| gaaggaggua gagauucaug ucaaggagau agugggggac cccauguuac ugaaguggaa | 1260 |
| gggaccaguu ucuuaacugg aauuauuagc uggggugaag agugugcaau gaaaggcaaa | 1320 |
| uauggaauau auaccaaggu aucccgguau gucaacugga uuaaggaaaa aacaaagcuc | 1380 |
| acuuaa | 1386 |

<210> SEQ ID NO 125
<211> LENGTH: 582
<212> TYPE: DNA
<213> ORGANISM: Homo sapiens

<400> SEQUENCE: 125

| | |
|---|---:|
| atgggggtgc acgaatgtcc tgcctggctg tggcttctcc tgtccctgct gtcgctccct | 60 |
| ctgggcctcc cagtcctggg cgccccacca cgcctcatct gtgacagccg agtcctggag | 120 |
| aggtacctct tggaggccaa ggaggccgag aatatcacga cgggctgtgc tgaacactgc | 180 |
| agcttgaatg agaatatcac tgtcccagac accaaagtta atttctatgc ctggaagagg | 240 |
| atggaggtcg gcagcaggc cgtagaagtc tggcagggcc tggccctgct gtcggaagct | 300 |
| gtcctgcggg gccaggccct gttggtcaac tcttcccagc cgtgggagcc cctgcagctg | 360 |
| catgtggata agccgtcag tggccttcgc agcctcacca ctctgcttcg ggctctggga | 420 |
| gcccagaagg aagccatctc ccctccagat gcggcctcag ctgctccact ccgaacaatc | 480 |
| actgctgaca ctttccgcaa actcttccga gtctactcca atttcctccg gggaaagctg | 540 |
| aagctgtaca caggggaggc ctgcaggaca ggggacagat ga | 582 |

<210> SEQ ID NO 126
<211> LENGTH: 582
<212> TYPE: DNA
<213> ORGANISM: Artificial Sequence
<220> FEATURE:
<223> OTHER INFORMATION: Description of Artificial Sequence: Synthetic
  polynucleotide

<400> SEQUENCE: 126

| | |
|---|---:|
| atgggcgtgc acgagtgccc cgcctggctg tggctgctcc tgagcctgct cagcctgccc | 60 |
| ctcggactgc ccgtgctcgg agccccaccc aggctgatct gcgacagcag ggtgctggag | 120 |
| aggtacctcc tggaggccaa ggaggccgag aacatcacca caggctgcgc cgagcactgc | 180 |
| agcctgaacg agaacatcac cgtgcccgac accaaggtga acttctacgc ctggaagagg | 240 |

| | |
|---|---|
| atggaggtgg gccagcaggc cgtggaggtg tggcagggcc tggccctcct gagcgaggcc | 300 |
| gtgctgagag gccaggccct gctcgtgaac agcagccagc cctgggagcc actgcagctg | 360 |
| cacgtggaca aggccgtgag cggcctgagg agcctgacca cactgctcag ggccctgggc | 420 |
| gcacagaagg aggccatcag cccacccgac gccgcaagcg ccgcacccct gaggaccatc | 480 |
| accgccgaca ccttcaggaa gctgttcaga gtgtacagca acttcctgag aggcaagctg | 540 |
| aagctgtaca ccggcgaggc ctgcaggacc ggcgacagat ga | 582 |

<210> SEQ ID NO 127
<211> LENGTH: 1386
<212> TYPE: DNA
<213> ORGANISM: Homo sapiens

<400> SEQUENCE: 127

| | |
|---|---|
| atgcagcgcg tgaacatgat catggcagaa tcaccaggcc tcatcaccat ctgcctttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttttcc tgatgtggac | 600 |
| tatgtaaatt ctactgaagc tgaaaccatt ttggataaca tcactcaaag cacccaatca | 660 |
| tttaatgact tcactcgggt tgttggtgga gaagatgcca aaccaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca actacaatgc agctattaat aagtacaacc atgacattgc ccttctggaa | 960 |
| ctggacgaac cctagtgct aaacagctac gttacaccta tttgcattgc tgacaaggaa | 1020 |
| tacacgaaca tcttcctcaa atttggatct ggctatgtaa gtggctgggg aagagtcttc | 1080 |
| cacaaaggga atcagctttt agttcttcag taccttagag ttccacttgt tgaccgagcc | 1140 |
| acatgtcttc gatctacaaa gttcaccatc tataacaaca tgttctgtgc tggcttccat | 1200 |
| gaaggaggta gagattcatg tcaaggagat agtggggac cccatgttac tgaagtggaa | 1260 |
| gggaccagtt tcttaactgg aattattagc tggggtgaag agtgtgcaat gaaaggcaaa | 1320 |
| tatggaatat ataccaaggt atcccggtat gtcaactgga ttaaggaaaa aacaaagctc | 1380 |
| acttaa | 1386 |

<210> SEQ ID NO 128
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

| | |
|---|---|
| atgcagagag tgaacatgat catggccgag agccctggcc tgattaccat ctgcctgctg | 60 |
| ggctatctgc tgtccgccga gtgtaccgtg ttcctggacc acgagaacgc caataagatc | 120 |
| ctcaacaggc ccaagaggta caacagcgga aagctggagg agtttgtcca gggcaacctg | 180 |
| gagagagagt gcatggagga gaagtgtagc ttcgaagagg ccagggaagt gttcgagaac | 240 |
| accgaaagga caaccgagtt ctggaagcag tacgtggacg agaccaatg cgaatccaac | 300 |
| ccctgcctga atggaggcag ctgcaaggac gatatcaaca gctacgagtg ctggtgcccc | 360 |
| tttggattcg aaggcaagaa ctgcgagctg gacgtcacat gtaatattaa aaacggcaga | 420 |
| tgcgagcagt tctgcaagaa ttccgccgat aacaaggtcg tgtgcagctg taccgagggc | 480 |
| tacagactcg ccgagaatca aagagctgt gagcccgccg tccccttttcc ctgtggaagg | 540 |
| gtgtccgtgt cccagacatc caagctgaca agggccgaaa cagtgttccc cgacgtggat | 600 |
| tacgtgaaca gcaccgaggc tgaaaccatc ctcgacaaca tcacccagtc cacccagtcc | 660 |
| ttcaatgact tcaccaggt cgtcggcggc gaagacgcca agcccggaca attcccctgg | 720 |
| caggtcgtgc tgaatggcaa ggtcgatgcc ttttgcggag gctccatcgt gaacgagaag | 780 |
| tggatcgtca ccgctgctca ctgtgtggag accggcgtca aaatcacagt ggtcgctggc | 840 |
| gagcacaaca ttgaggaaac cgagcacacc gagcagaaga gaaacgtgat caggattatt | 900 |
| ccccaccaca actacaatgc cgccatcaac aagtacaacc acgacatcgc tctgttagaa | 960 |
| ctcgatgagc ctctggtgct caacagctat gtgacaccca tctgtatcgc cgacaaggag | 1020 |
| tacaccaaca tcttcctgaa gttcggcagc ggatatgtca gcggatgggg aagggtctttt | 1080 |
| cacaaaggaa ggtccgccct cgtgctgcaa tacctgagag tgcccctggt ggacagggcc | 1140 |
| acctgtctga ggtccacaaa attcaccatc tacaacaaca tgttctgcgc cggcttccat | 1200 |
| gagggcggca gagattcctg ccaaggcgat tccggaggcc cccacgtgac agaggtcgag | 1260 |
| ggcacctcct tcctgaccgg aatcattagc tggggagagg agtgcgccat gaagggaaag | 1320 |
| tacggcatct acaccaaggt gtccaggtat gtcaactgga tcaaggagaa gacaaaactg | 1380 |
| acctaa | 1386 |

<210> SEQ ID NO 129
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129

| | |
|---|---|
| auaagugaa | 9 |

<210> SEQ ID NO 130
<211> LENGTH: 1065
<212> TYPE: RNA
<213> ORGANISM: Homo sapiens

<400> SEQUENCE: 130

| | |
|---|---|
| augcuguuua aucugaggau ccuguuaaac aaugcagcuu uuagaaaugg ucacaacuuc | 60 |
| augguucgaa auuucggug uggacaacca cuacaaaaua aagugcagcu gaagggccgu | 120 |
| gaccuucuca cucuaaaaaa cuuuaccgga gaagaaauua auauaugcu auggcuauca | 180 |
| gcagaucuga aauuuaggau aaaacagaaa ggagaguauu ugccuuuauu gcaagggaag | 240 |
| uccuuaggca ugauuuuuga gaaagaagu acucgaacaa gauugcuac agaaacaggc | 300 |

-continued

```
uuugcacuuc ugggaggaca uccuuguuuu cuuaccacac aagauauuca uuugggugug      360
aaugaaaguc ucacggacac ggcccgugua uugucuagca uggcagaugc aguauuggcu      420
cgaguguaua aacaaucaga uuuggacacc cuggcuaaag aagcauccau cccaauuauc      480
aaugggcugu cagauuugua ccauccuauc cagauccugg cugauuaccu cacgcuccag      540
gaacacuaua gcucucugaa aggucuuacc cucagcugga ucggggaugg gaacaauauc      600
cugcacucca ucaugaugag cgcagcgaaa uucggaaugc accuucaggc agcuacucca      660
aaggguuaug agccggaugc uaguguaacc aaguuggcag agcaguaugc caaagagaau      720
gguaccaagc uguugcugac aaaugaucca uuggaagcag cgcauggagg caauguauua      780
auuacagaca cuuggauaag cauggacaa gaagaggaga agaaaaagcg gcuccaggcu       840
uuccaagguu accagguuac aaugaagacu gcuaaaguug cugccucuga cuggacauuu      900
uuacacugcu ugcccagaaa gccagaagaa guggaugaug aagucuuuua uucuccucga     960
ucacuagugu ucccagaggc agaaaacaga aaguggacaa ucauggcugu caugugucc      1020 cugcugacag auuacucacc ucagcuccag aagccuaaau uuuga                    1065
```